United States Patent
Huang et al.

(10) Patent No.: US 11,142,543 B2
(45) Date of Patent: Oct. 12, 2021

(54) ANTIDEPRESSANT COMPOUND AND PREPARATION METHOD AND APPLICATION THEREOF

(71) Applicant: SHANGHAI INSTITUTE OF MATERIA MEDICA, CHINESE ACADEMY OF SCIENCES, Shanghai (CN)

(72) Inventors: Chenggang Huang, Shanghai (CN); Yang Li, Shanghai (CN); Hualiang Jiang, Shanghai (CN); Yang Xie, Shanghai (CN); Fei Guo, Shanghai (CN); Zhixiong Li, Shanghai (CN); Mingcang Chen, Shanghai (CN); Mingyue Zheng, Shanghai (CN); Zhaolin Sun, Shanghai (CN); Yu Gao, Shanghai (CN); Xiaoting Tian, Shanghai (CN); Pei Hu, Shanghai (CN); Bing Zhang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 219 days.

(21) Appl. No.: 16/474,668

(22) PCT Filed: Dec. 29, 2017

(86) PCT No.: PCT/CN2017/120134
§ 371 (c)(1),
(2) Date: Jul. 2, 2019

(87) PCT Pub. No.: WO2018/121770
PCT Pub. Date: Jul. 5, 2018

(65) Prior Publication Data
US 2020/0385418 A1 Dec. 10, 2020

(30) Foreign Application Priority Data
Dec. 30, 2016 (CN) .......................... 201611260514.6

(51) Int. Cl.
*C07H 17/04* (2006.01)
*A61P 25/24* (2006.01)
*C07D 493/10* (2006.01)
*C07H 17/00* (2006.01)

(52) U.S. Cl.
CPC .............. *C07H 17/04* (2013.01); *A61P 25/24* (2018.01); *C07D 493/10* (2013.01); *C07H 17/00* (2013.01)

(58) Field of Classification Search
CPC .......... C07H 17/04; C07H 17/00; A61P 25/24
See application file for complete search history.

(56) References Cited

U.S. PATENT DOCUMENTS

| | | |
|---|---|---|
| 2002/0183294 A1 | 12/2002 | Barraclough et al. |
| 2003/0158161 A1 | 8/2003 | Barraclough et al. |
| 2006/0079505 A1 | 4/2006 | Makings et al. |
| 2009/0227570 A1 | 9/2009 | Kolczewski et al. |
| 2017/0129915 A1 | 5/2017 | Tohda et al. |

FOREIGN PATENT DOCUMENTS

| | | |
|---|---|---|
| CN | 1377367 A | 10/2002 |
| CN | 1452630 A | 10/2003 |
| CN | 1642558 A | 7/2005 |
| CN | 101031296 A | 9/2007 |
| CN | 101214253 A | 7/2008 |
| CN | 101768202 A | 7/2010 |
| CN | 101959876 A | 1/2011 |
| CN | 102924559 A | 2/2013 |
| JP | WO2015/163318 | * 10/2015 |
| WO | 03/082893 A2 | 10/2003 |
| WO | 2005/051380 A1 | 6/2005 |
| WO | 2005/051381 A1 | 6/2005 |
| WO | 2015/163318 A1 | 10/2015 |
| WO | 2019/129176 A1 | 7/2019 |

OTHER PUBLICATIONS

Extended European Search Report dated Jun. 30, 2020 corresponding to EP 17889516.5 filed Dec. 29, 2017; 8 pages.
Pucak, Michele L. et al., "Neuropsychiatric manifestations of depression in multiple sclerosis: neuroinflammatory, neuroendocrine, and neurotrophic mechanisms in the pathogenesis of immune-mediated depression. Historical perspective on multiple sclerosis and depression," *Dialogues Clin. Neurosci.* (Jan. 1, 2007) 9(2):125-138.
English Translation of the International Search Report dated Mar. 30, 2018 corresponding to PCT/CN2017/120134 filed Dec. 29, 2017; 6 pages.

(Continued)

*Primary Examiner* — Timothy R Rozof
(74) *Attorney, Agent, or Firm* — Mintz Levin Cohn Ferris Glovsky and Popeo PC

(57) ABSTRACT

An antidepressant steroid compound and a preparation method and an application thereof; the structure of said compound is shown in formula (I), and the definition of each substituent is as described in the description and claims. Compound of the present invention may be used in the prevention, treatment, therapy or alleviation of a plurality of diseases and conditions such as depression.

(I)

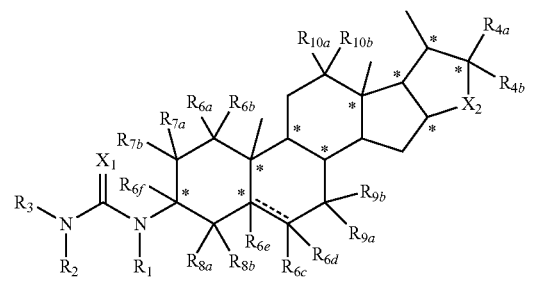

13 Claims, 4 Drawing Sheets

(56) References Cited

OTHER PUBLICATIONS

Lu, Mingzhu et al., "Study on the effect and mechanisms of timosaponin B-II on antidepressant," *Journal of Pharmaceutical Practice* (Jul. 25, 2010); 28(4):283-287; see, English language Abstract on p. 283.

Ren, Li-Xiang et al., "Antidepressant-Like Effects of Sarsasapogenin from *Anemarrhena asphodeloides* BUNGE (Liliaceae)," *Biol. Pharm. Bull.* (2006; accepted Jul. 26, 2006); 29(11):2304-2306.

Ren, Lixiang et al., "Experimental Study of Antidepressant Effects of Total Timosaponin, *Traditional Chinese Drug Research & Clinical Pharmacology*, " (Jan. 2007); 18(1):28-31; see, English language Abstract on p. 29.

Wu, Zhi-tao et al., "Timosaponin A3 induces hepatotoxicity in rats through inducing oxidative stress and down-regulating bile acid transporters," *Acta Pharmacologica Sinica* (pubished online Aug. 4, 2014) 35:1188-1198.

\* cited by examiner

ANTIDEPRESSANT COMPOUND AND PREPARATION METHOD AND APPLICATION THEREOF

TECHNICAL FIELD

The present invention relates to the field of medicine, and in particular to an antidepressant compound or a pharmaceutically acceptable salt, a solvent compound, an optical isomer and a stereoisomer thereof, and a preparation method and use thereof.

BACKGROUND ART

Depression is a common and frequently-occurring disease that endangers human health. In China, the incidence of affective psychosis is 0.76%. The incidence of depression is high, but the cause of morbidity is still not very clear. The traditional view is that the pathogenesis of depression is associated with abnormalities of monoamine neurotransmitters in the brain, including serotonin, acetylcholine and catecholamines, norepinephrine and epinephrine. The most commonly used antidepressants in clinical practice include tricyclic and tetracyclic antidepressants, monoamine oxidase inhibitors, selective 5-HT reuptake inhibitors (SSRIs), atypical antidepressants and lithium salts, etc. Chinese medicine believes that depression is caused by excessive anxiety, and fatigue and injured heart and spleen, and treatment should be based on tranquility and nourishment for vitality. Therefore, in most prescriptions for the treatment of depression in Chinese medicine, *Anemarrhena asphodeloides* Bge. is also a commonly used Chinese herbal medicine.

Alzheimer's disease (AD) is a main type of senile dementias disease. The clinical manifestations of AD are a series of symptoms such as progressive cognitive decline and aggravation of emotional disorders, including short-term memory, speech function, living habit and attention. At present, the pathogenesis of AD is unclear. Therefore, to date, the available medicament treatments for AD are very limited, and the medicaments used to treat AD are mainly aimed at improving the cognitive behavioral symptoms, including: (1) improvement of cholinergic neurotransmission, mainly cholinesterase inhibitors; (2). N-methyl-D-aspartate (NMDA) receptor antagonists, such as memantine. An effective treatment for AD is very lack in the first line of clinical practice.

The main chemical components of Chinese herbal medicine, *Anemarrhena asphodeloides* Bge., are steroidal saponins, dibenzopyrones, polysaccharides and lignins, such as timosaponin A-I, A-II, A-III, A-IV, B-I, B-II and B-III, wherein the structures of the timosaponins A-II and A-IV are unknown; and amemarsaponin A2, i.e., marlogenin-3-O-β-D-glucopyranosy (1→2)-β-D-galactopyranoside B, desgalactotigonin, F-gitonin, smilageninoside and the like. Moreover, it also comprises anemaran A/B/C/D, cis-hinokiresinol, monomethyl-cis-hinokiresinol, oxy-cis-himokiresinol, 2,6,4'-trihydroxy-4-methoxy benzophenone, p-hydroxyphenyl crotonic acid, pentacosyl vinyl ester, β-sitosterol, mangiferin, nicotinic acid, nicotinamide, pantothenic acid and the like.

Recent studies have also shown that timosaponin has a role in anti-senile dementia symptoms, anti-aging, anti-depression and the like. The total saponins of *Rhizoma Anemarrhenae* have antidepressant effects in various depression models, which may be related to enhancing noradrenergic and serotonergic nervous system (Traditional Chinese Drug Research and Clinical Pharmacology, 2007, 18, 29). It has been confirmed by animal experiments that sarsasapogenin contained in *Anemarrhena asphodeloides* Bge. has a certain effect on experimental depression in mice, which can affect the activity of dopamine and monoamine oxidase in the brain of mice, and make such saponins have antidepressant activity (Biol. Pharm. Bull., 2006, 29, 2304-2306). Y I Jia et al. have found that timosaponin B-II has antidepressant activity, and its mechanism may be related to enhancing the effects of 5-HT and DA nervous system in the brain (CN01214253A; Journal of Pharmaceutical Practice, 2010, 28, 283-287).

There is also a need in the art for intensive research and development of antidepressant compounds and anti-Alzheimer's disease compounds.

SUMMARY OF THE INVENTION

The object of the present invention is to provide a sarsasapogenin compound and a pharmaceutically acceptable salt thereof.

The first aspect of the invention provides a compound of formula I, or a pharmaceutically acceptable salt, a solvate, an optically pure isomer or a stereoisomer thereof, or a mixture thereof, formula (I)

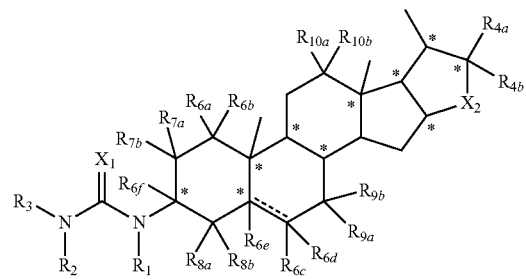

wherein the compound of formula I is formed by linking the following fragment A and fragment B, fragment A

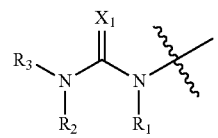

fragment B

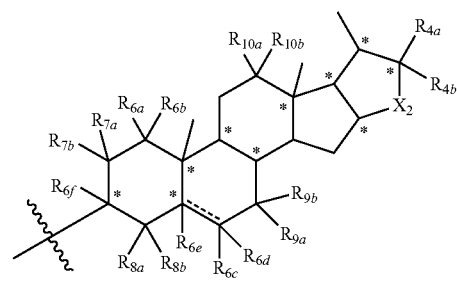

wherein, $R_1$, $R_2$ and $R_3$ are each independently selected from the group consisting of hydrogen, alkyl, substituted alkyl, arylalkyl, substituted arylalkyl, cycloalkyl, substituted cycloalkyl, alkenyl, substituted alkenyl, alkynyl, substituted alkynyl, aryl, substituted aryl, heteroaryl, substituted heteroaryl, heterocycle, and substituted heterocycle; or $R_2$, $R_3$ and attached N together form 3-7 membered saturated or unsaturated heterocycle containing 1-3 N, 0-2 O and/or 0-2 S atoms, wherein the "heterocycle" is unsubstituted, monosubstituted or polysubstituted by the following group(s): hydrogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, alkanoyl, substituted alkanoyl, alkoxycarbonyl, arylalkoxycarbonyl, alkylsulfonyl, alkylsulfinyl, arylsulfonyl, arylalkylsulfonyl, carbamoyl, substituted carbamoyl, carboxy, amido, substituted amido, sulfonamido, substituted sulfonamido;

$R_{4a}$ and $R_{4b}$ are each independently selected from the group consisting of hydrogen, hydroxy, alkyl, substituted alkyl, alkenyl, substituted alkenyl, alkynyl, and substituted alkynyl; or $R_{4a}$, $R_{4b}$ and attached C together form 3-7 membered saturated or unsaturated heterocycle containing 1-3 N, 0-2 O and/or 0-2 S atoms, wherein the "heterocycle" is unsubstituted, monosubstituted or polysubstituted by the following group(s): hydrogen, hydroxy, alkyl, substituted alkyl, alkenyl, substituted alkenyl, alkynyl, substituted alkynyl, $X_1$ is O, S, $NR_5$; $R_5$ is selected from the group consisting of hydrogen, alkyl, cyano, hydroxy and alkoxy;

$X_2$ is O, NH;

$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$ and $R_{10b}$ are each independently selected from the group consisting of absent, hydrogen, halogen, alkyl, substituted alkyl, hydroxy, mercapto, alkylmercapto, alkoxy, substituted alkoxy, amino, substituted amino, alkylamino, substituted alkylamino, disubstituted amino, alkylacyloxy, arylacyloxy, heteroarylacyloxy, and glycosyl; or $R_{6a}$ and $R_{6b}$, $R_{7a}$ and $R_{7b}$, $R_{8a}$ and $R_{8b}$, $R_{9a}$ and $R_{9b}$, and/or $R_{10a}$ and $R_{10b}$ are combined with each other to form carbonyl;

"$=\!\!=$" represents a single bond or double bond;

each * independently represents a racemic, S or R configuration.

In another preferred embodiment, when $R_2$ is H, $R_3$ is alkyl, substituted alkyl, cycloalkyl, substituted cycloalkyl, aryl, substituted aryl, heteroaryl, substituted heteroaryl, heterocycle, substituted heterocycle; or $R_2$, $R_3$ and attached N together form the following structure:

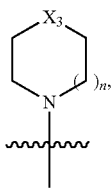

wherein, $X_3$ is C=O, $CH_2$, O or $NR_{11}$, $R_{11}$ is selected from the group consisting of alkyl, substituted alkyl, arylalkyl, substituted arylalkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, alkanoyl, substituted alkanoyl, alkoxycarbonyl, arylalkoxycarbonyl, carbamoyl, substituted carbamoyl, carboxyl, alkylsulfonyl, alkylsulfinyl, arylsulfonyl, arylalkylsulfonyl, amido, substituted amido, sulfonamido, substituted sulfonamide;

n=0, 1 or 2.

In another preferred embodiment, $R_2$ and $R_3$ are each independently selected from the group consisting of H, cycloalkyl, substituted cycloalkyl, heterocyclyl, substituted heterocyclyl, aryl, substituted aryl, and $-MX_3PX_5Q$, wherein, M is alkylenyl, substituted alkylenyl, cycloalkylenyl, or substituted cycloalkylenyl;

$X_3$ is selected from the group consisting of O, S, $(CH_2)_r$, NRa and absent, Ra is selected from the group consisting of H, alkyl, substituted alkyl, alkenyl, substituted alkenyl, alkynyl, and substituted alkynyl, aryl, substituted aryl, heteroaryl, substituted heteroaryl, heterocycle, and substituted heterocycle, r=1, 2, 3, 4 or 5;

P is C=O, C=S, C=$NR_b$, C=C $(R_c)(R_d)$ or absent, $R_b$ is selected from the group consisting of H, hydroxy, alkoxy, cyano and nitro, $R_c$ and $R_d$ are each independently selected from the group consisting of H, alkyl, hydroxy, alkoxy, cyano, and nitro;

$X_5$ is selected from the group consisting of O, S, $(CH_2)_m$, NRe and absent, Re is selected from the group consisting of H, alkyl, and substituted alkyl, wherein m=1, 2, 3, 4 or 5;

Q is H, hydroxy, alkoxy, aryloxy, $NR_fR_g$, alkyl, substituted alkyl, aryl, substituted aryl, heteroaryl, substituted heteroaryl, heterocyclyl, or substituted heterocyclyl, $R_f$ and $R_g$ are each independently H, hydroxy, alkyl, alkoxy, substituted alkyl, alkenyl, substituted alkenyl, alkynyl, substituted alkynyl or alkoxycarbonyl; or $R_f$ and $R_g$ together form 3-7 membered saturated or unsaturated heterocycle containing 1-3 N, 0-2 O and/or 0-2 S atoms, wherein the "heterocycle" is unsubstituted, monosubstituted or polysubstituted by the following group (s): H, hydroxy, amino, alkyl, substituted alkyl, alkenyl, substituted alkenyl, alkynyl, or substituted alkynyl.

In another preferred embodiment, the fragment B is selected from the group consisting of:

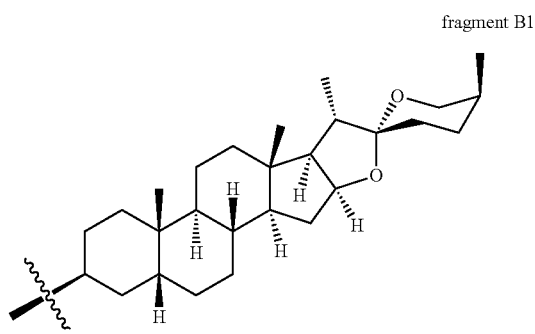

fragment B1

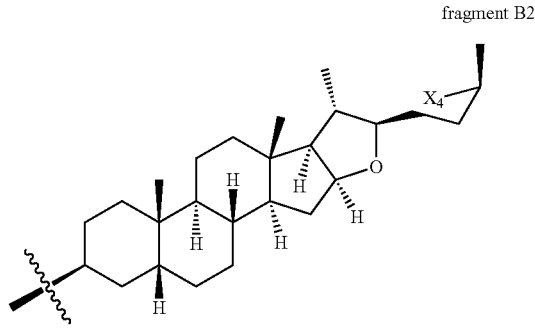

fragment B2

-continued
fragment B3
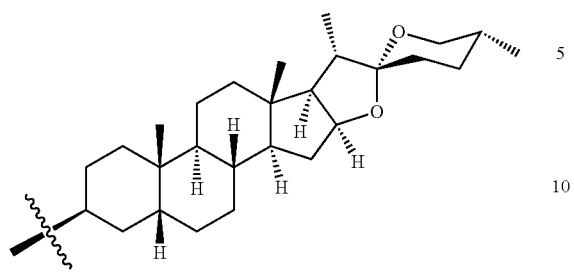
fragment B4
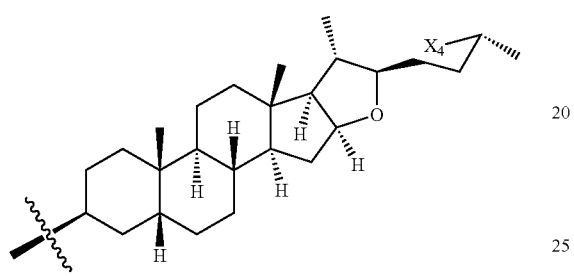
fragment B5
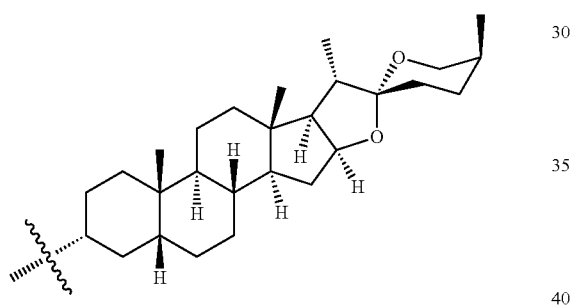
fragment B6
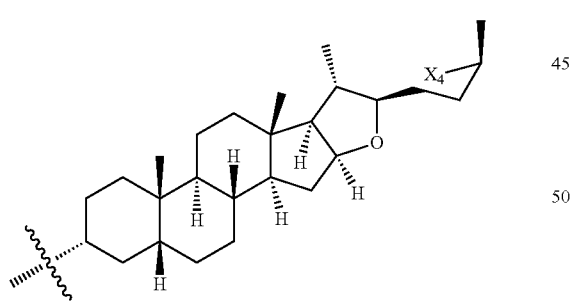
fragment B7
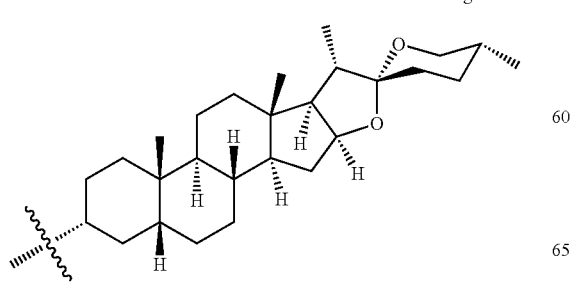
-continued
fragment B8
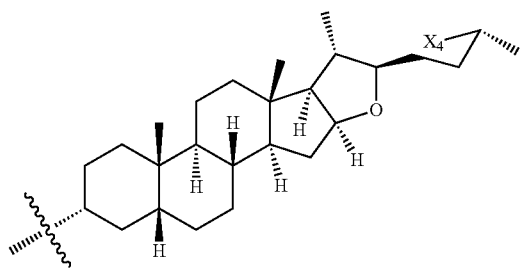
fragment B9
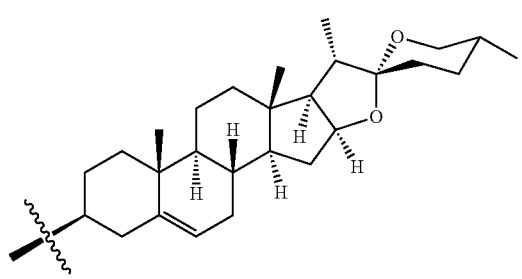
fragment B10
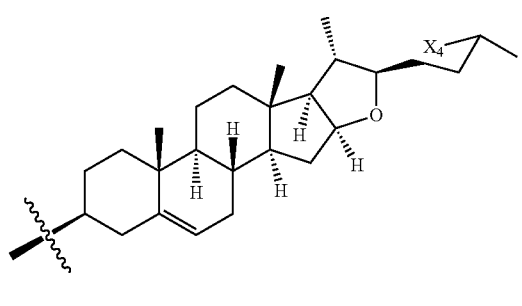
fragment B11
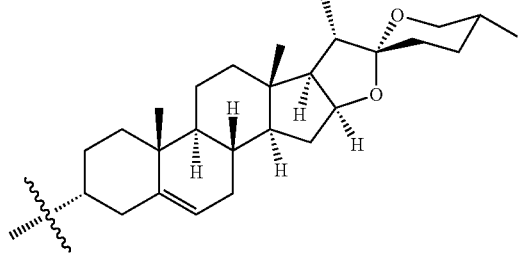
fragment B12
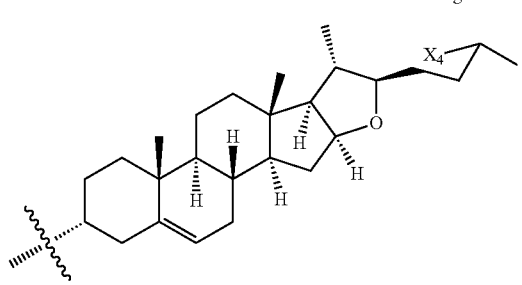

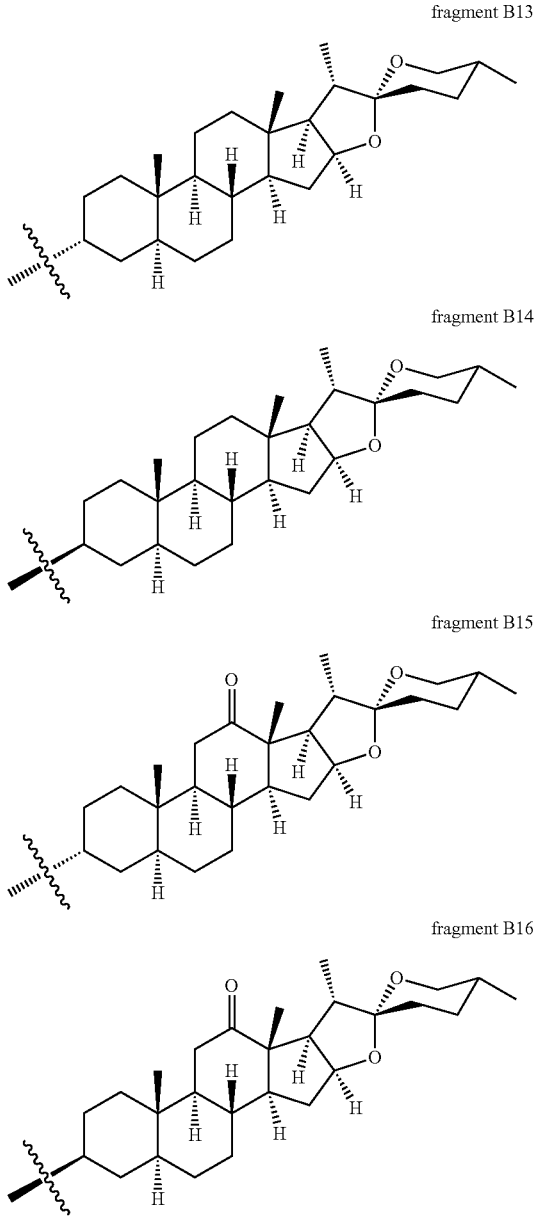

fragment B13 fragment B14 fragment B15 fragment B16 wherein, $X_4$ is $CH_2OR_{12}$, $CH_2N(R_{13})(R_{14})$, aldehyde group, $COOR_{12}$, or $CON(R_{13})(R_{14})$; $R_{12}$, $R_{13}$, and $R_{14}$ are each independently selected from the group consisting of H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, alkanoyl, substituted alkanoyl, alkoxycarbonyl, arylalkoxycarbonyl, alkylsulfonyl, alkylsulfinyl, arylsulfonyl, arylalkylsulfonyl, carbamoyl, and substituted carbamoyl.

In another preferred embodiment, $R_1$, $R_2$, and $R_3$ are each independently selected from the group consisting of H, C3-C8 cycloalkyl, C6-C10 aryl, C3-C8 saturated heterocyclyl, and C1-C4 alkyl, wherein cycloalkyl, aryl, saturated heterocyclyl, and alkyl are optionally monosubstituted, disubstituted or trisubstituted with a substituent selected from the group consisting of halogen, hydroxy, C1-C4 alkyl, C6-C10 aryl, and —C(=O)—O—C1-C4 alkyl; or $R_2$, $R_3$ and attached N together form a 3-7-membered saturated or unsaturated heterocycle containing 1-3 N, 0-2 O and/or 0-2 S atoms, wherein the "heterocycle" is unsubstituted, monosubstituted or polysubstituted by the following group (s): H, C1-C4 alkyl, C1-C4 alkoxy, C2-C4 alkenyl, C2-C4 alkynyl, hydroxyl;

$R_{4a}$, and $R_{4b}$ are each independently selected from the group consisting of H, hydroxy, substituted and unsubstituted C1-C6 alkyl, and the term "substituted" means that the group is substituted by one, two or three substituents selected from the group consisting of halogen, hydroxy, C1-C4 alkyl, C1-C4 alkoxy; or $R_{4a}$, $R_{4b}$ and attached C together form a 3-7 membered saturated or unsaturated heterocycle containing 1-2 O and/or 1-2 S atoms, said "heterocycle" is unsubstituted, monosubstituted or polysubstituted by the following group (s): hydrogen: C1-C4 alkyl, C1-C4 alkoxy, C2-C4 alkenyl, C2-C4 alkynyl, hydroxyl;

$X_1$ is O, S, or $NR_5$, $R_5$ is selected from the group consisting of H, alkyl, and hydroxyl;

$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$, $R_{10b}$ are absent, H, alkyl, substituted alkyl, hydroxyl or mercapto; or $R_{6a}$ and $R_{6b}$, $R_{7a}$ and $R_{7b}$, $R_{8a}$ and $R_{8b}$, $R_{9a}$ and $R_{9b}$, and/or $R_{10a}$ and $R_{10b}$ are combined with each other to form carbonyl, "$=$" represents a single bond or double bond.

In another preferred embodiment, $X_1$ is O.

In another preferred embodiment, $R_1$ is H.

In another preferred embodiment, $R_2$ and $R_3$ are each independently selected from the group consisting of hydrogen, C3-C12 cycloalkyl, C6-C10 aryl, C3-C8 saturated heterocyclyl, and C1-C4 alkyl, wherein the cycloalkyl, aryl, saturated heterocyclyl, and alkyl are optionally monosubstituted, disubstituted or trisubstituted with a substituent selected from the group consisting of halogen, hydroxy, carboxy, C1-C4 alkyl, C6-C10 aryl, 3-8 membered heteroaryl, —C(=O)—OC1-C4 alkyl, 3-7-membered saturated or unsaturated heterocycle, —$NR_{f1}R_{g1}$, —C (=O) $NR_{f1}R_{g1}$, —O—C(=O) (C1-C4 alkylene)$NR_{f1}R_{g1}$, —O—C(=O) (3-8 membered heteroaryl), —NHCO (C1-C4 alkylene)$NR_{f1}R_{g1}$, and —NHCONR$_{f1}R_{g1}$, each $R_{f1}$ and each $R_{g1}$ are independently selected from the group consisting of: H, C1-C4 alkyl, —C(=O)C1-C6alkyl, —C(=O) (3-8 membered heteroaryl), and —C(=O) (C1-C4 alkylene) (3-8 membered heteroaryl), wherein the alkyl is unsubstituted or substituted by a substituent selected from the group consisting of: hydroxy, amino, carboxyl, N (C1-C4 alkyl) (C1-C4 alkyl); or $R_{f1}$, $R_{g1}$ and attached N together form 3-8 membered saturated heterocycle, optionally substituted by the following group: C1-C4 alkyl, C-C4alkoxy, halogen, hydroxy, amino;

or $R_2$, $R_3$ and attached N together form a 3-7 membered saturated or unsaturated heterocycle containing 1-3 N, 0-2 O and/or 0-2 S atoms;

wherein the "heterocycle" is unsubstituted, monosubstituted or polysubstituted by the following group (s): H, C1-C4 alkyl, C1-C4 alkoxy, hydroxy, 3-8 membered heteroaryl.

In another preferred embodiment, $R_3$ is phenyl, cyclohexyl, cyclopentyl, adamantyl, C1-C4 alkyl, C3-C8 saturated heterocycle, and the above group is optionally substituted by a substituent selected from the group consisting of hydroxy, C1-C4 alkyl, halogen, phenyl, and —C (=O)—OC1-C4 alkyl.

In another preferred embodiment, $X_1$ is O;

$R_1$ is H;

$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$, $R_{10b}$ are all hydrogen;

R₂, R₃ are each independently selected from the group consisting of H, C3-C8 cycloalkyl, C6-C10 aryl, C3-C8 saturated heterocyclyl, C1-C4 alkyl, wherein the cycloalkyl, aryl, saturated heterocyclyl, alkyl are optionally monosubstituted, disubstituted or trisubstituted with a substituent selected from the group consisting of halogen, hydroxy, C1-C4 alkyl, C6-C10 aryl, and —C(=O)—OC1-C4 alkyl; or R₂, R₃ and attached N together form a 3-7 membered saturated or unsaturated heterocycle containing 1-3 N, 0-2 O and/or 0-2 S atoms, said "heterocycle" is unsubstituted, monosubstituted or polysubstituted by the following group (s): H, C1-C4 alkyl, C1-C4alkoxy and hydroxyl.

In another preferred embodiment, fragment B is any fragment of fragment B1-fragment B8.

In another preferred embodiment, R₁ is H, R₂ is H, R₃ is a cyclohexyl. In another preferred embodiment, fragment B is fragment B1, fragment B3, fragment B5 or fragment B7.

In another preferred embodiment, X₁ is O;
R₁ is H;
R_{6a}, R_{6b}, R_{6c}, R_{6d}, R_{6e}, R_{6f}, R_{7a}, R_{7b}, R_{8a}, R_{8b}, R_{9a}, R_{9b}, R_{10a}, R_{10b} are all hydrogen;
R₂ is cyclohexyl, cyclopentyl or adamantyl;
fragment B is R₃ is -MX₃PX₅Q, wherein,
M is selected from the group consisting of C1-C4 alkylenyl,
X₃ is selected from the group consisting of O, NRa or absent, Ra is selected from the group consisting of H, and alkyl,
P is C=O or absent,
X₅ is selected from the group consisting of O, (CH₂)_m, NRe or absent, Re is selected from the group consisting of H, alkyl, substituted alkyl, m=0, 1, 2, 3,
Q is H, hydroxy, alkoxy, amino, alkyl, substituted alkyl, or NR_fR_g, R_f and R_g are each independently H, alkyl, or substituted alkyl; or R_f and R_g together form 3-7 membered saturated or unsaturated heterocycle containing 1-3 N, 0-2 O and/or 0-2 S atoms, wherein such "heterocycle" is unsubstituted, monosubstituted or polysubstituted by the following group (s): H, hydroxy, amino, alkyl, substituted alkyl, alkenyl, substituted alkenyl, alkynyl, and substituted alkynyl.

The compound is:

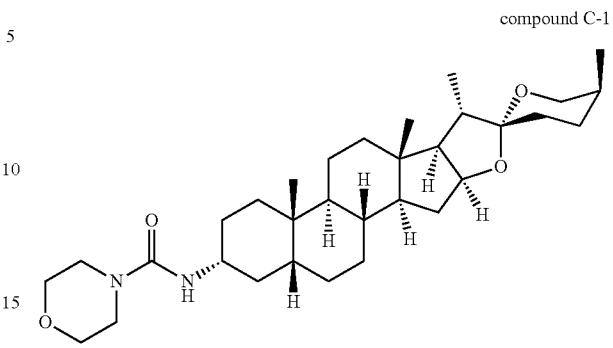

compound C-1 compound C-2 compound C-3 compound C-4 compound C-5

-continued
compound C-6
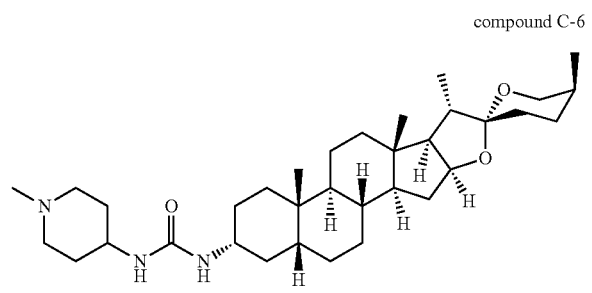
compound C-7
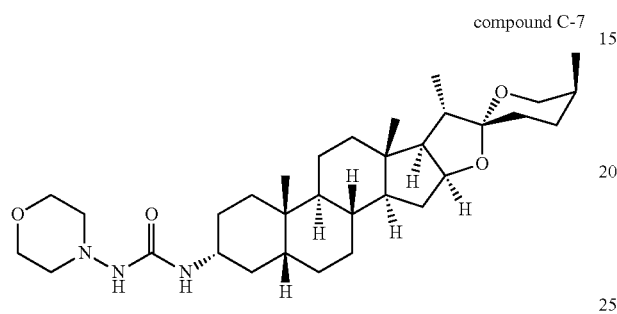
compound C-8
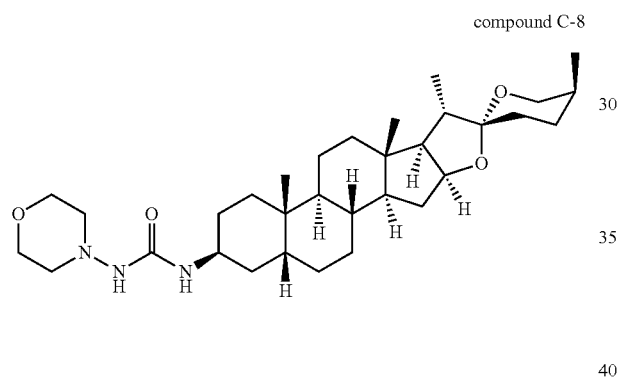
compound C-9
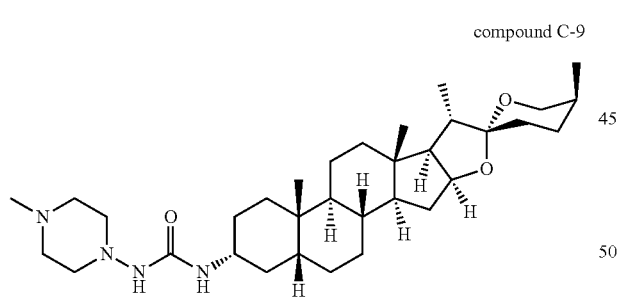
compound C-10
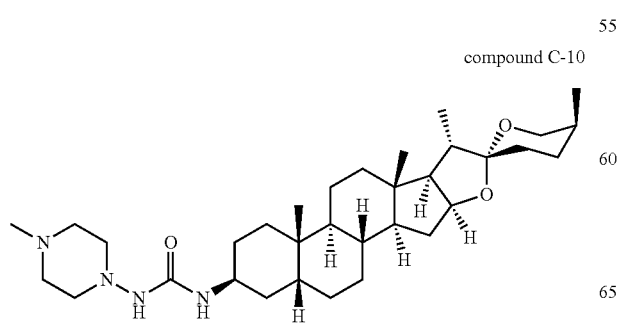
-continued
compound C-11
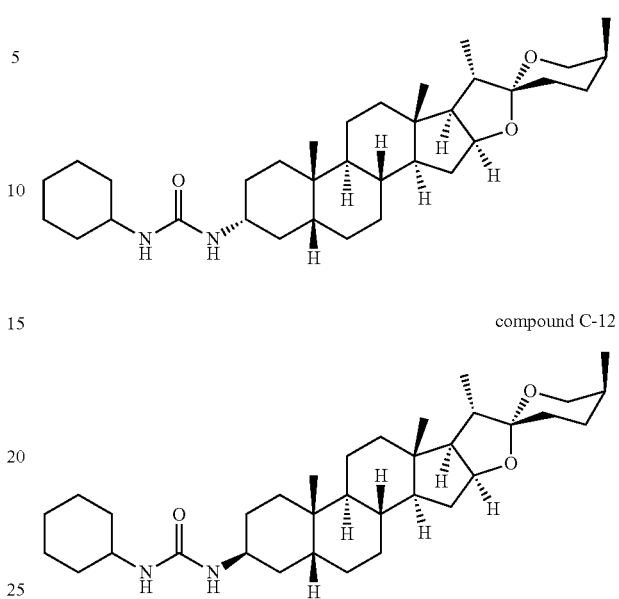
compound C-12
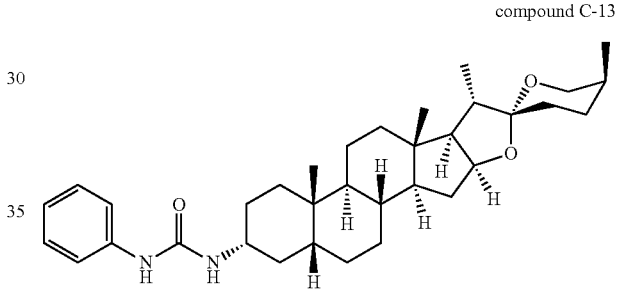
compound C-13
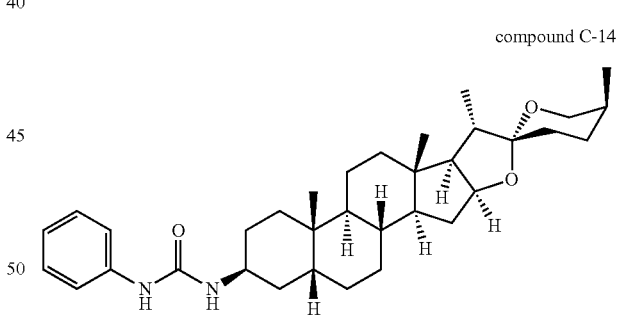
compound C-14
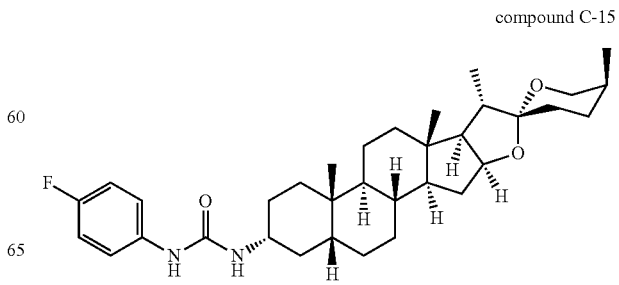
compound C-15 compound C-16
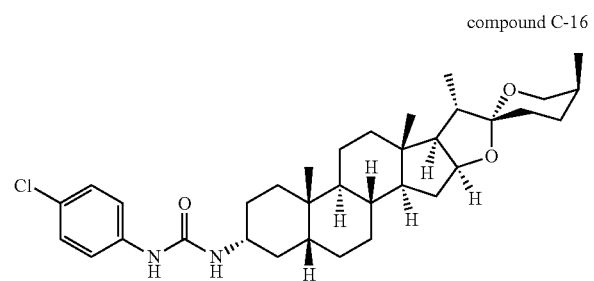
compound C-17
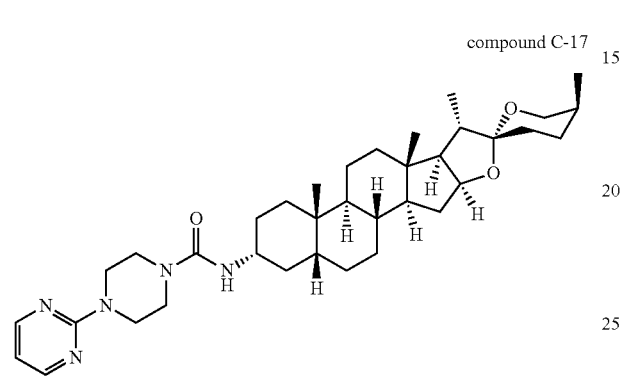
compound C-18
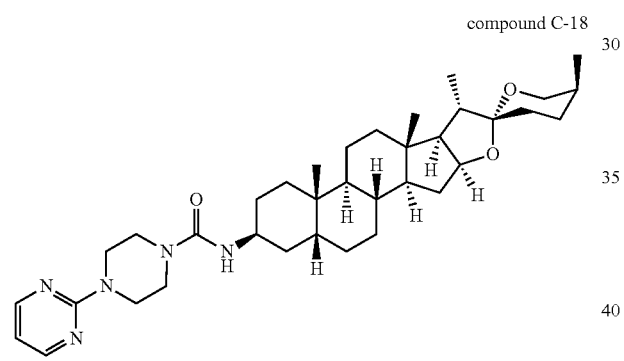
compound C-19
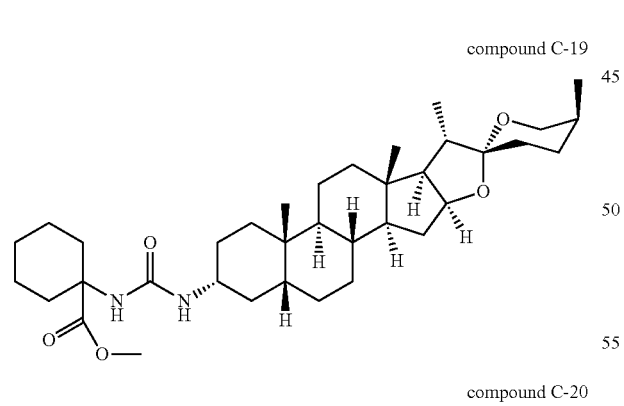
compound C-20
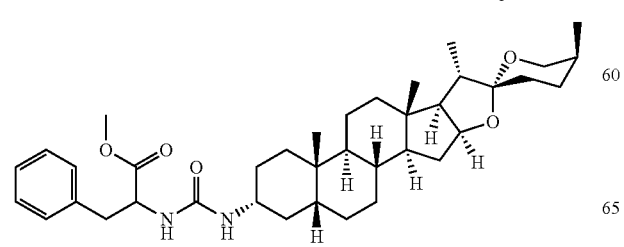
compound C-21
compound C-22, compound C-23, compound C-24, compound C-25
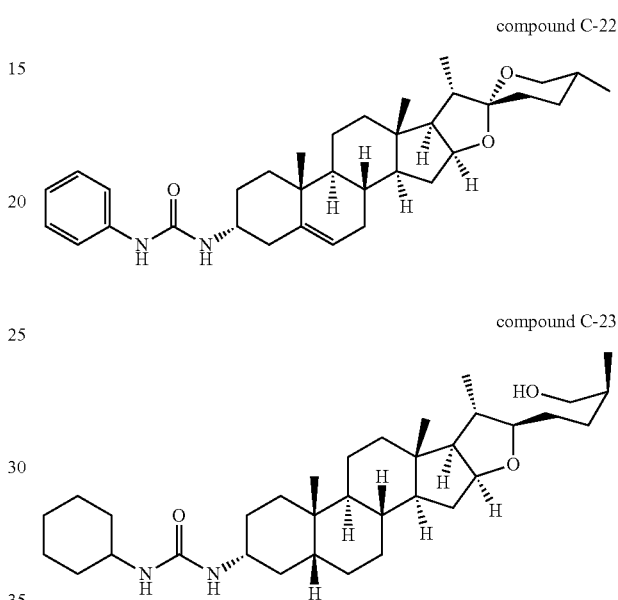
compound C-26
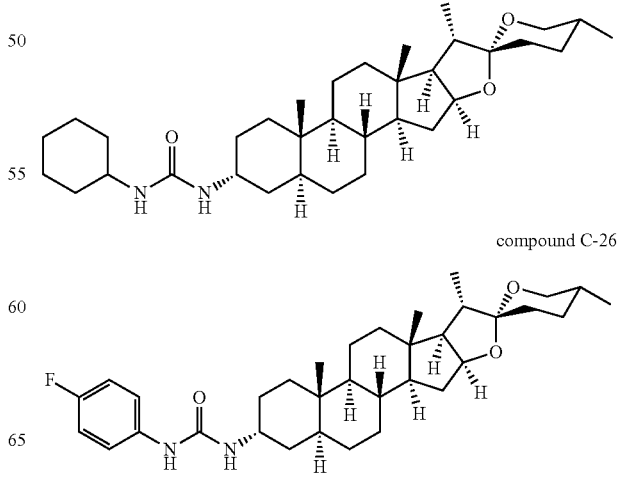

-continued
compound C-27
compound C-28
compound C-29
compound C-30
compound C-31
compound C-32
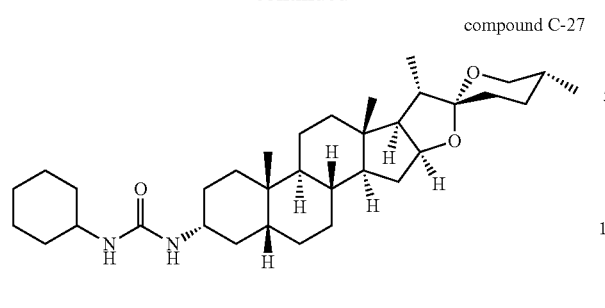
compound C-33
compound C-34
compound C-35
compound C-36
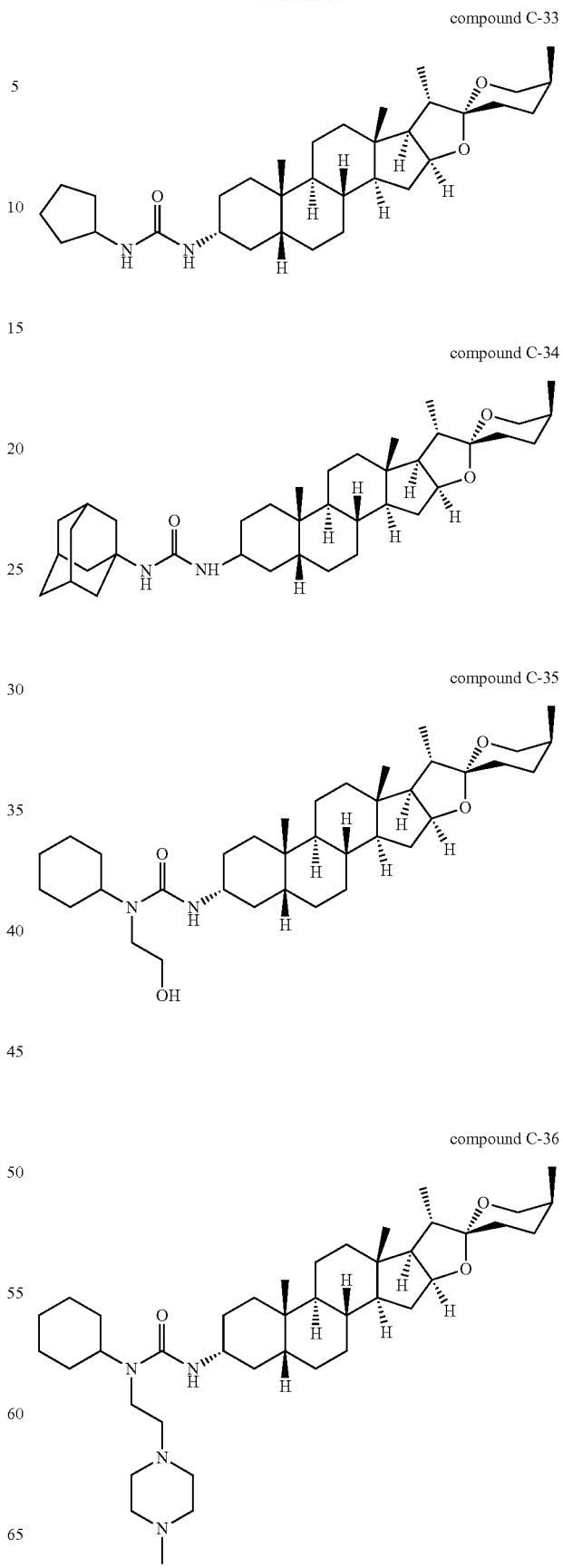

compound C-37
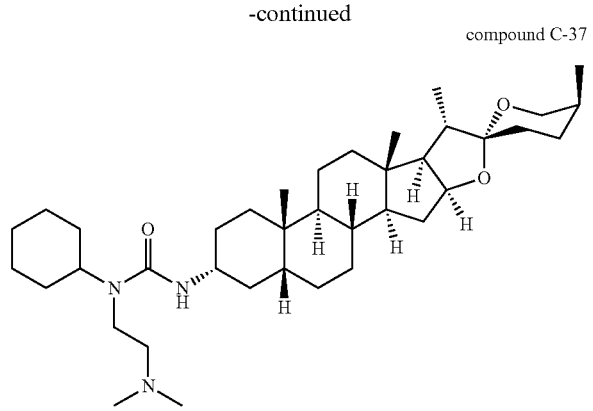
compound C-38
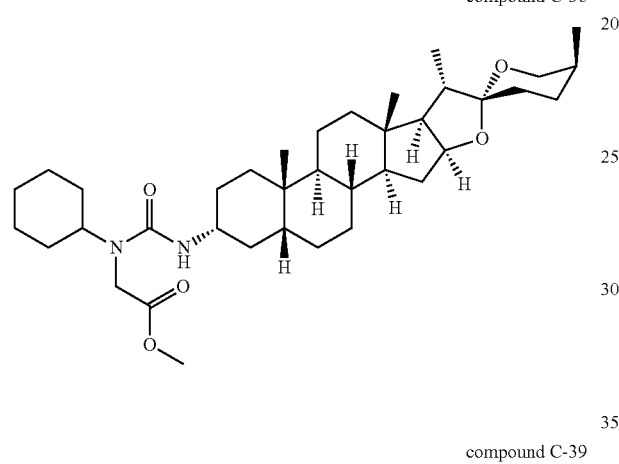
compound C-39
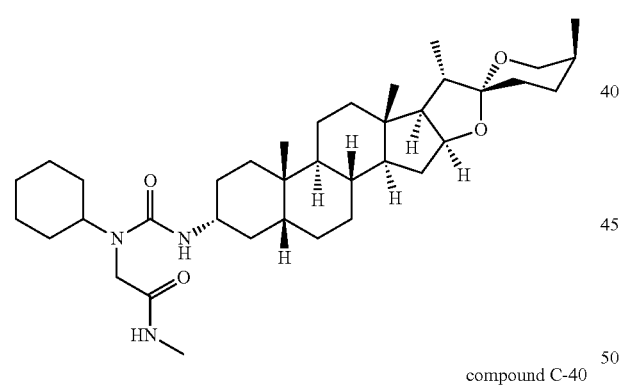
compound C-40
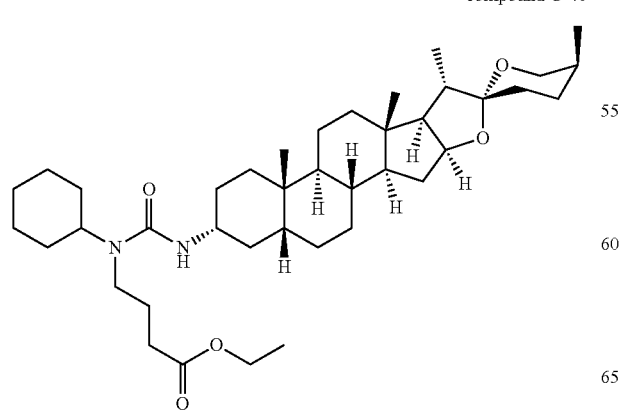
compound C-41
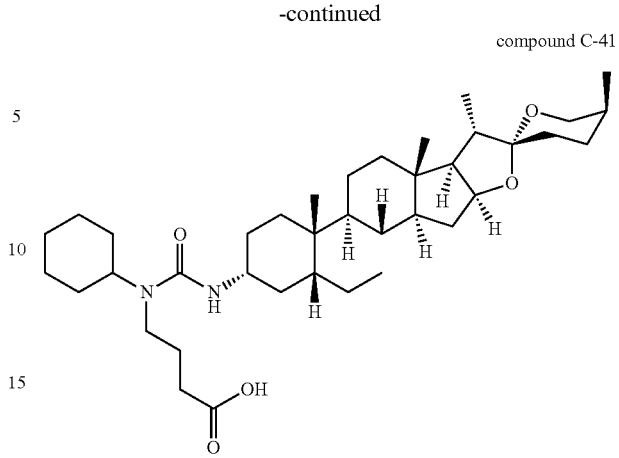
compound C-42
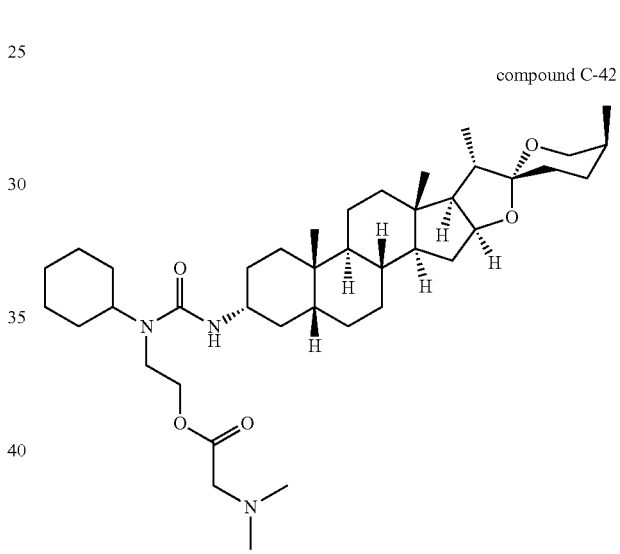
compound C-43
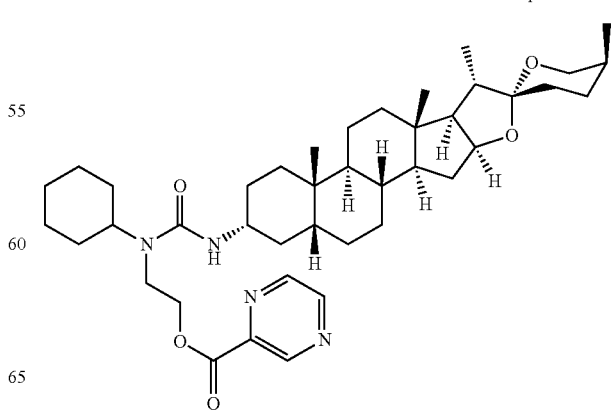

compound C-44
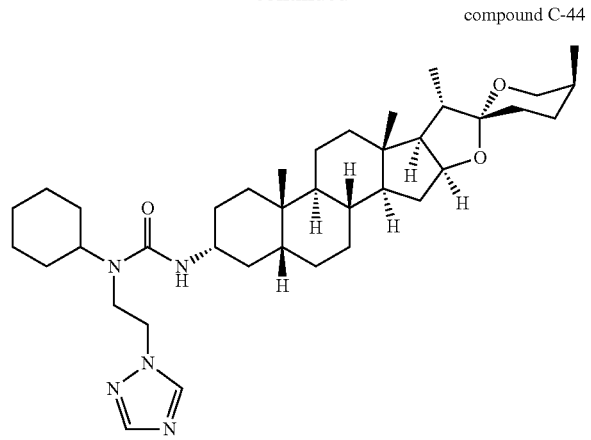
compound C-45
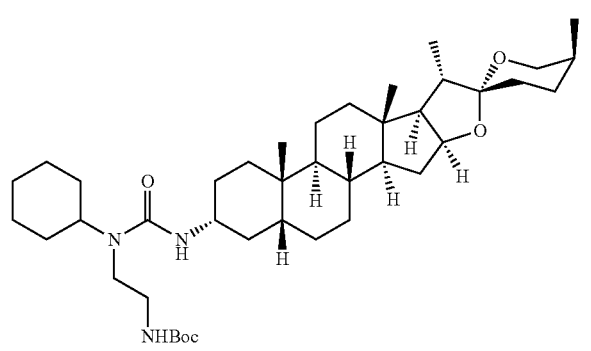
compound C-46
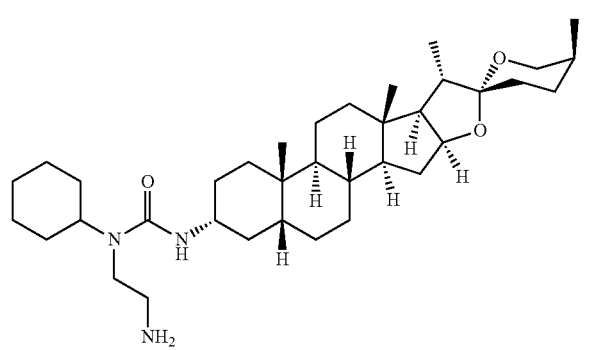
compound C-47
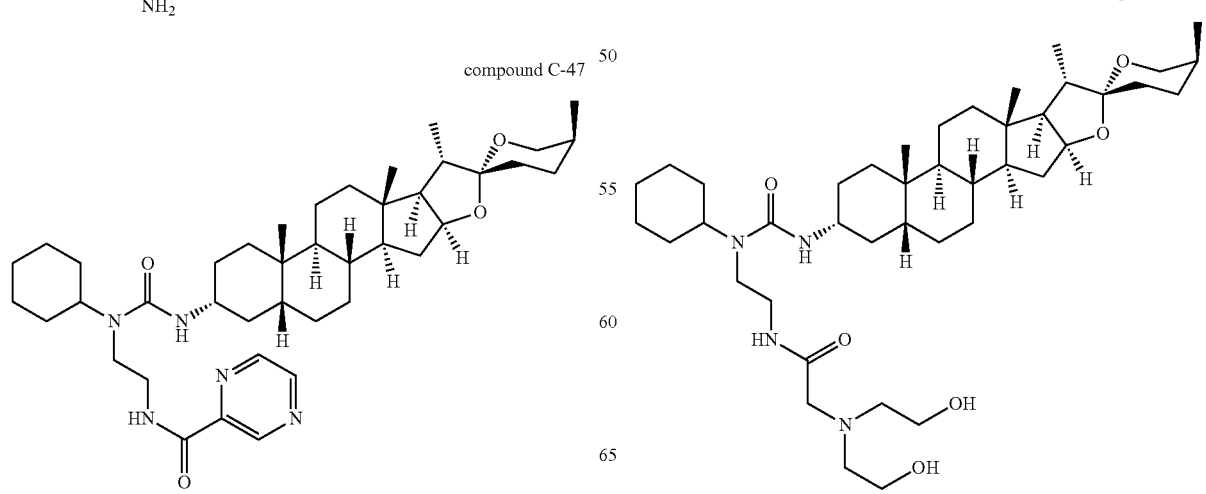
compound C-48
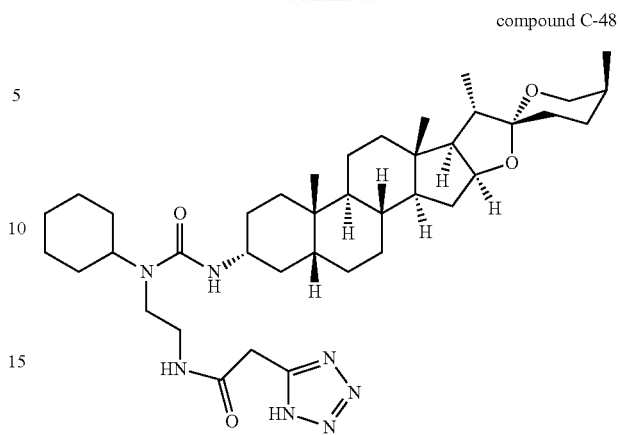
compound C-49
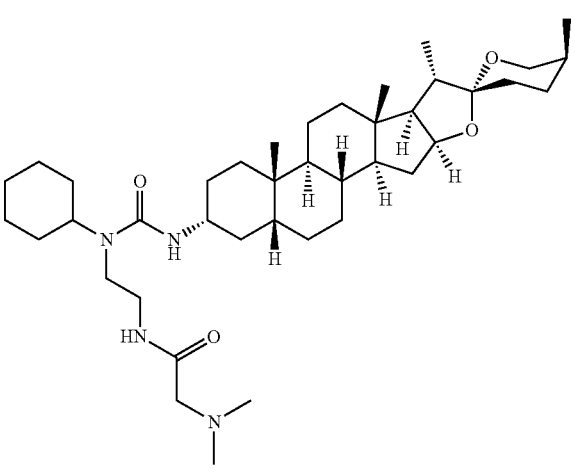
compound C-50 compound C-51
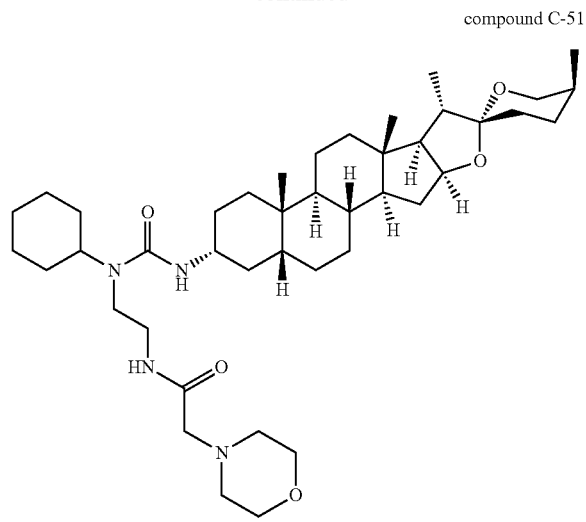
compound C-54
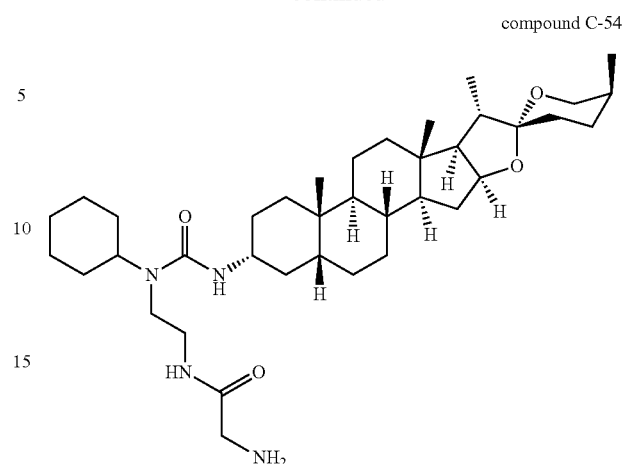
compound C-52
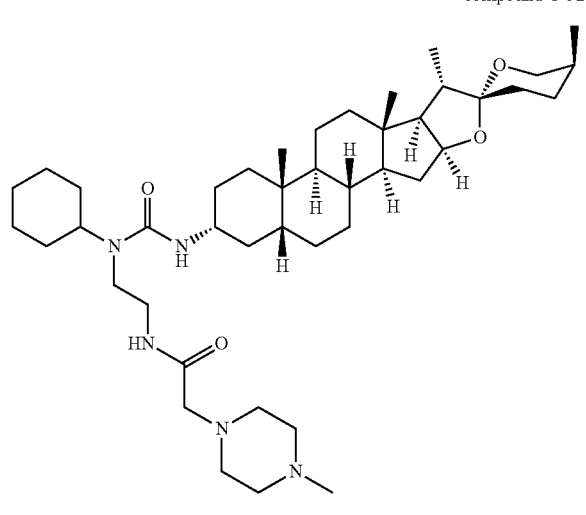
compound C-55
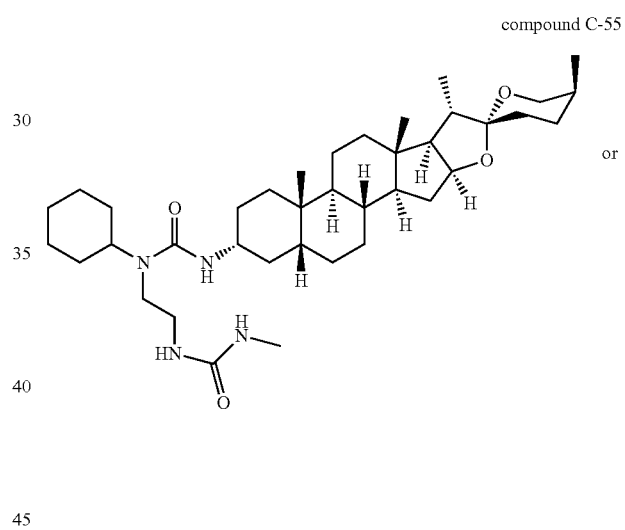
or
compound C-53
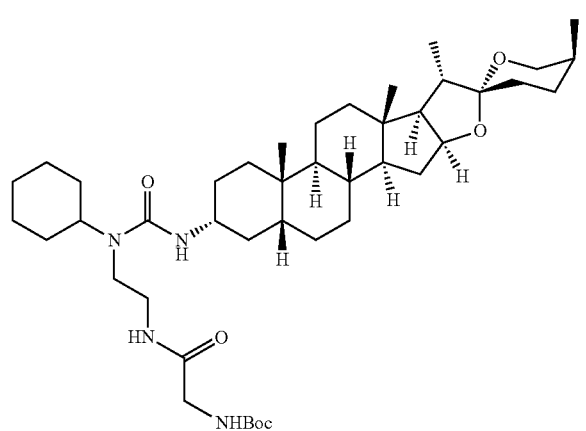
compound C-56
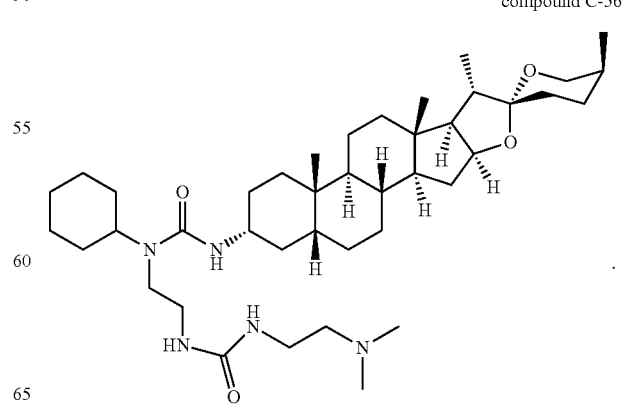
.

The second aspect of the present invention provides a preparation method of the compound, or the pharmaceutically acceptable salt, solvate, optically pure isomer or stereoisomer thereof according to the first aspect, which comprises the step of:

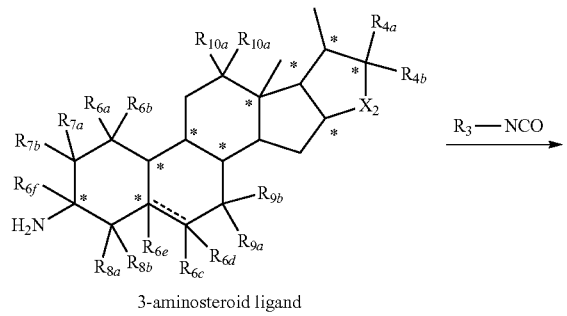
3-aminosteroid ligand

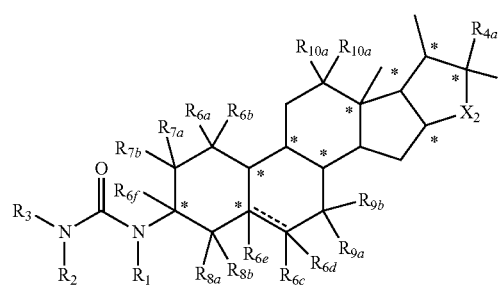

(a) reacting 3-aminosteroid ligand with an isocyanate to give the compound according to the first aspect, wherein $R_1$ and $R_2$ are H, and the other substituents are as defined in the first aspect.

The above 3-aminosteroid ligand may be an optically pure chiral compound or a mixture of optically pure chiral compounds in various ratios. When the above 3-aminosteroid ligand is a mixture of optically pure chiral compounds in various ratios, the preparation method further comprises a step of subjecting the compound of the first aspect obtained in the step a) to chiral resolution to obtain an optically pure chiral compound.

The third aspect of the present invention provides a preparation method of the compound, or the pharmaceutically acceptable salt, solvate, optically pure isomer or stereoisomer thereof according to the first aspect, which comprises the steps of:

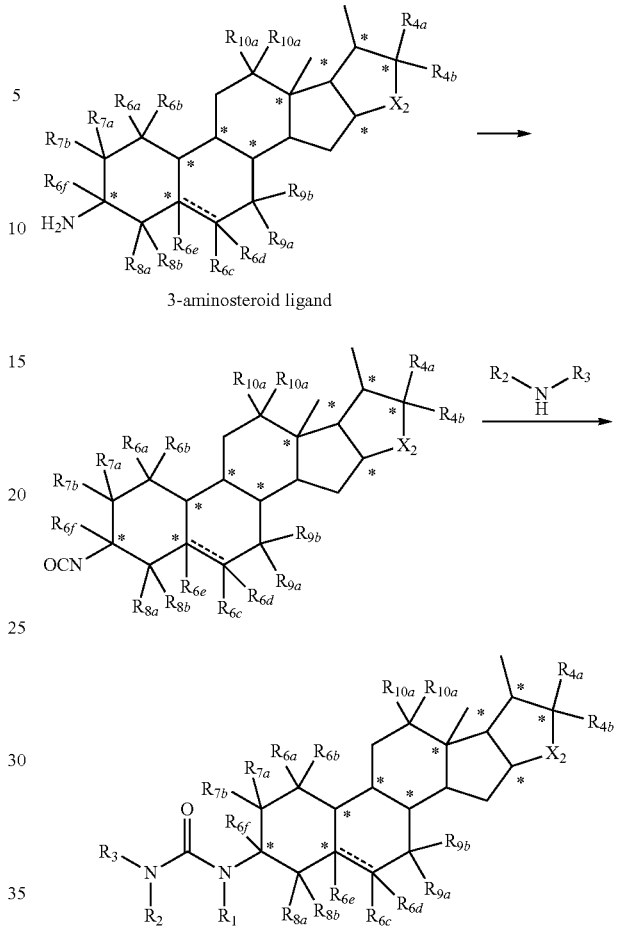

(i) preparing 3-isocyanate steroid compound from 3-aminosteroid ligand;

(ii) reacting 3-isocyanate steroid compound with $NHR_2R_3$ to give the compound of claim 1, wherein $R_1$ is H, and the other substituents are as defined in the first aspect.

The above 3-aminosteroid ligand may be an optically pure chiral compound or a mixture of optically pure chiral compounds in various ratios. When the above 3-aminosteroid ligand is a mixture of optically pure chiral compounds in various ratios, the preparation method further comprises the step of subjecting the compound of the first aspect obtained in the step ii) to chiral resolution to obtain an optically pure chiral compound.

In another preferred embodiment, the compounds of the invention are synthesized using the following route:

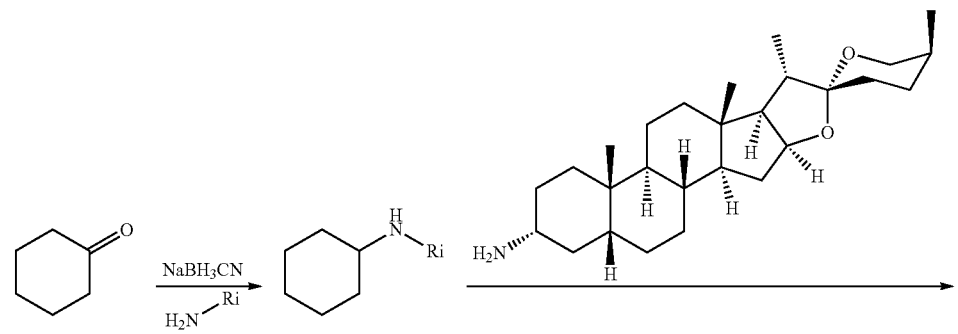

-continued
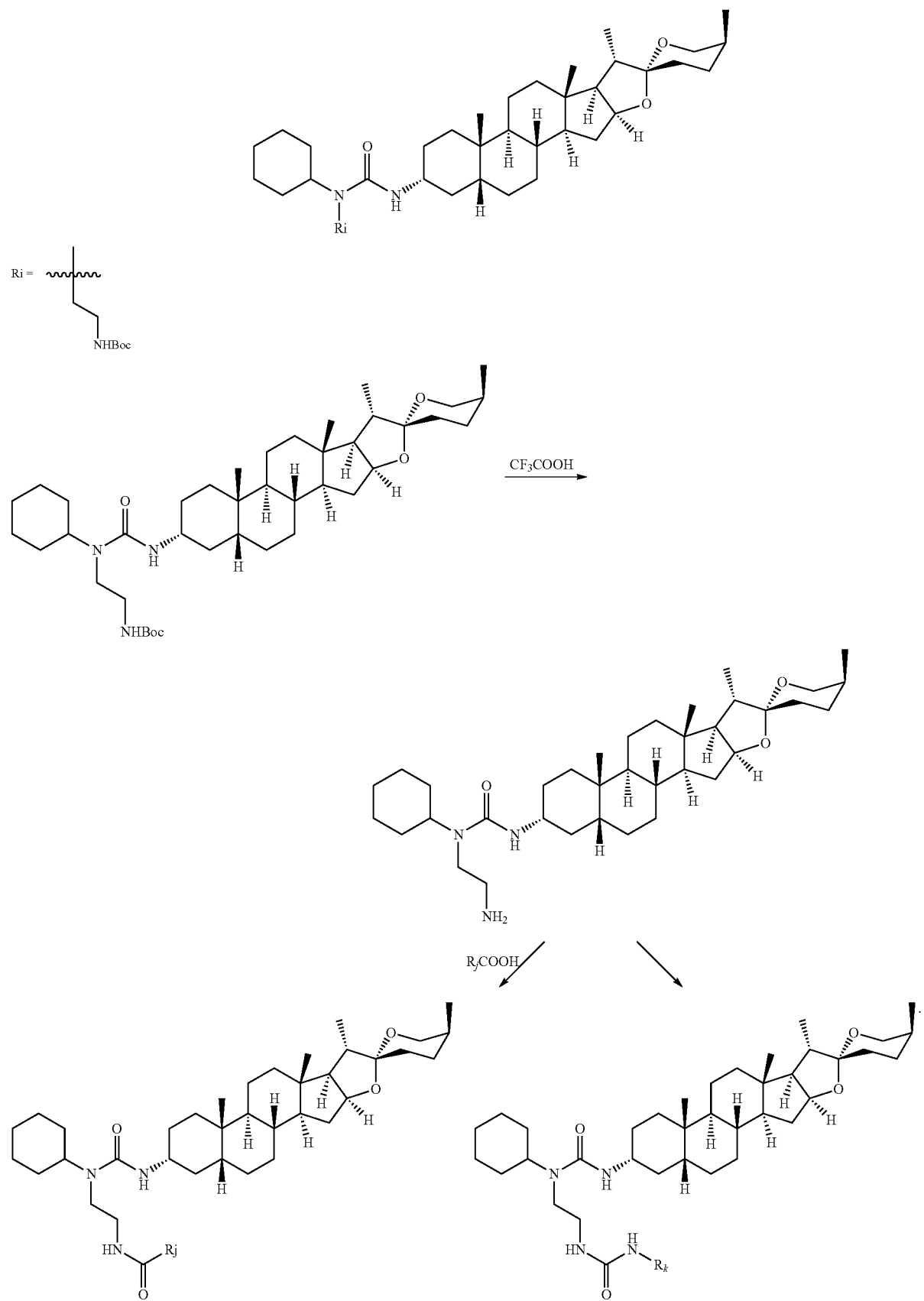

The fourth aspect of the invention provides a pharmaceutical mixture comprising two or more compounds selected from the group consisting of the compound, or the pharmaceutically acceptable salt, solvate, optically pure isomer, stereoisomer thereof according to the first aspect.

In another preferred embodiment, the pharmaceutical mixture is a mixture of any two or more of compound C-1 to compound C-32.

The components in the pharmaceutical mixture in the present invention may be mixed in any mass ratio. For example, when the pharmaceutical mixture is a mixture of any two of compound C-1 to compound C-32, the mass ratio is 0.01:0.99-0.99:0.01, preferably 1:9-9:1, 2:8-8:2, 3:7-7:3 or 4:6-6:4.

The fifth aspect of the invention provides a pharmaceutical composition comprising the compound, or the pharmaceutically acceptable salt, solvate, optically pure isomer, stereoisomer thereof according to the first aspect or the pharmaceutical mixture according to fourth aspect; and a pharmaceutically acceptable carrier.

In another preferred embodiment, the pharmaceutical composition may further comprise an additional therapeutic agent selected from the group consisting of: an antidepressant, an anti-manic drug, a Parkinson's disease therapeutic, an Alzheimer's disease therapeutic, or a combination thereof.

In another preferred embodiment, the pharmaceutical composition may further comprise an additional therapeutic agent, such as moclobemide, toloxatone, fluoxetine, paroxetine, citalopram, sertraline, venlafaxine, trimipramine, trazodone, imipramine, desipramine, clomipramine, amitriptyline, nortriptyline, doxepin, maprotiline, loxapine, amoxapine, mirtazapine, buspirone, chlormezanone, tandospirone, lithium carbonate, tacrine, huperzine A, galantamine, donepezil, rivastigmine, memantine, pramipexole, talipexole, ropinirole, or a combination thereof.

The compounds of the invention may be used alone or in combination with other therapeutic agents. The combination therapy can provide a synergistic effect, i.e., an effect achieved by the use of the compounds together is greater than the sum of the effects produced by the use of the compounds, respectively. The combination therapy can be carried out in a simultaneous or continuous regimen. When administered continuously, the composition can be administered in two or more ways. The compounds can be administered together in a single pharmaceutical combination, or separately, and when administered separately, the compounds can be administered simultaneously or sequentially in any order.

The compounds of the invention may be administered by any route appropriate to the condition being treated. Suitable routes include, but are not limited to, oral, parenteral (including subcutaneous, intramuscular, intravenous, intraarterial, intradermal), vaginal, intraperitoneal, intrapulmonary, and intranasal administration. It will be appreciated that the preferred route may vary, for example, based on the condition of the patient. When the compound is administered orally, it can be formulated into a pill, capsule, tablet or the like with a pharmaceutically acceptable carrier or excipient. When the compound is formulated to be administered parenterally, it can be formulated with a pharmaceutically acceptable parenteral carrier.

The present invention can be administered in any convenient formulation form, and the term "formulation" as used herein refers to a dosage form containing a compound of the formula I of the present invention which is advantageous for drug delivery, such as, but not limited to, an aqueous solution injection, powder injection, pill, pulvis, tablet, patch, suppository, emulsion, cream, gel, granule, capsule, aerosol, spray, powder, sustained release agent and controlled release agent. These pharmaceutical auxiliary materials may be conventionally used in various preparations such as, but not limited to, isotonic agents, buffers, flavoring agents, excipients, fillers, binders, disintegrators, lubricants, and the like, or may be selected for use in accordance with the substance, such as: emulsifiers, solubilizers, bacteriostatic agents, analgesics and antioxidants, etc. Such auxiliary materials can effectively improve the stability and solubility of the compounds contained in the composition or change the release rate and absorption rate of the compound, etc., thereby improving the metabolism of the compound of the present invention in vivo, thereby enhancing the administration effect. In addition, auxiliary materials, such as, but not limited to, gelatin, albumin, chitosan, polyethers and polyesters (such as, but not limited to, polyethylene glycol, polyurethane, polycarbonate and copolymers thereof), may be used for achieving specific administration purposes or modes such as sustained release administration, controlled release administration, and pulse administration. The main manifestations of "advantageous drug delivery" are: but not limited to improving the therapeutic effect, improving bioavailability, reducing toxic side effects, and improving patient compliance.

The sixth aspect of the invention provides use of the compound, or pharmaceutically acceptable salt, solvate, optically pure isomer or stereoisomer thereof according to the first aspect, the pharmaceutical mixture according to the fourth aspect or the pharmaceutical composition according to the fifth aspect for the manufacture of a medicament for protecting, handling, treating or ameliorating a disease, disorder or condition of a patient, the disease, disorder or condition is depression, anxiety, Parkinson's disease, Alzheimer's disease, Huntington's disease, schizophrenia, mania, cancer, tumor metastasis, hyperglycemia, hyperlipidemia, viral disorder, bacterial infection, angiogenic disorder, autoimmune disease, inflammatory disorder, a condition associated with organ transplantation.

In another preferred embodiment, the disease, disorder or condition is selected from the group consisting of depression, anxiety, Parkinson's disease, Alzheimer's disease, Huntington's disease, schizophrenia, and mania.

In another preferred embodiment, the disease, disorder or condition is selected from the group consisting of depression, anxiety, Parkinson's disease, Alzheimer's disease, and mania.

In another preferred embodiment, the disease, disorder or condition is depression.

The seventh aspect of the invention provides a method for preventing and/or treating depression, which comprises: administering the compound or the pharmaceutically acceptable salt, solvate, optically pure isomer or stereoisomeric thereof according to the first aspect, the pharmaceutical mixture according to the fourth aspect or the pharmaceutical composition according to the fifth aspect to a subject or patient in need of.

It is to be understood that above each technical feature and each technical feature specifically described hereinafter (as in the examples) within the scope of the present invention may be combined with each other to constitute a new or preferred technical solution. Due to space limitations, those will not be repeated herein.

DESCRIPTION OF EMBODIMENTS

Figure 1:
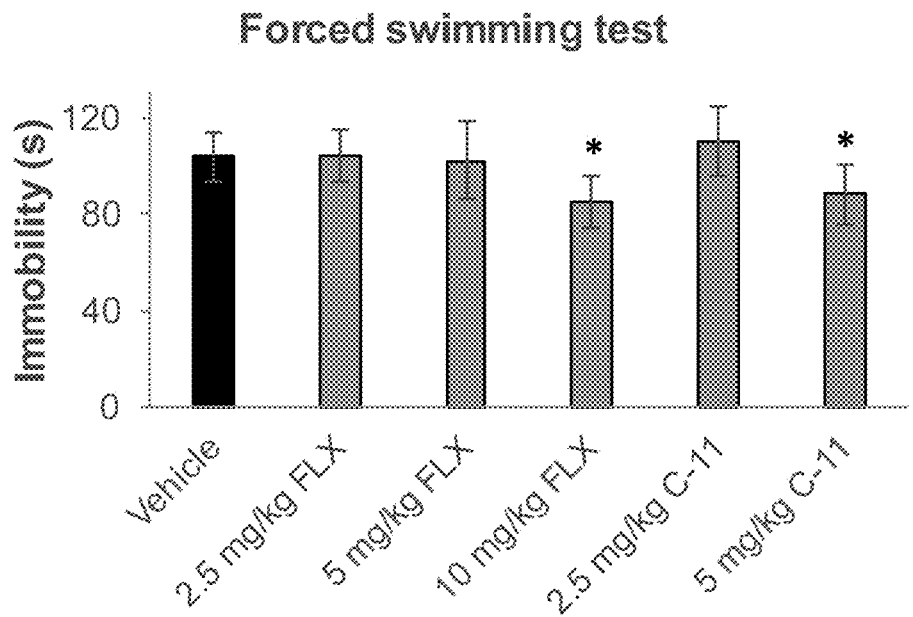
FIG. 1 is a graph showing the effect of gavage administration of example 29 on the immobility time of ICR mouse in forced swimming test ("*" indicates P<0.05; "**" indicates P<0.01).

After extensive and intensive studies, the inventors of the present application have developed structurally novel compounds for the first time, which are formed by linking a urea group and a steroid ligand, and have a structure as shown in formula I. The compounds of the present invention can be used to protect, handle, treat or alleviate various diseases and conditions such as depression. On the basis of this, the present invention has been completed.

The following is a definition of the terms used in this specification. Unless otherwise indicated, the initial definition of a group or term provided herein applies to a group or term that is used alone or as part of another group in the specification.

The term "substituted" means that any of the substituents mentioned in the specification of the invention, including but not limited to, halogen, nitro, cyano, carboxyl, oxo, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, hydroxy, alkoxy, aryloxy, alkanoyloxy, aroyloxy, amino, alkanoylamino, aroylamino, arylalkylacylamino, heteroarylalkylacylamino, aminoalkylacylamino, alkylaminoalkylacylamino, dialkylaminoalkylacylamino, alkylamino, arylamino, arylalkylamino, disubstitutedamino (wherein two substituents on the amino are selected from the group consisting of alkyl, aryl and arylalkyl), alkanoyl, substituted alkanoyl, aroyl, heteroaroyl, carboxyl, alkoxycarbonyl, aryloxycarbonyl, alkylaminocarbonyl, arylaminocarbonyl, arylalkoxycarbonyl, alkylsulfonyl, arylsulfonyl, arylalkylsulfonyl, carbamoyl, substituted carbamoyl, substituted alkylcarbamoyl, amido, substituted amido, sulfonamido, substituted sulfonamide.

The term "halogen" or "halo" refers to fluoro, chloro, bromo, iodo.

The term "alkyl" refers to a straight or branched and unsubstituted hydrocarbyl having 1 to 20 carbon atoms, preferably 1 to 7 carbon atoms. Examples of "alkyl" include, but are not limited to, methyl, ethyl, 1-propyl, 2-propyl, 1-butyl, 2-butyl, and the like.

The term "substituted alkyl" refers to an alkyl group substituted with from 1 to 4 substituents, such as halogen, nitro, cyano, carboxyl, oxo, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, hydroxy, alkoxy, aryloxy, alkanoyloxy, aroyloxy, amino, alkanoylamino, aroylamino, arylalkylacylamino, heteroarylalkylacylamino, aminoalkylacylamino, alkylaminoalkylacylamino, dialkylaminoalkylacylamino, alkylamino, arylamino, arylalkylamino, disubstituted amino (wherein two substituents on the amino are selected from the group consisting of alkyl, aryl and arylalkyl), alkanoyl, substituted alkanoyl, aroyl, heteroaroyl, carboxyl, alkoxycarbonyl, aryloxycarbonyl, alkylaminocarbonyl, arylaminocarbonyl, arylalkoxycarbonyl, alkylsulfonyl, arylsulfonyl, arylalkylsulfonyl, carbamoyl, substituted carbamoyl, substituted alkylcarbamoyl, amido, substituted amido, sulfonamido, substituted sulfonamide.

The term "alkylene" is obtained by removing two hydrogen atoms from a single carbon atom or two carbon atoms of an alkane structure having 1 to 20 carbon atoms, preferably 1 to 7 or 1 to 4 carbon atoms.

The term "alkenyl" refers to a straight or branched hydrocarbyl having from 2 to 20 carbon atoms, preferably from 2 to 15 carbon atoms, most preferably from 2 to 8 carbon atoms, and having from 1 to 4 double bonds.

The term "substituted alkenyl" refers to an alkenyl substituted by 1-2 substituents such as halogen, nitro, cyano, aryl, substituted aryl, heteroaryl, substituted heteroaryl, alkoxy, aryloxy, alkanoyloxy, aroyloxy, amino, alkylamino, arylamino, arylalkylamino, disubstituted amino (wherein two substituents on the amino are selected from the group consisting of alkyl, aryl and arylalkyl).

The term "alkynyl" refers to a straight or branched hydrocarbyl having from 2 to 20 carbon atoms, preferably from 2 to 15 carbon atoms, most preferably from 2 to 8 carbon atoms, and having from 1 to 4 triple bonds.

The term "substituted alkynyl" refers to an alkynyl substituted by a substituent such as halogen, nitro, cyano, aryl, substituted aryl, heteroaryl, substituted heteroaryl, hydroxy, alkoxy, aryloxy, alkanoyloxy, aroyloxy, amino, alkylamino, arylamino, arylalkylamino, disubstituted amino (wherein two substituents on the amino are selected from the group consisting of alkyl, aryl and arylalkyl).

The term "aryl" refers to a monocyclic or bicyclic aromatic hydrocarbyl having from 6 to 12 carbon atoms in the ring portion. The aryl includes a bicyclic group including a ring fused to a saturated or partially unsaturated aromatic ring, or an aromatic carbocycle or heterocycle. Generally, aryl includes, but is not limited to, the following groups: benzene, naphthalene, anthracene, biphenyl, 1,2-dihydronaphthalene, 1,2,3,4-tetrahydronaphthyl, and the like.

The term "substituted aryl" refers to an aryl substituted with from 1 to 4 substituents such as halogen, halogen, nitro, cyano, ureido, carboxyl, trifluoromethoxy, trifluoromethyl, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, hydroxy, alkoxy, aryloxy, alkanoyloxy, aroyloxy, amino, alkylamino, arylamino, arylalkylamino, disubstituted amino (wherein two substituents on the amino are selected from the group consisting of alkyl), aryl and arylalkyl), alkanoyl, substituted alkanoyl, alkoxycarbonyl, arylalkoxycarbonyl, alkylsulfonyl, arylsulfonyl, arylalkylsulfonyl, carbamoyl, substituted carbamoyl, amido, substituted amido, sulfonamido, substituted sulfonamide.

The term "cycloalkyl" refers to a non-aromatic, saturated or partially unsaturated cyclic hydrocarbyl which may be optionally substituted with one or more substituents described herein, which is a monocyclic ring having 3-30 carbon atoms, or a bicyclic or tricyclic ring having 7-12 carbon atoms. Examples of monocyclic cycloalkyl includes, but is not limited to, cyclopropyl, cyclobutyl, cyclopentyl, 1-cyclopent-1-enyl, 1-cyclopent-2-enyl, 1-cyclopenta-3-enyl, cyclohexyl, 1-cyclohex-1-enyl, cycloheptyl, cyclooctyl. Exemplary bridged bicyclic cycloalkyl includes, but is not limited to, bicyclo[2.2.1]heptane, bicyclo[2.2.2]octane, bicyclo[3.2.2]decane, adamantyl.

The term "cycloalkylene" is derived by removing two hydrogen atoms from a single carbon atom or two carbon atoms of a cyclic hydrocarbon structure. The cyclic hydrocarbon has from 3 to 30 carbon atoms, preferably from 3 to 10 carbon atoms including, but not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, cycloheptyl, cyclooctyl, bicyclo[2.2.1]heptane, bicyclo[2.2.2]octane, bicyclo[3.2.2]decane, adamantyl.

The terms "heterocycle", "heterocyclic" and "heterocyclyl" refer to an optionally substituted, fully saturated or unsaturated, aromatic or non-aromatic ring group, for example it may be 4-7 membered monocyclic, 7-11 membered bicyclic or 10-15 membered tricyclic system having at least one heteroatom in at least one ring containing carbon atoms. Each ring of heterocyclyl containing hetero atom may have 1, 2 or 3 hetero atoms selected from N, O and S.

The "heterocyclyl" may be optionally substituted by one or more substituents described herein, and examples of "heterocyclyl" include, but are not limited to, pyrrolidinyl, tetrahydrofuranyl, tetrahydropyranyl, morpholino, thiomorpholino, piperazinyl, homopiperazinyl, epoxypropanyl, imidazolidinyl, 3-azabicyclo[3.1.0]hexanyl, 3-azabicyclo[4.1.0]heptyl, azabicyclo[2.2.2]hexanyl, N-pyridylurea, pyrimidinonyl and 1,1-dioxo-thiomorpholinyl.

The term "heteroaryl" refers to a monovalent aromatic group of a 5-, 6-, 7-, 8, 9, or 10-membered ring, and includes a fused system of 5-20 atoms, containing one or more heteroatoms selected from the group consisting of nitrogen, oxygen, phosphorus and sulfur, which may be optionally substituted by one or more substituents described herein. Examples of "heteroaryl" include, but are not limited to, pyridyl, imidazolyl, imidazopyridyl, pyrimidinyl, pyrazolyl, triazolyl, pyrazinyl, tetrazolyl, furyl, thienyl, thiazolyl, quinolyl, fluorenyl and the like.

The term "oxo" represents a divalent group =O.
The term "carbamoyl" refers to —OC(=O)NH$_2$.
The term "amido" refers to —C(=O)NH$_2$.
The term "sulfonamido" refers to —SO$_2$NH$_2$.
The term "substituted carbamoyl", "substituted amido", "substituted sulfonamido" means that at least one hydrogen of amide, sulfonamide or carbamate is substituted by a substituent selected from the group consisting of alkyl, substituted alkyl, alkenyl, substituted alkenyl, cycloalkyl, substituted cycloalkyl, aryl, substituted aryl, heteroaryl, substituted heteroaryl, heterocyclyl, and substituted heterocyclyl.

The term "acceptable salt" refers to a pharmaceutically acceptable organic or inorganic salt of a compound of the invention. Exemplary salts include, but are not limited to, sulfate, citrate, acetate, oxalate, chloride, bromide, iodide, nitrate, acidic sulfate, ionicotite, lactate, alicylate, acidic citrate, succinate, maleate, fumarate, gluconate, formate, methanesulfonate and pamoate. The "acceptable salt" can involve the inclusion of another molecule such as a maleate or other counterion. The counterion stabilizes the charge in the parent compound. The "acceptable salt" can have more than one charged atom, and a plurality of charged atoms can have multiple counterions.

If the compound of the present invention is a base, the desired "acceptable salt" can be prepared by a suitable method, for example, treating the free base with the following inorganic acid: hydrochloric acid, hydrobromic acid, sulfuric acid, nitric acid, phosphoric acid; or with the following organic acid: acetic acid, maleic acid, succinic acid, mandelic acid, fumaric acid, malonic acid, pyruvic acid, salicylic acid, pyranoside acid such as glucuronic acid or galacturonic acid, α-hydroxy acid such as citric acid or tartaric acid, an amino acid such as glutamic acid, an aromatic acid such as benzoic acid or cinnamic acid, a sulfonic acid such as methanesulfonic acid or p-toluenesulfonic acid.

If the compound of the invention is an acid, the desired "acceptable salt" can be prepared by a suitable method, for example, by treating the free acid with an inorganic base or an organic base: an amine, an alkali metal hydroxide or an alkaline earth metal hydroxide. Illustrative examples of suitable salts include, but are not limited to, organic salts derived from amino acids, salts of primary, secondary, and tertiary amines, and salts of cyclic amines such as piperidine, morpholine, and piperazine, and inorganic salts obtained from sodium, calcium, potassium, magnesium, manganese, iron, copper, zinc, aluminum and lithium.

The term solvate refers to a combination or complex of one or more solvent molecules with a compound of the invention. Examples of solvents that form solvates include, but are not limited to, water, isopropanol, ethanol, methanol, dimethyl sulfoxide, ethyl acetate, acetic acid, and ethanolamine. The compounds of the invention may exist in unsolvated form as well as in solvated forms with pharmaceutically acceptable solvents such as water, ethanol, and the like, so the present invention will include both solvated and unsolvated forms.

The compounds of the invention may contain asymmetric centers or chiral centers, and thus exist in different stereoisomeric forms. All stereoisomeric forms of the compounds of the invention, includes, but are not limited to, diastereomers, enantiomers and hindered isomers, as well as mixtures thereof, such as racemic mixtures, will form part of the present invention. In this context, all stereoisomers are considered when the stereochemistry of any particular chiral atom is not determined. Furthermore, the invention relates to all geometric and positional isomers. The compounds of the invention may exist in different tautomeric forms, and all such forms are contained within the scope of the invention. All stereoisomers of the compounds of the invention are intended to include the form of the mixture or the pure or substantially pure form. Pure optical isomers can be prepared by physical methods such as fractional crystallization, separation or crystallization of diastereomeric derivatives, or by HPLC preparative column, chiral preparative column resolution.

The conditions for the resolution of optical isomers by the HPLC preparation column used in the present invention are as follows:

The analytical chromatographic conditions are as follows:
Column: Waters Xbridge C18 5 um 4.6*250 mm; column temperature 30° C.; flow rate 1 mL/min; mobile phase: acetonitrile (A)—water (B): 86% A-95% A 30 min;

ELSD detector: atomization temperature is 55° C.; carrier gas flow rate: 2.4 L/min.

The chromatographic conditions (1) for preparation are as follows:

Preparative column: US Waters Xbridge C18 5 um 10*250 mm, Waters Xbridge C18 5 um OBD30*150 mm, Waters Xbridge C18 5 um OBD50*150 mm, Waters Xbridge C18 5 um OBD50*250 mm;

The mobile phase: water and acetonitrile, linear gradient elution procedure: 0-30 min, 14% water→5% water; flow rate 3.0 mL/min. The mobile phase is subjected to ultrasonic degassing before use; the injection volume is 800 µl.

Alternatively, the preparative chromatography conditions (2) are as follows:

Preparative column: Daicel chiral preparation column CHIRALPAK AD-H 5 um 20*250 mm, CHIRALPAK AD-H 5 um 30*250 mm, CHIRALPAK AD 5 um 20*250 mm, CHIRALPAK AS-H 5 um 20*250 mm, CHIRALCEL OD-H 5 um 20*250 mm, The mobile phase is n-hexane and isopropanol at a flow rate of 3.0 mL/min.

The mobile phase is subjected to ultrasonic degassing before use; the injection volume is 600 µl.

The above-mentioned features in the present invention, or the features mentioned in the embodiments, may be arbitrarily combined. All of the features disclosed in the present specification can be used in any combination, and the various features disclosed in the specification can be replaced by any alternative feature that provides the same, equal or similar purpose. Therefore, unless otherwise stated, the disclosed features are only general examples of equal or similar features.

The invention is further illustrated below in conjunction with specific embodiments. It is to be understood that the examples are used only to illustrate the invention and not intended to limit the scope of the invention. The experimental methods in the following examples which do not specify the specific conditions are usually carried out according to the conventional conditions such as the conditions described in Sambrook et al., Molecular Cloning: Laboratory Manual (New York: Cold Spring Harbor Laboratory Press, 1989), or according to the conditions suggested by the manufacturer. Unless otherwise stated, percentages and parts are percentages by weight and parts by weight, all temperatures are given in degrees Celsius, reagents are purchased from commercial suppliers or customized, such as Sinopharm, Shaoyuan, Energy Chemical, TCI, Sigma, and the like.

Unless otherwise defined, all professional and scientific terms used herein have the same meaning as those well known by the skilled in the art. In addition, any methods and materials similar or equivalent to those described may be employed in the methods of the invention. The preferred embodiments and materials described herein are for illustrative purposes only.

Example 1

Preparation of 3α-Amino Sarsasapogenin

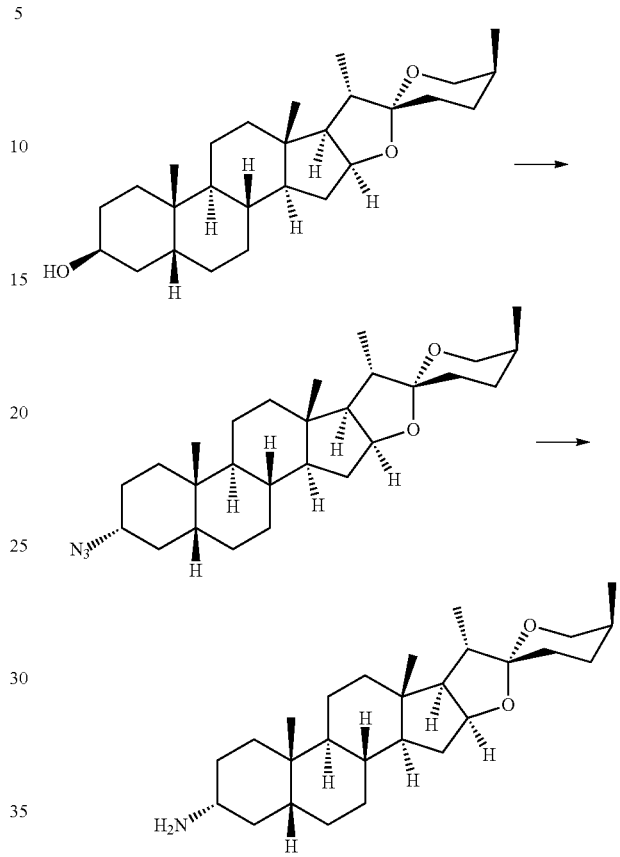

1.2 g of sarsasapogenin was weighed, dissolved in 30 ml of DCM, and 2 ml of pyridine was added thereto, followed by being stirred at room temperature. Under ice-cooling condition, 0.5 ml of methanesulfonyl chloride was slowly added dropwise. After the addition was completed, the mixture was stirred for another 0.5 h under ice-bath condition, and then slowly warmed to room temperature and reacted for 4 hours. The ice water was added to the reaction liquid and stirred for 30 min. The reaction liquid was extracted with DCM and the combined organic phase was dried over anhydrous sodium sulfate. 1 g of the product was obtained by silica gel column chromatography and then redissolved in 40 ml of DMF, and 800 mg of NaN$_3$ was added thereto, and the mixture was stirred at 60° C. for 12 hours. After the mixture was cooled to room temperature, ice water was added and stirred for 30 min, and a white solid was precipitated, filtered, washed with water, and dried, and then subjected to silica gel column chromatography to obtain 550 mg of 3α-azido sarsasapogenin which was then dissolved in 20 ml of THF/2 ml of water. 600 mg of triphenylphosphine was added to the solution and the mixture was stirred at 60° C. overnight. The solvent was removed under reduced pressure and the residue was purified by silica gel column chromatography to afford 350 mg of 3α-amino sarsasapogenin.

$^1$H NMR (300 MHz, CDCl$_3$): 4.40 (1H, dd, J=6.0, 12.0 Hz, H-16), 3.95 (1H, dd, J=3.0, 9.0 Hz, H-26a), 2.70 (1H, m, H-3), 3.30 (1H, d, J=6.0 Hz, H-26b), 1.08 (3H, d, J=6.0 Hz, H-21), 0.99 (3H, d, J=6.0 Hz, H-27), 0.93 (3H, s, H-19), 0.75

(3H, s, H-18). $^{13}$C NMR (300 MHz, CDCl$_3$): δ 157.3 (C=O), 109.8 (C-22), 81.1 (C-16), 65.2 (C-26), 62.1 (C-17), 56.6 (C-14), 51.5 (C-3), 42.5 (C-5), 42.2 (C-20), 40.7 (C-13), 40.6 (C-9), 40.4 (C-12), 37.6 (C-4), 36.2 (C-1), 35.6 (C-8), 34.8 (C-10), 31.8 (C-15), 31.4 (C-2), 27.3 (C-6), 27.2 (C-23), 26.8 (C-7), 26.0 (C-25), 25.9 (C-24), 23.7 (C-19), 20.7 (C-11), 16.6 (C-18), 16.2 (C-27), 14.4 (C-21). LC-MS, calculated (C$_{27}$H$_{45}$NO$_2$, M) 415.3450, found [M+H]$^+$: 416.3528.

Example 2

Preparation of 3β-Amino Sarsasapogenin

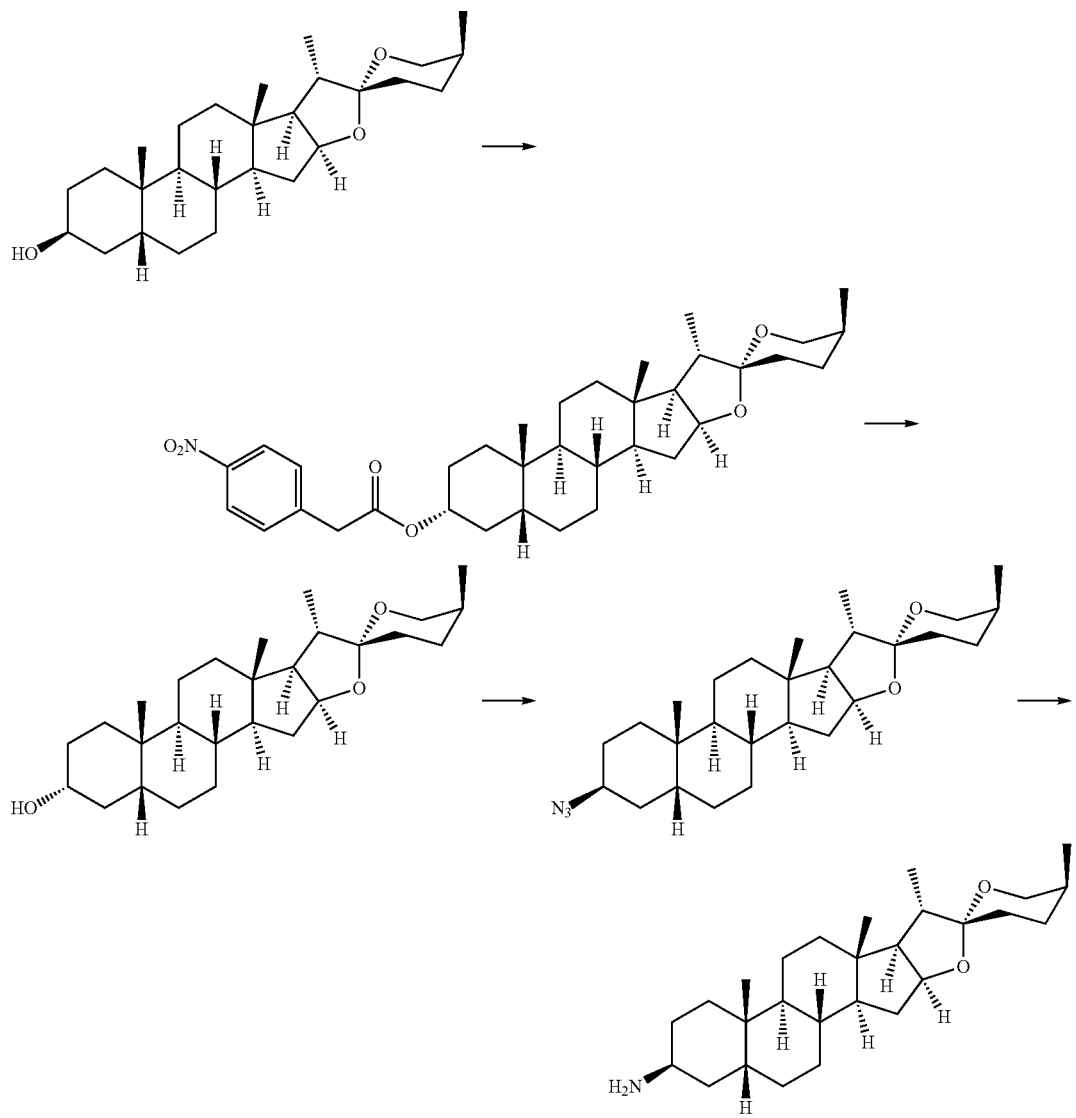

3 g of sarsasapogenin was weighed and dissolved in 80 ml of THF, 2.6 g of triphenylphosphine was added, then 4.3 ml of DIAD was added, and 1.6 g of p-nitrophenylacetic acid was finally added, and the mixture was stirred at room temperature overnight. The solvent was removed under reduced pressure and the residue was purified by silica gel column chromatography to afford 1.2 g of the product. The product was redissolved in 20 ml of THF/5 ml of H$_2$O, and 400 mg of sodium hydroxide was added thereto, and the mixture was stirred at room temperature overnight. The solvent was removed under reduced pressure, and DCM and water were added. The DCM layer was removed and the aqueous lay was extracted with DCM. The combined organic phase was washed with 1M hydrochloric acid, saturated sodium bicarbonate solution, and saturated sodium chloride solution, dried over anhydrous sodium sulfate and subjected to silica gel column chromatography (eluent P/E=5:1) to obtain 3α-hydroxy sarsasapogenin. The data are as follows:

$^1$H NMR (300 MHz, CDCl$_3$): 4.40 (1H, dd, J=6.0, 12.0 Hz, H-16), 3.95 (1H, dd, J=3.0, 9.0 Hz, H-26a), 2.70 (1H, m, H-3), 3.30 (1H, d, J=6.0 Hz, H-26b), 1.08 (3H, d, J=6.0 Hz, H-21), 0.99 (3H, d, J=6.0 Hz, H-27), 0.93 (3H, s, H-19), 0.75 (3H, s, H-18). $^{13}$C NMR (300 MHz, CDCl$_3$): δ 157.3 (C=O), 109.8 (C-22), 81.1 (C-16), 65.2 (C-26), 62.2 (C-17), 56.5 (C-14), 71.8 (C-3), 42.2 (C-5), 42.1 (C-20), 40.7 (C-13), 40.6 (C-9), 40.4 (C-12), 36.5 (C-4), 35.5 (C-1), 35.6 (C-8), 34.8 (C-10), 31.9 (C-15), 30.6 (C-2), 27.3 (C-6), 27.2 (C-23), 26.8 (C-7), 26.0 (C-25), 25.9 (C-24), 23.5

(C-19), 20.7 (C-11), 16.6 (C-18), 16.2 (C-27), 14.4 (C-21). LC-MS, calculated (C$_{27}$H$_{44}$O$_3$, M) 416.3290, found [M+H]$^+$: 417.3334.

1.2 g of sarsasapogenin was weighed, dissolved in 30 ml of DCM, and 2 ml of pyridine was added thereto, followed by being stirred at room temperature. Under ice-cooling condition, 0.5 ml of methanesulfonyl chloride was slowly added dropwise. After the addition was completed, the mixture was stirred for another 0.5 h under ice-bath condition, and then slowly warmed to room temperature and reacted for 4 hours. The ice water was added to the reaction liquid and stirred for 30 min. The reaction liquid was extracted with DCM and the combined organic phase was dried over anhydrous sodium sulfate, subjected to silica gel column chromatography to obtain 900 mg product. Then the product was redissolved in 40 ml of DMF, and 800 mg of NaN$_3$ was added thereto, and the mixture was stirred at 60° C. for 12 hours. After the mixture was cooled to room temperature, ice water was added and stirred for 30 min, and a white solid was precipitated, filtered, washed with water, dried, and then subjected to silica gel column chromatography to obtain 450 mg of 3β-azido sarsasapogenin which was then dissolved in 20 ml of THF/2 ml of water, and 600 mg of triphenylphosphine was added thereto, and the mixture was stirred at 60° C. overnight. The solvent was removed under reduced pressure, and the residue was purified by silica gel column chromatography to afford 250 mg of 3β-amino sarsasapogenin.

Example 3

Preparation of 3-Amino Sarsasapogenin (Mixture)

1 g of sarsasapogenin was weighed, dissolved in 20 ml of anhydrous DCM, and 800 g of PCC was slowly added under ice-cooling condition, and then the mixture was slowly warmed to room temperature and reacted. The TLC dot-plate was used to track the complete of the reaction. DCM and water were added to the reaction system, and several layers were separated. The aqueous layer was extracted with DCM, and the combined organic layer was washed with water, dried over anhydrous sodium sulfate, evaporated to remove solvent under reduced pressure and separated by silica gel column chromatography to give 790 mg of oxidation product of sarsasapogenin.

700 mg of oxidation product was weighed, dissolved in 40 ml of anhydrous methanol, and 1.3 g of ammonium acetate was added thereto. The mixture was stirred at room temperature for 1 hour, and 120 mg of sodium cyanoborohydride was added thereto, and the mixture was stirred for 24 hours. The TLC dot-plate was used to track the complete of the reaction. The solvent was evaporated under reduced pressure. DCM and water were added to the residue. The organic layer was removed and the aqueous lay was extracted with DCM. The combined organic phase was washed with aqueous NaOH solution, saturated sodium chloride solution, and dried over anhydrous sodium sulfate. The organic solvent was removed under reduced pressure. The crude product was subjected to silica gel column chromatography to give 350 mg of product as a mixture of the diastereomers 3α-amino sarsasapogenin and 3β-amino sarsasapogenin.

Example 4

Preparation of Optically Pure 3α-Amino Sarsasapogenin and 3β-Amino Sarsasapogenin by the Resolution of 3-Amino Sarsasapogenin (Mixture) of Example 3 by HPLC Preparation Column

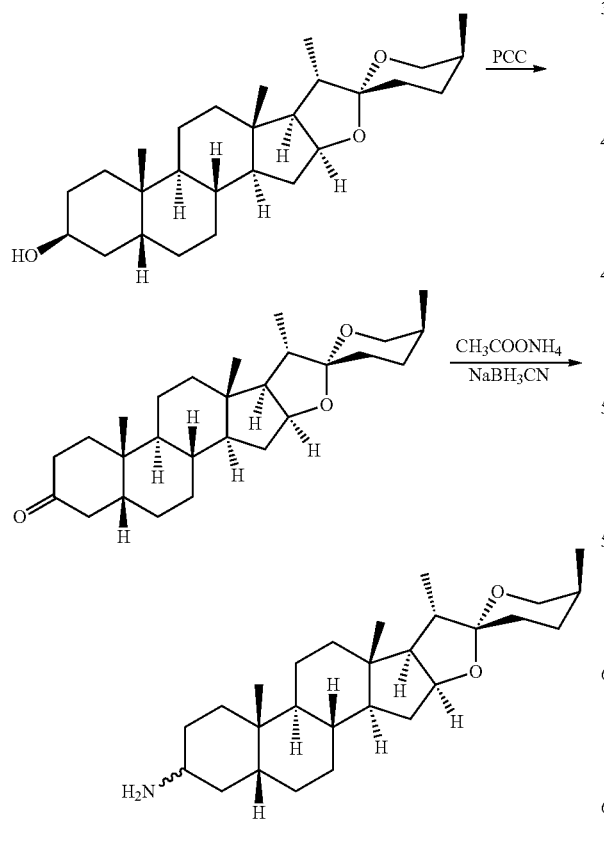

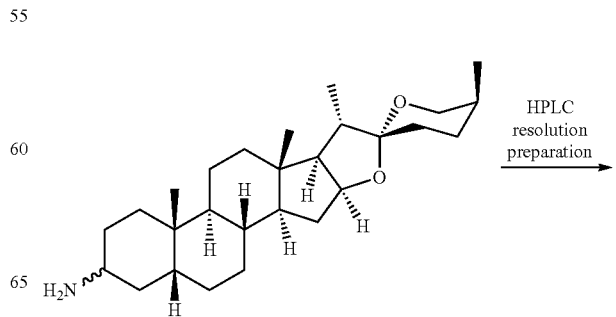

-continued

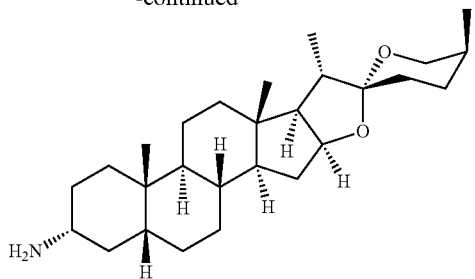

+

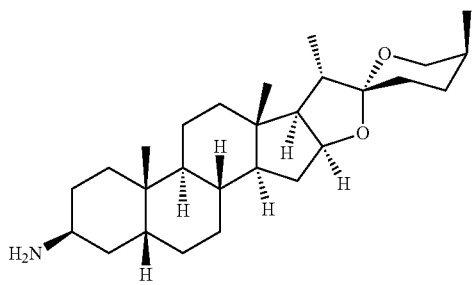

350 mg 3-amino sarsasapogenin (mixture) obtained by silica gel column chromatography in example 3 was subjected to resolution by HPLC preparation column to give optically pure isomer, 150 mg of 3α-amino sarsasapogenin and 130 mg of 3β-amino sarsasapogenin.

Example 5

Preparation of Compound C-1

740 mg of triphosgene was weighed and dissolved in 20 ml of DCM. 1.0 g of 3α-amino sarsasapogenin was dissolved in 20 ml of DCM, and then slowly added dropwise into the reaction system. 0.76 ml of triethylamine was dissolved in 20 ml of DCM, and then slowly added dropwise into the reaction system. The solvent was evaporated under reduced pressure, and the residue was separated by column chromatography to obtain 1.0 g of compound.

$^1$H NMR (300 MHz, CDCl$_3$): 4.40 (1H, dd, J=6.0, 9.0 Hz, H-16), 3.95 (1H, dd, J=3.0, 9.0 Hz, H-26a), 3.49 (1H, m, H-3), 3.68 (1H, m, H-3', 5'), 3.31 (1H, m, H-2', 6'), 3.31 (1H, d, J=9.0 Hz, H-26b), 1.08 (3H, d, J=6.0 Hz, H-21), 0.99 (3H, d, J=6.0 Hz, H-27), 0.95 (3H, s, H-19), 0.75 (3H, s, H-18). $^{13}$C NMR (300 MHz, CDCl$_3$): δ 157.3 (C=O), 109.8 (C-22), 81.1 (C-16), 66.6 (C-3', C-5'), 65.2 (C-26), 62.2 (C-17), 56.6 (C-14), 50.7 (C-3), 44.1 (C-2', C-6'), 42.5 (C-5), 42.2 (C-20), 40.8 (C-9), 40.7 (C-13), 40.4 (C-12), 36.1 (C-4), 35.5 (C-8), 34.8 (C-1), 34.5 (C-10), 31.8 (C-15), 28.7 (C-2), 27.0 (C-6), 27.1 (C-23), 26.8 (C-7), 26.0 (C-25), 25.8 (C-24), 23.6 (C-19), 20.7 (C-11), 16.6 (C-18), 16.1 (C-27), 14.4 (C-21). LC-MS, calculated (C$_{32}$H$_2$N$_2$O$_4$, M) 528.3927, found [M+H]$^+$: 529.3979.

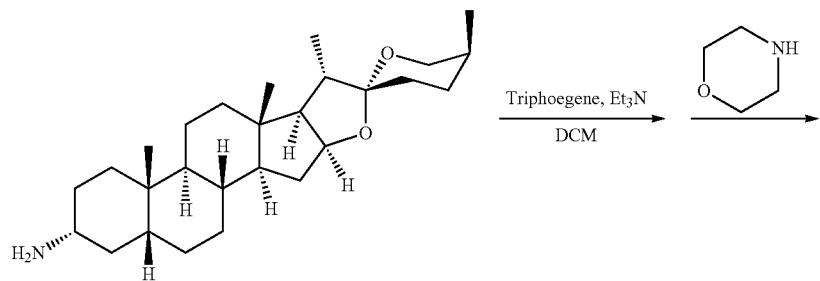

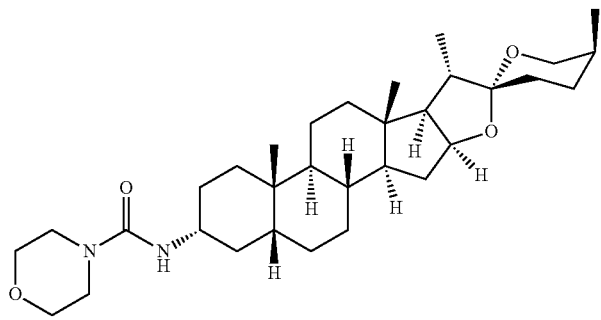

Example 6

Preparation of Compound C-1 and Compound C-2 by HPLC Preparation Column Resolution

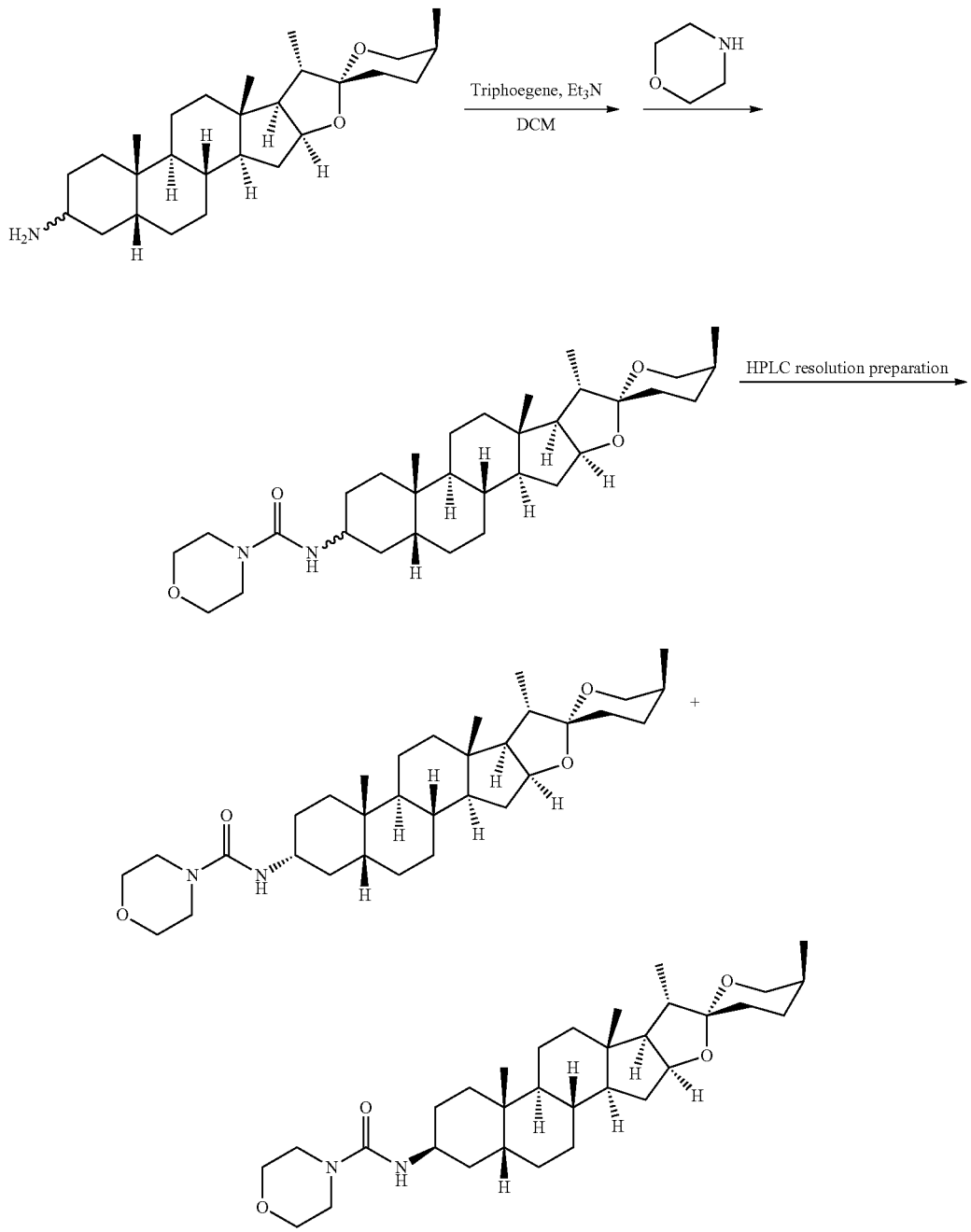

75 mg of triphosgene was weight and dissolved in 2 ml of DCM. 100 mg of 3-amino sarsasapogenin (a mixture of a conformation and p conformation) was dissolved in 2 ml of DCM, and then slowly added dropwise into the reaction system. 80 μl of triethylamine was dissolved in 2 ml of DCM and then slowly added dropwise into the reaction system, and the solvent was evaporated under reduced pressure. The residue was dissolved in 3 ml of DCM. A solution of 30 μl amine II in 30 ml of DCM was added dropwise to the reaction solution, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography, and then subjected to the resolution by HPLC preparation column to obtain a pure optical isomer, wherein compound C-1 is 35 mg and compound C-2 is 30 mg. The 3-aminosarsasapogenin used (a mixture of alpha conformation and beta conformation) was prepared in example 3.

Example 7

Preparation of Compound C-3

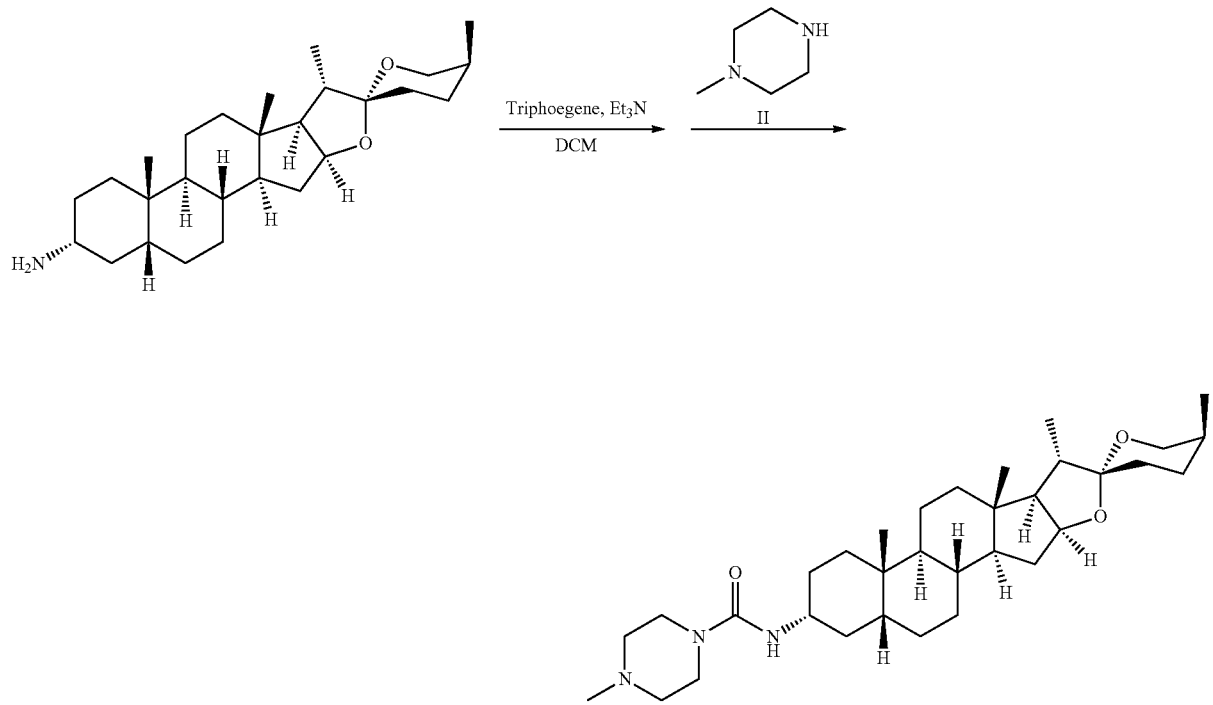

720 mg of triphosgene was dissolved in 20 ml of DCM, and 1.0 g of 3α-amino sarsasapogenin was dissolved in 20 ml of DCM, and then slowly added dropwise into the reaction system. 0.74 ml of triethylamine was dissolved in 20 ml of DCM, and then slowly added dropwise into the reaction system. The solvent was evaporated under reduced pressure and the residue was dissolved in 30 ml of DCM. A solution of 0.27 ml amine II in 30 ml of DCM was slowly added dropwise into the reaction system, and the solvent was evaporated under reduced pressure. The residue was separated by column chromatography to give 750 mg of compound 2. LC-MS, calculated ($C_{33}H_{55}N_3O_3$, M) 541.4243, found [M+H]$^+$: 542.4307.

Example 8

Preparation of Compound C-3 and Compound C-4 by HPLC Preparation Column Resolution

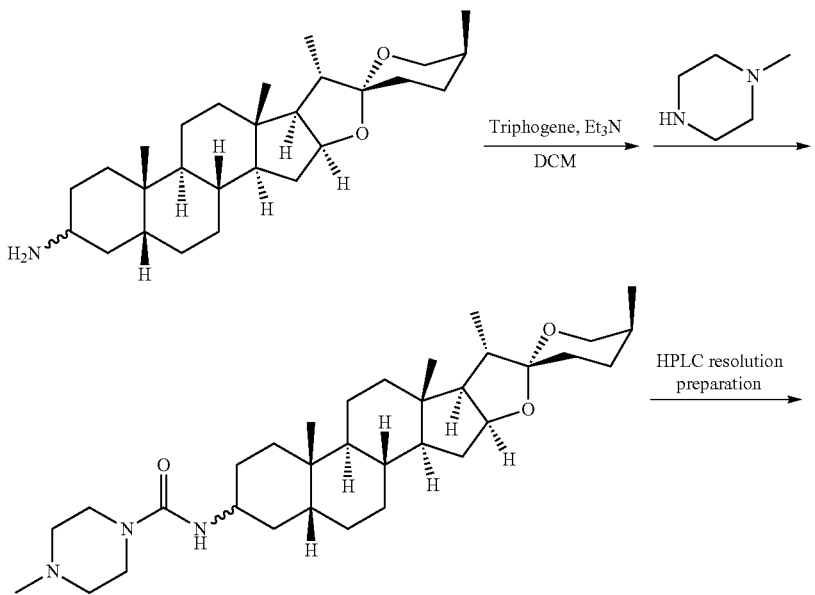

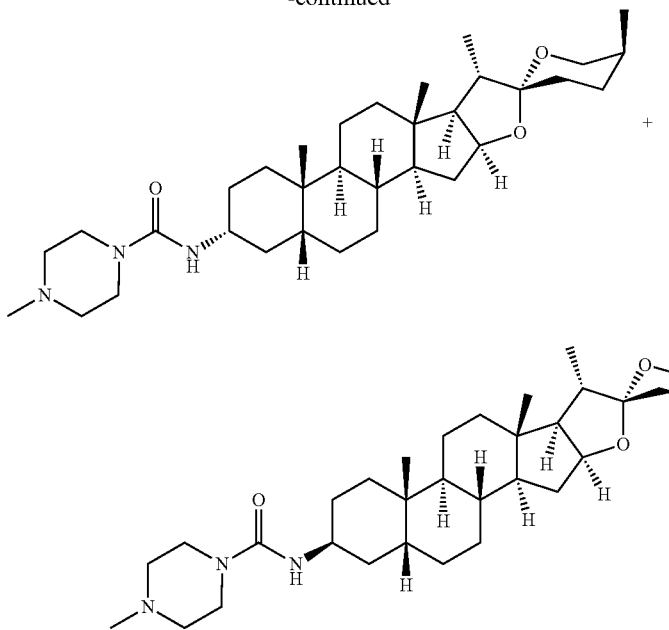

75 mg of triphosgene was dissolved in 2 ml of DCM, and 100 mg of 3-amino sarsasapogenin (a mixture of a conformation and p conformation) was dissolved in 2 ml of DCM, and then slowly added dropwise into the reaction system. 80 µl of triethylamine was dissolved in 2 ml of DCM and then slowly added dropwise into the reaction system, and the solvent was evaporated under reduced pressure. The residue was dissolved in 3 ml of DCM. A solution of 40 µl amine II in 3 ml of DCM was added dropwise to the reaction solution, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography, and then subjected to the resolution by HPLC preparation column to obtain a pure optical isomer, wherein compound C-3 is 30 mg and compound C-4 is 25 mg. The 3-amino sarsasapogenin used (a mixture of alpha conformation and beta conformation) was prepared in example 3.

Example 9

Preparation of Compound C-7

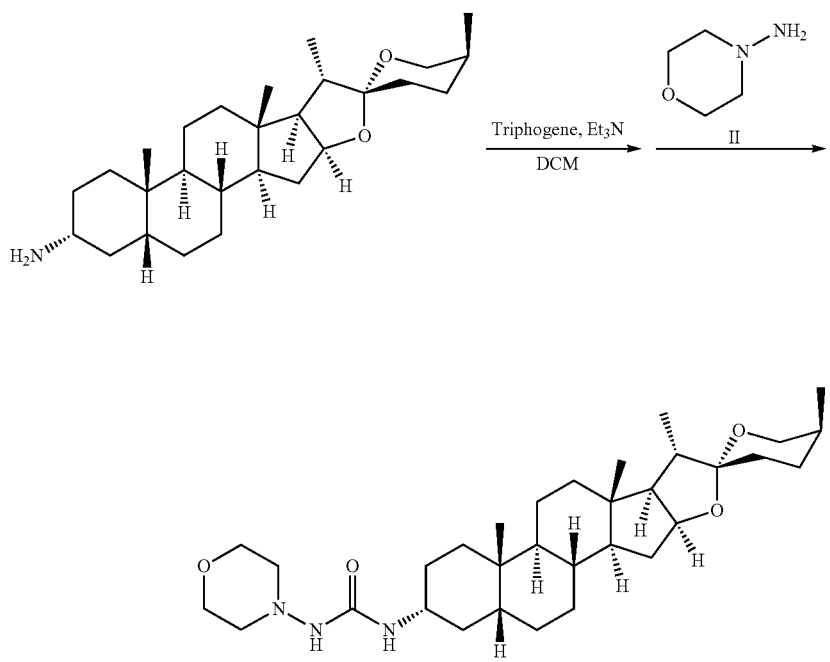

840 mg of triphosgene was dissolved in 20 ml of DCM, and 1.2 g of 3α-amino sarsasapogenin was dissolved in 20 ml of DCM, and then slowly added dropwise into the reaction system. 0.85 ml of triethylamine was dissolved in 20 ml of DCM, and then slowly added dropwise into the reaction system. The solvent was evaporated under reduced pressure and the residue was dissolved in 50 ml of DCM. A solution of 0.28 ml amine II in 30 ml of DCM was slowly added dropwise into the reaction system, and the solvent was evaporated under reduced pressure. The residue was separated by column chromatography to give 890 mg of compound C-7. LC-MS, calculated ($C_{32}H_{53}N_3O_4$, M) 543.4036, found $[M+H]^+$: 544.4190.

Example 10

Preparation of Compound C-9

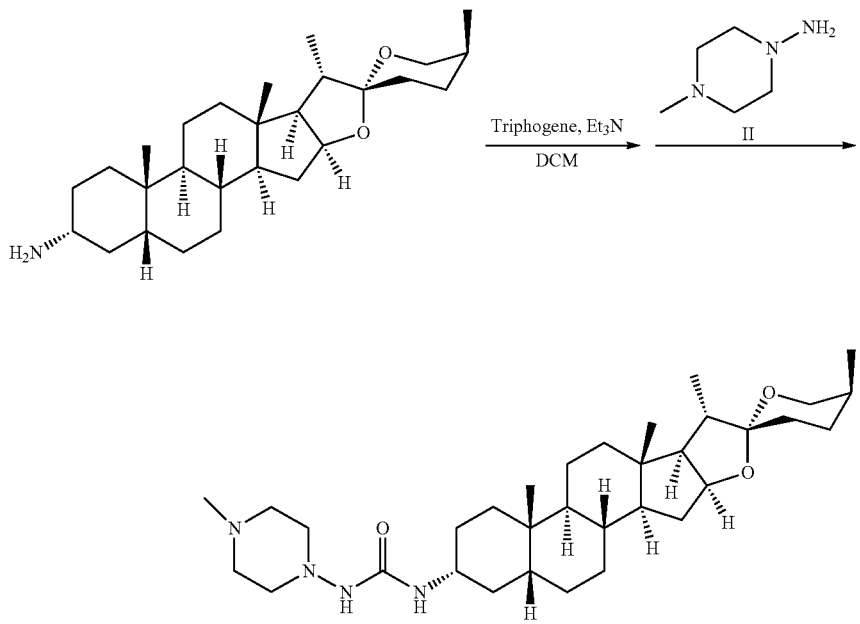

615 mg of triphosgene was dissolved in 20 ml of DCM, and 860 mg of 3α-amino sarsasapogenin was dissolved in 20 ml of DCM, and then slowly added dropwise into the reaction system. 0.64 ml of triethylamine was dissolved in 20 ml of DCM, and then slowly added dropwise into the reaction system. The solvent was evaporated under reduced pressure and the residue was dissolved in 50 ml of DCM. A solution of 0.25 ml amine II in 30 ml of DCM was slowly added dropwise into the reaction system, and the solvent was evaporated under reduced pressure. The residue was separated by column chromatography to give 480 mg of compound C-9. LC-MS, calculated ($C_{33}H_{56}N_4O_3$, M) 556.4352, found $[M+H]^+$: 557.4420.

Example 11

Preparation of compound C-9 and compound C-10 by HPLC preparation column resolution

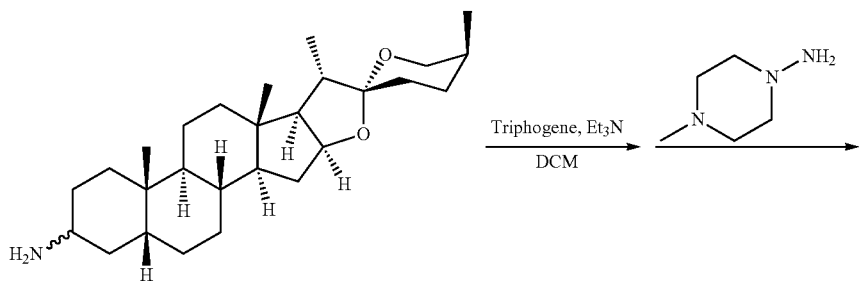

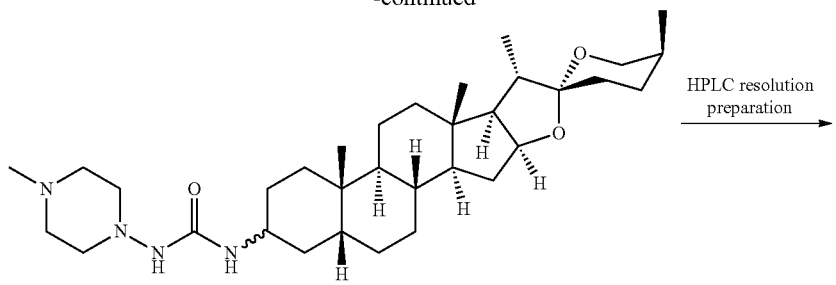

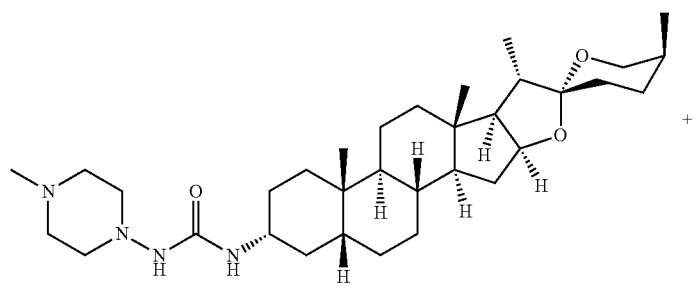

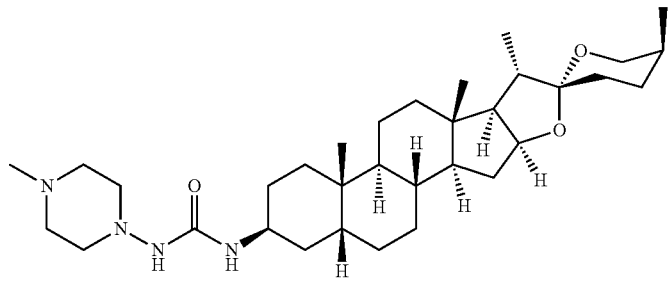

65 mg of triphosgene was dissolved in 20 ml of DCM, and 85 mg of 3-amino sarsasapogenin (a mixture of a conformation and p conformation) was dissolved in 2 ml of DCM, and then slowly added dropwise into the reaction system. 65 µl of triethylamine was dissolved in 20 ml of DCM and then slowly added dropwise into the reaction system, and the solvent was evaporated under reduced pressure. The residue was dissolved in 5 ml of DCM. A solution of 30 µl amine II in 3 ml of DCM was added dropwise to the reaction solution, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography, and then subjected to the resolution by HPLC preparation column to obtain a pure optical isomer, wherein compound C-9 is 20 mg and compound C-10 is 15 mg. The 3-amino sarsasapogenin used (a mixture of alpha conformation and beta conformation) was prepared in example 3.

Example 12

Preparation of Compound C-5

-continued
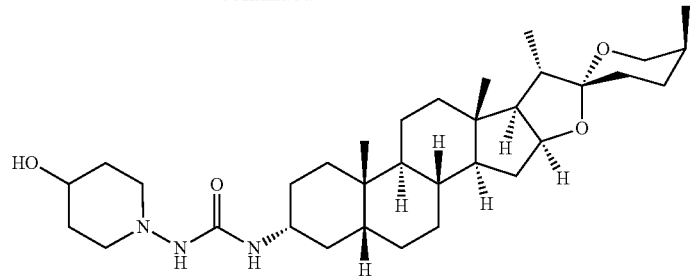
The preparation method was the same as the preparation method of compound C-7 in example 9. LC-MS, calculated ($C_{34}H_{56}N_2O_4$, M) 556.4240, found [M+H]$^+$: 557.4298.
Example 13
Preparation of Compound C-6
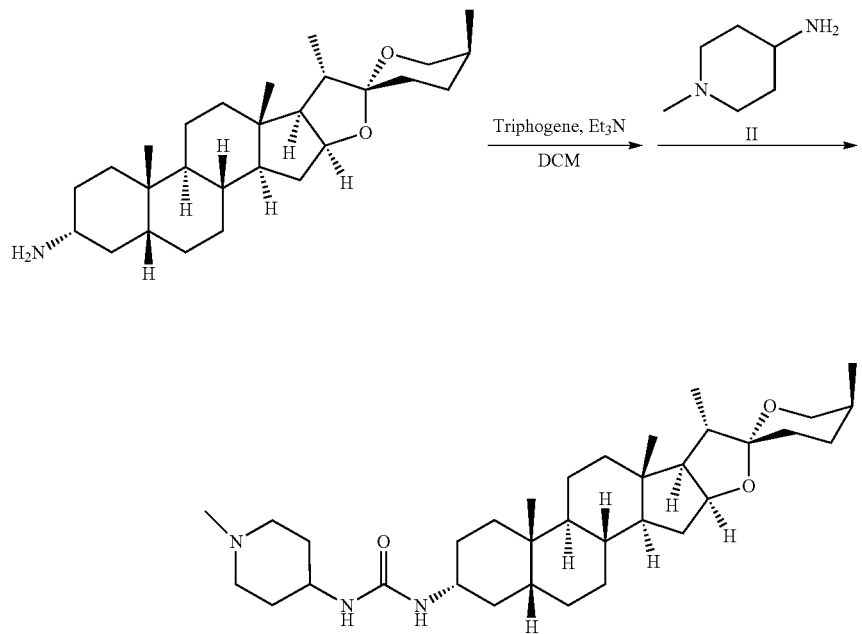
The preparation method was the same as the preparation method of compound C-7 in example 9. LC-MS, calculated ($C_{34}H_{57}N_3O_3$, M) 555.4400, found [M+H]$^+$: 556.4473.
Example 14
Preparation of Compound C-13
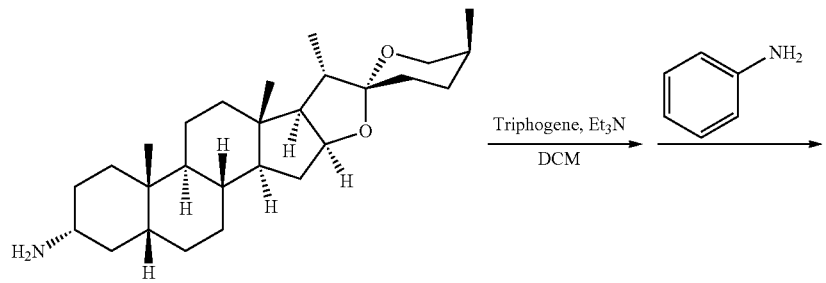

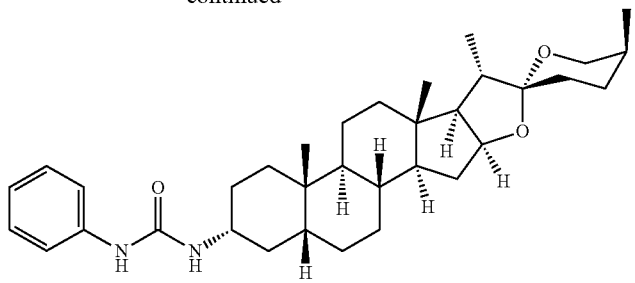

2.8 g of triphosgene was dissolved in 90 ml of DCM, and 3.9 g of 3α-amino sarsasapogenin was dissolved in 60 ml of DCM, and then slowly added dropwise into the reaction system. Triethylamine (2.2 eq) was dissolved in 60 ml of DCM, and then slowly added dropwise into the reaction system. The solvent was evaporated under reduced pressure and the residue was dissolved in 120 ml of DCM. A solution of aniline (2 eq) in 120 ml THF was slowly added dropwise into the reaction system. DCM was added to dilute the reaction solution. The mixture was washed with 1M hydrochloric acid, saturated sodium bicarbonate solution, and saturated sodium chloride solution, dried over anhydrous sodium sulfate and separated by silica gel column chromatography to give 2.5 g of compound C-13.

$^1$H NMR (300 MHz, CDCl$_3$): 7.30 (2H, m, H-2', H-6'), 7.25 (2H, m, H-3', H-5'), 7.01 (1H, d, J=6.0 Hz, H-4'), 4.40 (1H, dd, J=6.0, 9.0 Hz, H-16), 3.95 (1H, dd, J=3.0, 9.0 Hz, H-26a), 3.61 (1H, m, H-3), 3.30 (1H, d, J=9.0 Hz, H-26b), 1.08 (3H, d, J=6.0 Hz, H-21), 1.00 (3H, d, J=6.0 Hz, H-27), 0.89 (3H, s, H-19), 0.74 (3H, s, H-18). $^{13}$C NMR (300 MHz, CDCl$_3$): δ155.8 (C=O), 132.9 (C-1'), 120.4 (C-2', C-6'), 129.3 (C-3', C-5'), 123.3 (C-4'), 109.9 (C-22), 81.2 (C-16), 65.3 (C-26), 62.2 (C-17), 56.4 (C-14), 50.4 (C-3), 42.5 (C-5), 42.2 (C-20), 40.7 (C-9), 40.7 (C-13), 40.3 (C-12), 36.1 (C-4), 35.5 (C-8), 34.8 (C-1), 34.4 (C-10), 31.9 (C-15), 28.6 (C-2), 27.2 (C-6), 27.1 (C-23), 26.8 (C-7), 26.1 (C-25), 25.9 (C-24), 23.7 (C-19), 20.7 (C-11), 16.6 (C-18), 16.2 (C-27), 14.5 (C-21). LC-MS, calculated (C$_{34}$H$_{50}$N$_2$O$_3$, M) 534.3821, found [M+H]$^+$: 535.3879.

Example 15

Preparation of Compound C-13 and Compound C-14 by HPLC Preparation Column Resolution

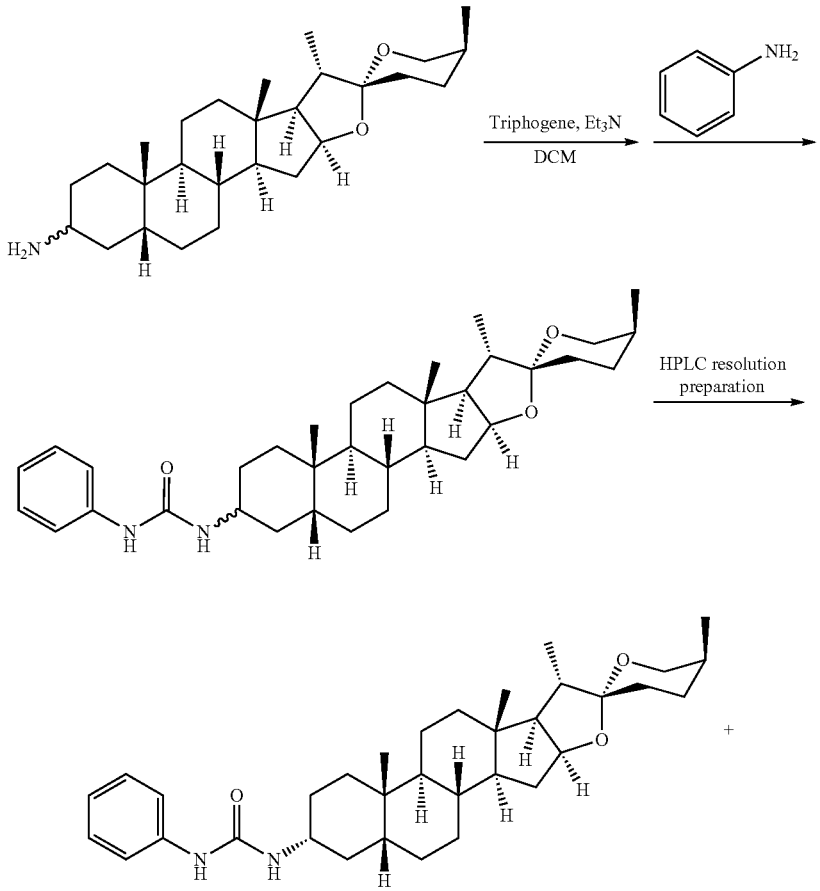

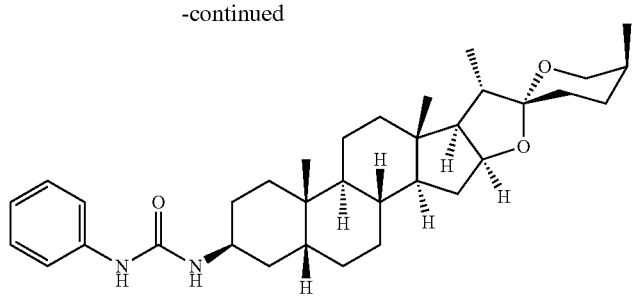

300 mg of triphosgene was dissolved in 10 ml of DCM, and 400 mg of 3-amino sarsasapogenin (a mixture of two conformations) was dissolved in 10 ml of DCM, and then slowly added dropwise into the reaction system. 2.2 equivalent of triethylamine was dissolved in 10 ml of DCM and then slowly added dropwise into the reaction system, and the solvent was evaporated under reduced pressure. The residue was dissolved in 30 ml of DCM. A solution of 2 equivalent of aniline in 20 ml of THF was added dropwise to the reaction solution, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography, and then subjected to the resolution by HPLC preparation column to obtain a pure optical isomer, wherein compound C-13 is 90 mg and compound C-14 is 80 mg. The 3-amino sarsasapogenin used (a mixture of alpha conformation and beta conformation) was prepared in example 3.

Example 16

Preparation of Compound C-15

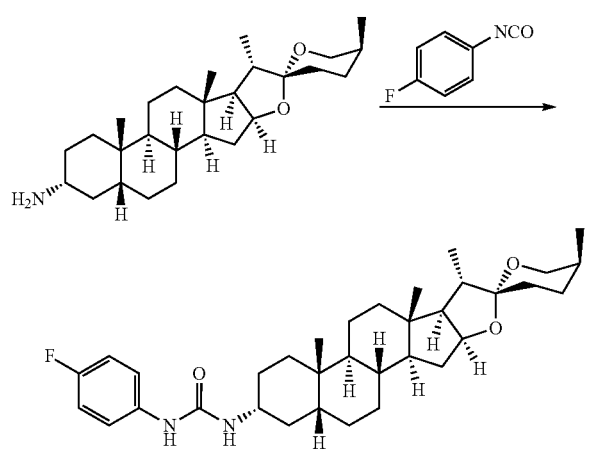

1 g of 3α-amino sarsasapogenin was dissolved in 80 ml of DCM, 0.7 ml of 4-fluorophenylisocyanate and 0.33 ml of triethylamine were added, and the mixture was stirred at room temperature overnight. The reaction mixture was diluted with DCM, washed with 1M hydrochloric acid, saturated sodium bicarbonate solution, and saturated sodium chloride solution, dried over anhydrous sodium sulfate, and separated by silica gel column chromatography (eluent P/E=3:1) to give 720 mg of compound C-15.

$^1$H NMR (300 MHz, CDCl$_3$): 7.23 (2H, m, H-2', H-6'), 6.93 (2H, t, J=6.0 Hz, H-3', H-5'), 4.40 (1H, dd, J=6.0, 9.0 Hz, H-16), 3.95 (1H, dd, J=3.0, 9.0 Hz, H-26a), 3.58 (1H, m, H-3), 3.30 (1H, d, J=9.0 Hz, H-26b), 1.08 (3H, d, J=3.0 Hz, H-21), 1.00 (3H, d, J=6.0 Hz, H-27), 0.90 (3H, s, H-19), 0.74 (3H, s, H-18). $^{13}$C NMR (300 MHz, CDCl$_3$): δ162.2 (C-4'), 157.8 (C=O), 135.1 (C-1'), 122.2 (C-2', C-6'), 115.9 (C-3', C-5'), 109.9 (C-22), 81.1 (C-16), 65.3 (C-26), 62.2 (C-17), 56.5 (C-14), 50.5 (C-3), 42.5 (C-5), 42.2 (C-20), 40.7 (C-9), 40.8 (C-13), 40.3 (C-12), 36.1 (C-4), 35.5 (C-8), 34.8 (C-1), 34.4 (C-10), 31.8 (C-15), 28.6 (C-2), 27.2 (C-6), 27.1 (C-23), 26.8 (C-7), 26.1 (C-25), 25.9 (C-24), 23.7 (C-19), 20.7 (C-11), 16.6 (C-18), 16.2 (C-27), 14.5 (C-21). LC-MS, calculated (C$_{34}$H$_{49}$FN$_2$O$_3$, M) 为 552.3727, found [M+H]$^+$: 553.3779.

Example 17

Preparation of Compound C-16

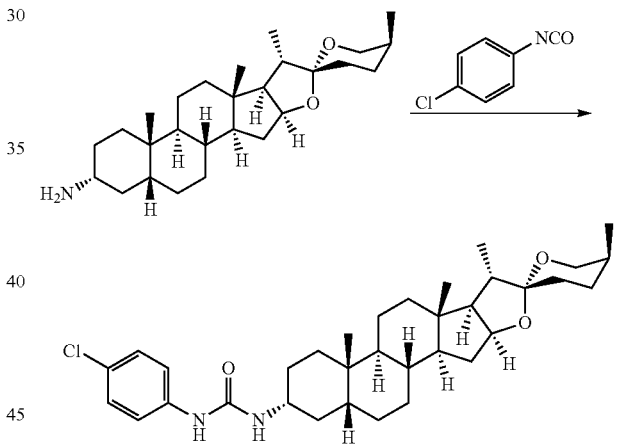

1 g of 3α-amino sarsasapogenin was dissolved in 80 ml of DCM, 0.7 ml of 4-chlorophenylisocyanate and 0.33 ml of triethylamine were added, and the mixture was stirred at room temperature overnight. The reaction mixture was diluted with DCM, washed with 1M hydrochloric acid, saturated sodium bicarbonate solution, and saturated sodium chloride solution, dried over anhydrous sodium sulfate, and separated by silica gel column chromatography (eluent P/E=3:1) to give 1.1 g of compound C-16.

$^1$H NMR (300 MHz, CDCl$_3$): δ7.23 (2H, m, H-3', H-5'), 7.20 (2H, m, H-2', H-6'), 4.40 (1H, dd, J=6.0, 12.0 Hz, H-16), 3.95 (1H, dd, J=3.0, 9.0 Hz, H-26a), 3.58 (1H, m, H-3), 3.31 (1H, d, J=6.0 Hz, H-26b), 1.08 (3H, d, J=3.0 Hz, H-21), 1.00 (3H, d, J=6.0 Hz, H-27), 0.90 (3H, s, H-19), 0.74 (3H, s, H-18). $^{13}$C NMR (300 MHz, CDCl$_3$): δ155.5 (C=O), 137.8 (C-1'), 129.2 (C-3', C-5'), 128.2 (C-4'), 121.2 (C-2', C-6'), 110.0 (C-22), 81.2 (C-16), 65.4 (C-26), 62.2 (C-17), 56.5 (C-14), 50.5 (C-3), 42.5 (C-5), 42.2 (C-20), 40.8 (C-9), 40.8 (C-13), 40.4 (C-12), 36.1 (C-4), 35.5 (C-8), 34.8 (C-1), 34.4 (C-10), 31.9 (C-15), 28.6 (C-2), 27.2 (C-6), 27.1 (C-23), 26.8 (C-7), 26.1 (C-25), 25.9 (C-24), 23.7

(C-19), 20.7 (C-11), 16.6 (C-18), 16.2 (C-27), 14.5 (C-21). LC-MS, calculated ($C_{34}H_{49}ClN_2O_3$, M) 568.3432, found [M+H]$^+$: 569.3498.

Example 18

Preparation of Compound C-11

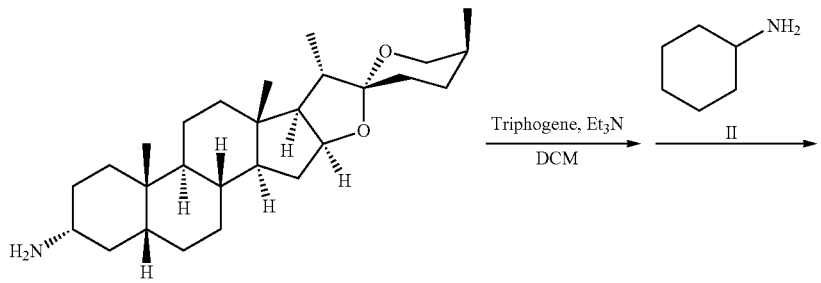

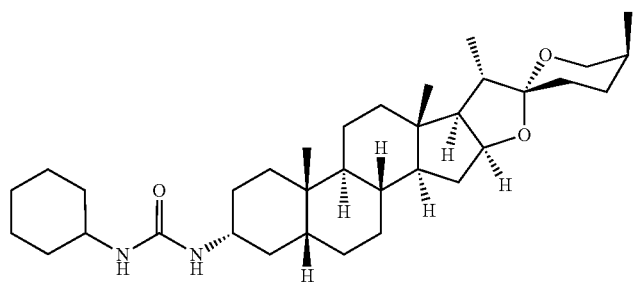

800 mg of triphosgene was dissolved in 50 ml of DCM, and a solution of 1 g 3α-amino sarsasapogenin in 20 ml DCM was slowly added dropwise into the reaction system, 1 ml triethylamine was slowly added dropwise into the reaction system, then the solvent was evaporated under reduced pressure. The residue was dissolved in 150 ml of DCM. A solution of 2 equivalent of cyclohexylamine in 20 ml of DCM was added dropwise into the reaction system, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography (eluent P/E=3:1~2:1) to give 750 mg of compound C-11.

$^1$H NMR (300 MHz, CDCl$_3$): 4.40 (1H, dd, J=6.0, 12.0 Hz, H-16), 3.95 (1H, dd, J=3.0, 9.0 Hz, H-26a), 3.49 (1H, m, H-3), 3.47 (1H, m, H-1'), 3.30 (1H, d, J=9.0 Hz, H-26b), 1.08 (3H, d, J=6.0 Hz, H-21), 0.99 (3H, d, J=6.0 Hz, H-27), 0.94 (3H, s, H-19), 0.75 (3H, s, H-18). $^{13}$C NMR (300 MHz, CDCl$_3$): δ157.2 (C=O), 109.9 (C-22), 81.1 (C-16), 65.3 (C-26), 62.2 (C-17), 56.6 (C-14), 50.4 (C-3), 49.1 (C-1'), 42.5 (C-5), 42.2 (C-20), 40.8 (C-9), 40.8 (C-13), 40.4 (C-12), 36.2 (C-4), 35.5 (C-8), 34.9 (C-1), 34.7 (C-10), 34.1 (C-2', C-6'), 31.9 (C-15), 28.8 (C-2), 27.2 (C-6), 27.1 (C-23), 26.8 (C-7), 26.1 (C-25), 25.9 (C-24), 25.7 (C-4'), 25.1 (C-3', C-5'), 23.7 (C-19), 20.7 (C-11), 16.6 (C-18), 16.2 (C-27), 14.4 (C-21). LC-MS, calculated ($C_{34}H_{56}N_2O_3$, M) 540.4291, found [M+H]$^+$: 541.4353.

Example 19

Preparation of Compound C-12

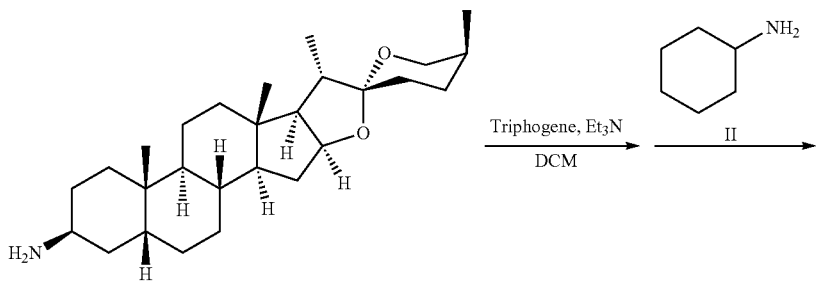

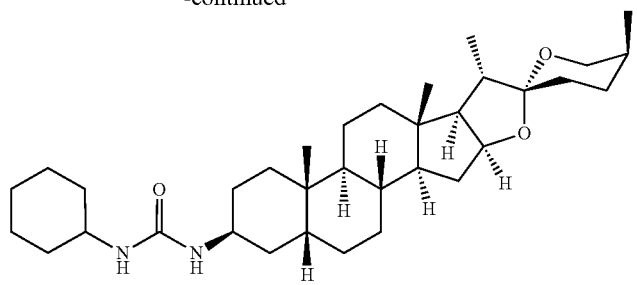

800 mg of triphosgene was dissolved in 50 ml of DCM, and a solution of 1 g 3-amino sarsasapogenin in 20 ml DCM was slowly added dropwise into the reaction system, 1 ml triethylamine was slowly added dropwise into the reaction system, then the solvent was evaporated under reduced pressure. The residue was dissolved in 150 ml of DCM. A solution of 2 equivalent of cyclohexylamine in 20 ml of DCM was added dropwise into the reaction system, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography (eluent P/E=3:1~2:1) to give 700 mg of compound C-12.

$^1$H NMR (300 MHz, CDCl$_3$): 4.40 (1H, dd, J=6.0, 9.0 Hz, H-16), 3.95 (1H, m, H-26a), 3.94 (1H, m, H-3), 3.52 (1H, m, H-1'), 3.30 (1H, d, J=6.0 Hz, H-26b), 1.08 (3H, d, J=6.0 Hz, H-21), 0.99 (3H, d, J=6.0 Hz, H-27), 0.96 (3H, s, H-19), 0.75 (3H, s, H-18). $^{13}$C NMR (300 MHz, CDCl$_3$): δ 157.2 (C=O), 109.8 (C-22), 81.1 (C-16), 65.2 (C-26), 62.2 (C-17), 56.5 (C-14), 45.8 (C-3), 49.1 (C-1'), 42.5 (C-20), 40.3 (C-9), 40.8 (C-13), 40.0 (C-12), 37.9 (C-5), 35.4 (C-10), 35.3 (C-8), 31.5 (C-4), 31.3 (C-1), 34.1 (C-2', C-6'), 31.8 (C-15), 26.9 (C-7), 27.2 (C-23), 26.6 (C-7), 26.1 (C-25), 25.9 (C-24), 25.8 (C-4'), 25.6 (C-6), 25.1 (C-3', C-5'), 24.2 (C-19), 20.9 (C-11), 16.6 (C-18), 16.2 (C-27), 14.4 (C-21). LC-MS, calculated (C$_{34}$H$_{56}$N$_2$O$_3$, M) 540.4291, found [M+H]$^+$: 541.4331.

Example 20

Preparation of 3-Cyclohexyl Ureidosarsasapogenin (a Mixture of Compound C-11 and Compound C-12)

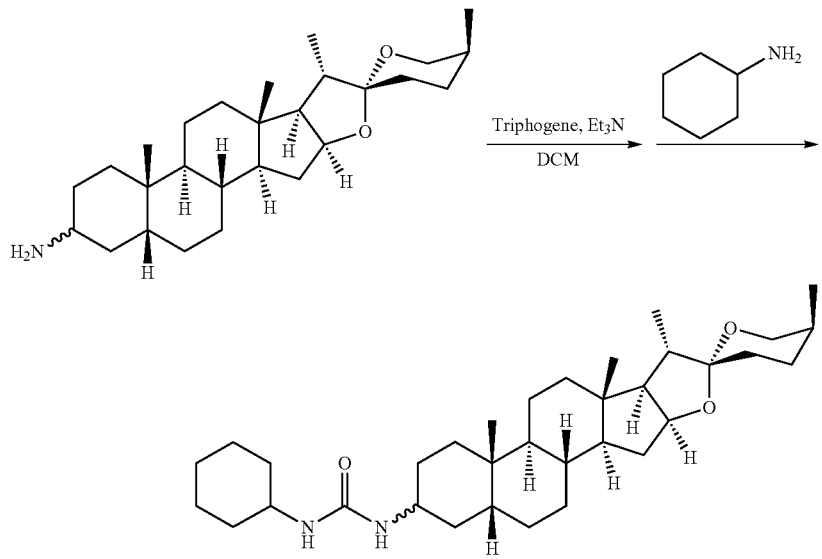

800 mg of triphosgene was dissolved in 5 ml of DCM, and a solution of 100 mg 3-amino sarsasapogenin (a mixture of two conformations) in 2 ml DCM was slowly added dropwise into the reaction system, 85 μl triethylamine was slowly added dropwise into the reaction system, then the solvent was evaporated under reduced pressure. The residue was dissolved in 5 ml of DCM. A solution of 2 equivalent cyclohexylamine in 2 ml of THF was added dropwise into the reaction system, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography to give 60 mg of 3-cyclohexyl ureidosarsasapogenin as a mixture of compound C-11 and compound C-12 (mass ratio: about 6:4). 3-amino sarsasapogenin used (a mixture of alpha conformation and beta conformation) was prepared in example 3.

Example 21

Preparation of Compound C-11 and Compound C-12 by the Resolution of 3-Cyclohexyl Ureido Sarsasapogenin in Example 20 by HPLC Preparation Column

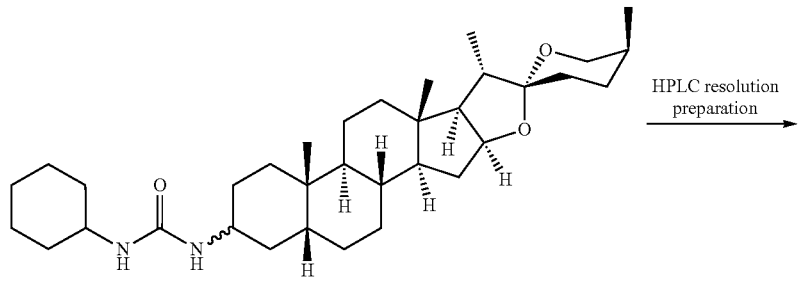

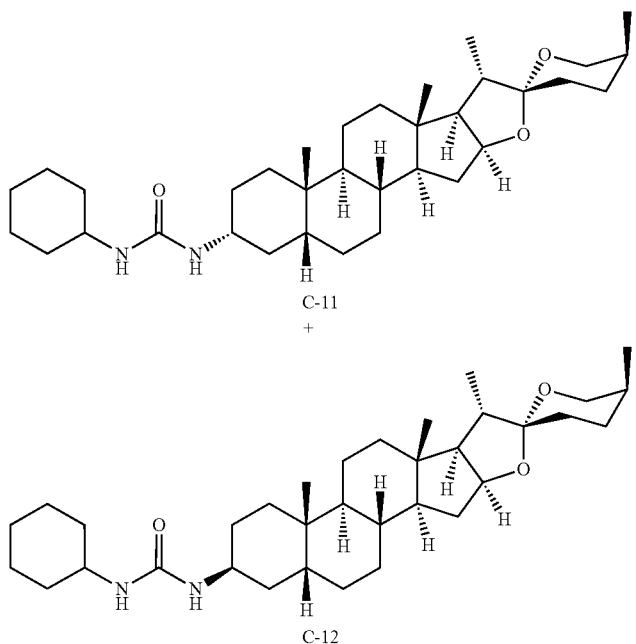

60 mg of 3-cyclohexyl ureidosarsasapogenin obtained by the separation of silica gel column chromatography in example 20 was subjected to the resolution of HPLC preparation column to give a pure optical isomer, wherein compound C-11 is 30 mg and compound C-12 is 20 mg.

Example 22

Preparation of Compound C-17

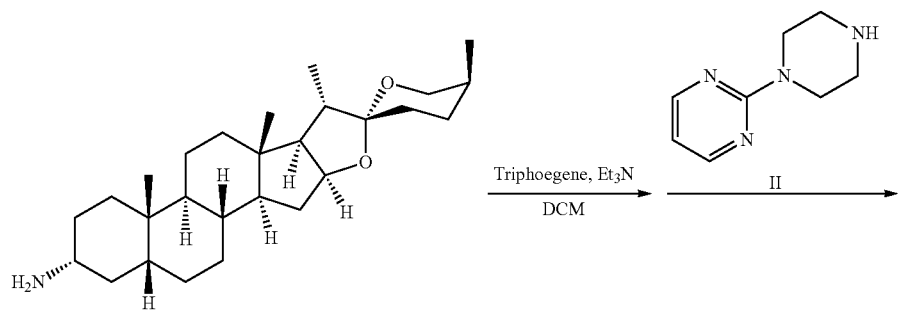

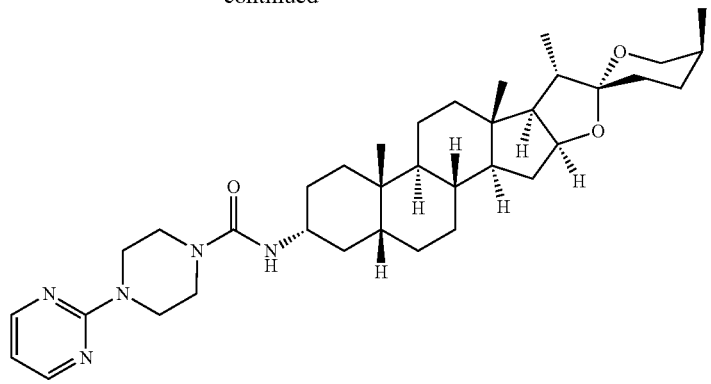

800 mg of triphosgene was dissolved in 20 ml of DCM, and 1.1 g of 3α-amino sarsasapogenin was dissolved in 20 ml of DCM, and then slowly added dropwise into the reaction system. 0.82 ml of triethylamine was dissolved in 20 ml of DCM and then slowly added dropwise into the reaction system, and the solvent was evaporated under reduced pressure. The residue was dissolved in 30 ml of DCM. A solution of 443 mg amine II in 30 ml of DCM was added dropwise into the reaction system, and the solvent was evaporated under reduced pressure. The residue was separated by column chromatography to give 1.3 g of compound. LC-MS, calculated ($C_{36}H_{55}N_5O_3$, M) 605.4305, found [M+H]$^+$: 606.4339.

Example 23

Preparation of Compound C-17 and Compound C-18 by HPLC Preparation Column Resolution

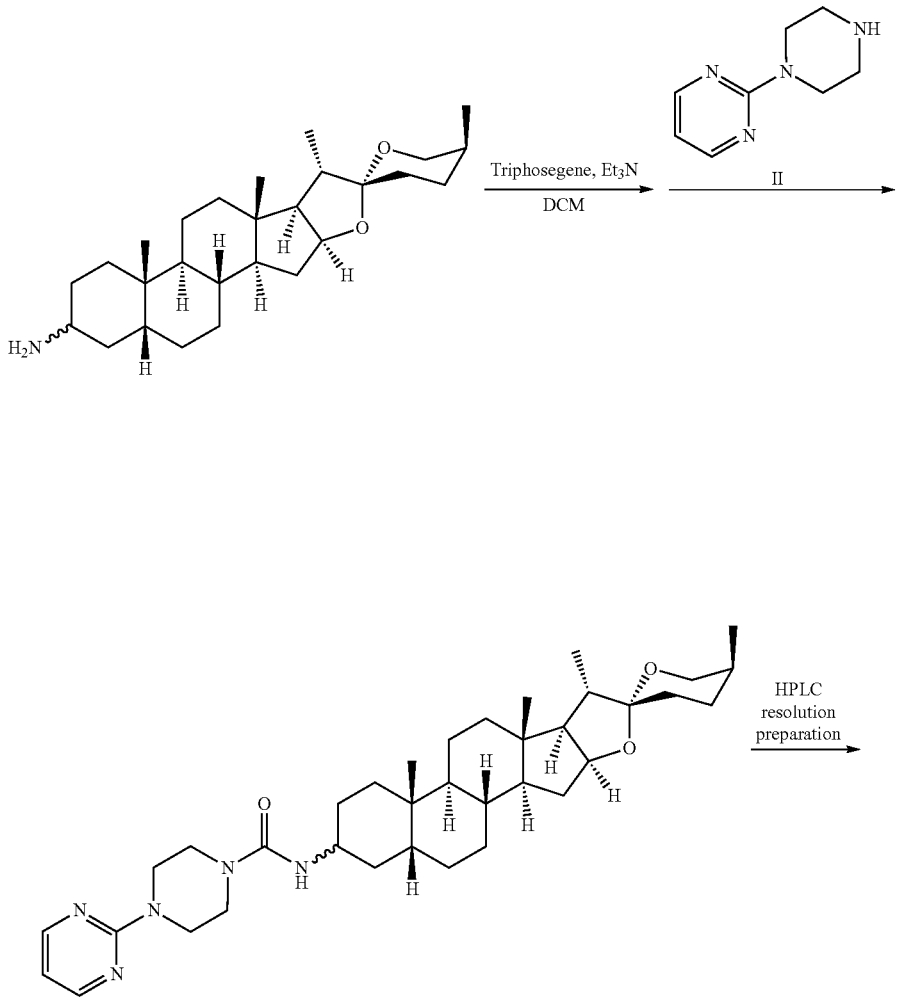

-continued

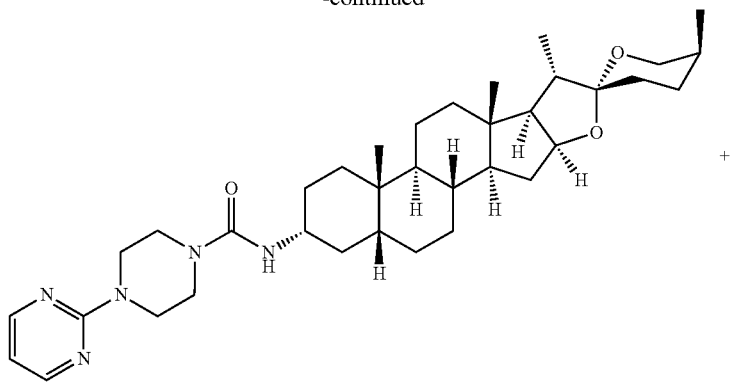

+

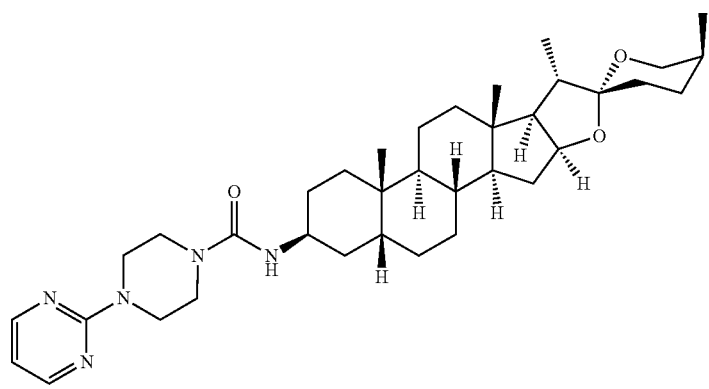

80 mg of triphosgene was dissolved in 2 ml of DCM, and 110 mg of 3-amino sarsasapogenin (a mixture of two conformations) was dissolved in 2 ml of DCM, and then slowly added dropwise into the reaction system. 90 μl of triethylamine was dissolved in 2 ml of DCM and then slowly added dropwise into the reaction system, and the solvent was evaporated under reduced pressure. The residue was dissolved in 3 ml of DCM. A solution of 45 mg amine II in 3 ml of DCM was added dropwise to the reaction solution, and the solvent was evaporated under reduced pressure. The residue was dissolved in DCM, washed with 1M hydrochloric acid, saturated sodium bicarbonate solution, and saturated sodium chloride solution, and dried over anhydrous sodium sulfate. The crude product was separated by silica gel column chromatography, and then subjected to the resolution by HPLC preparation column to obtain a pure optical isomer, wherein compound C-17 is 60 mg and compound C-18 is 50 mg. The 3-amino sarsasapogenin used (a mixture of alpha conformation and beta conformation) was prepared in example 3.

Example 24

Preparation of Compound C-20

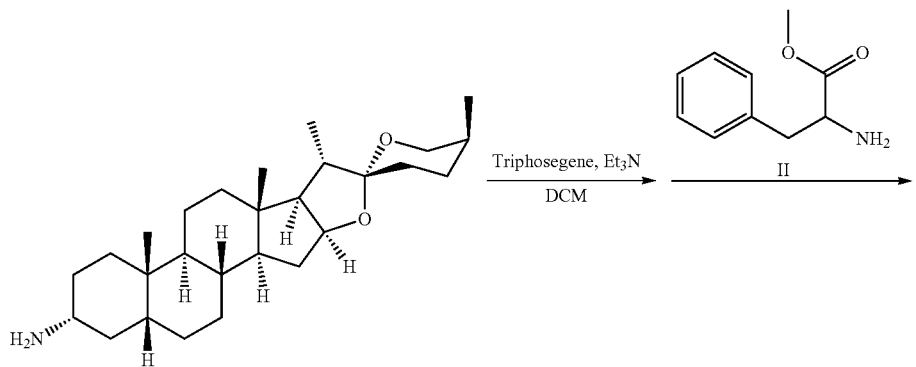

-continued

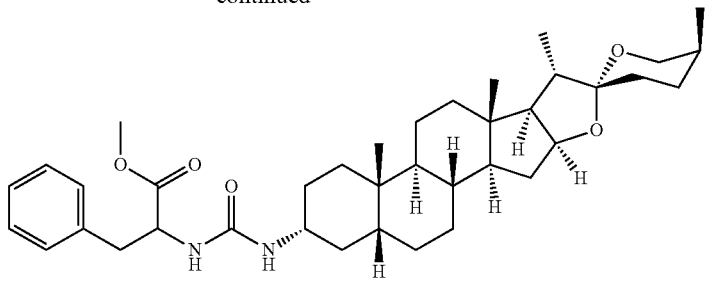

The preparation method was the same as the preparation method of compound C-17 in example 22. LC-MS, calculated ($C_{38}H_{56}N_2O_5$, M) 620.4189, found $[M+H]^+$: 621.4236.

Example 25

Preparation of Compound C-11

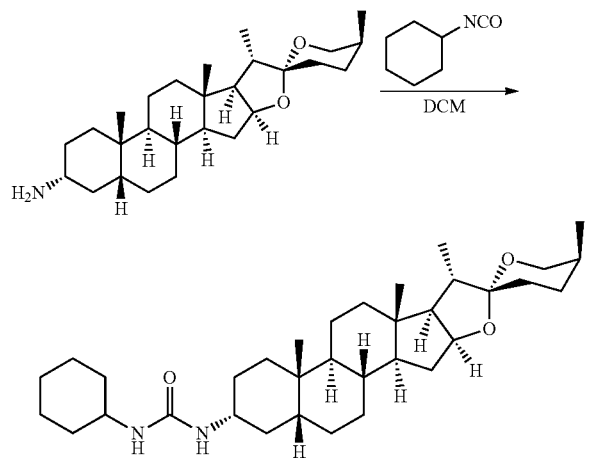

2 g of 3α-amino sarsasapogenin was dissolved in 80 ml of DCM, 2 ml of cyclohexylisocyanate was added, and the mixture was stirred at room temperature overnight. The reaction mixture was diluted with DCM, washed with 1M hydrochloric acid, saturated sodium bicarbonate solution, and saturated sodium chloride solution, dried over anhydrous sodium sulfate, and separated by silica gel column chromatography (eluent P/E=3:1) to give 1.5 g of compound C-11.

Example 26

Preparation of Compound C-12

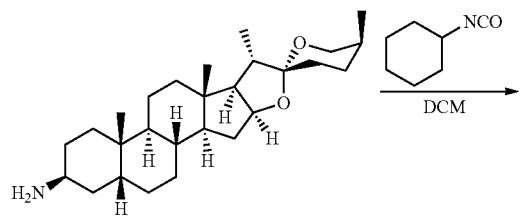

-continued

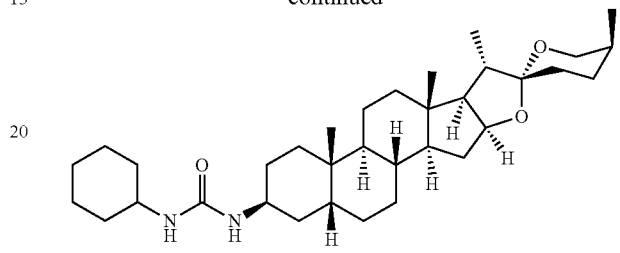

2 g of 3β-amino sarsasapogenin was dissolved in 80 ml of DCM, 2 ml of cyclohexylisocyanate was added, and the mixture was stirred at room temperature overnight. The reaction mixture was diluted with DCM, washed with 1M hydrochloric acid, saturated sodium bicarbonate solution, and saturated sodium chloride solution, dried over anhydrous sodium sulfate, and separated by silica gel column chromatography (eluent P/E=3:1) to give 1.5 g of compound C-12.

Compounds C-19, C-21 and C-32 were prepared by referring to the preparation methods of examples 1-26.

Example 27 Synthesis of Compound C-33

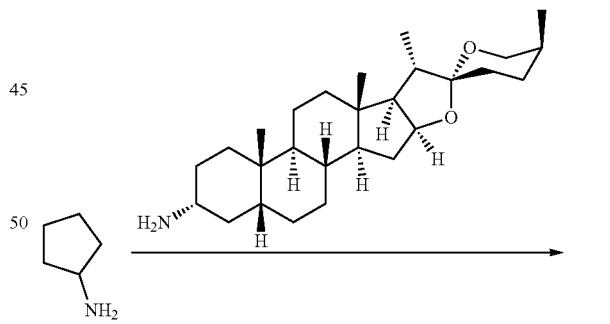

Triphosgene (1 mmol) was dissolved in 60 ml DCM, 3α-amino sarsasapogenin (1 mmol) was dissolved in 30 ml DCM and then slowly added dropwise into the reaction system. Triethylamine (2.2 mmol) was dissolved in 30 ml DCM, then slowly added dropwise into the reaction system, the solvent was evaporated under reduced pressure. The residue was dissolved in 60 ml DCM, a solution of cyclopentylamine (2 mmol) in 30 ml DCM was slowly added dropwise into the reaction system and reacted overnight. The mixture was washed with 1M hydrochloric acid, saturated sodium bicarbonate solution, and saturated sodium chloride solution, dried over anhydrous sodium sulfate, and separated by silica gel column chromatography to give the compound in a yield of 60%.

$^1$H NMR (400 MHz, Chloroform-d) 4.53 (d, J=7.2 Hz, 2H), 4.47-4.36 (m, 2H), 3.96 (ddd, J=13.1, 8.7, 5.9 Hz, 3H), 3.55 (s, 1H), 3.31 (d, J=10.9 Hz, 1H), 1.27 (s, 4H), 1.09 (d, J=7.0 Hz, 4H), 1.00 (d, J=6.8 Hz, 3H), 0.95 (s, 4H), 0.76 (s, 3H).

LC-MS, theoretical value $(C_{33}H_{55}N_2O_3, [M+H]^+)$ 527.4213, found: 527.4185.

Example 28 Synthesis of Compound C-34

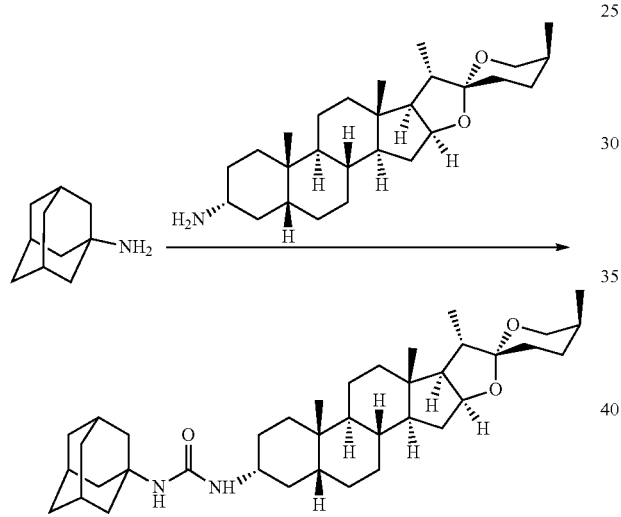

Triphosgene (1 mmol) was dissolved in 60 ml DCM, and 3α-amino sarsasapogenin (1 mmol) was dissolved in 30 ml DCM, then slowly added dropwise into the reaction system. Triethylamine (2.2 mmol) was dissolved in 30 ml DCM, then slowly added dropwise into the reaction system, the solvent was evaporated under reduced pressure. The residue was dissolved in 60 ml DCM. A solution of amantadine hydrochloride (2 mmol) and triethylamine (2 mmol) in 30 ml DCM was slowly added dropwise into the reaction system and reacted overnight. The mixture was washed with 1M hydrochloric acid, saturated sodium bicarbonate solution, and saturated sodium chloride solution, dried over anhydrous sodium sulfate, and separated by silica gel column chromatography to give the compound in a yield of 70%.

$^1$H NMR (400 MHz, Chloroform-d) 4.42 (q, J=7.4 Hz, 1H), 4.15 (s, 2H), 3.97 (dd, J=11.0, 2.7 Hz, 1H), 3.47 (td, J=10.9, 5.6 Hz, 1H), 3.32 (d, J=10.9 Hz, 1H), 1.09 (d, J=7.1 Hz, 4H), 1.01 (d, J=6.7 Hz, 3H), 0.95 (s, 4H), 0.76 (s, 3H).

LC-MS, theoretical value $(C_{38}H_{61}N_2O_3, [M+H]^+)$ 593.4682, found: 593.4668.

Example 29 Synthesis of Substituted Cyclohexane

Method 1: Reduction Amination Reaction

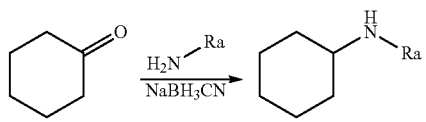

Cyclohexanone (3 eq.) and amine (1 eq.) were dissolved in methanol, 0.2 eq. of acetic acid and then sodium cyanoborohydride (1.2 eq.) were added for reduction. The solvent was removed under reduced pressure, and saturated sodium chloride and ethyl acetate were added. The organic layer was extracted and subjected to flash column chromatography on silica gel to give the compound which was directly used in the next reaction. According to this method, the following compounds can be obtained:

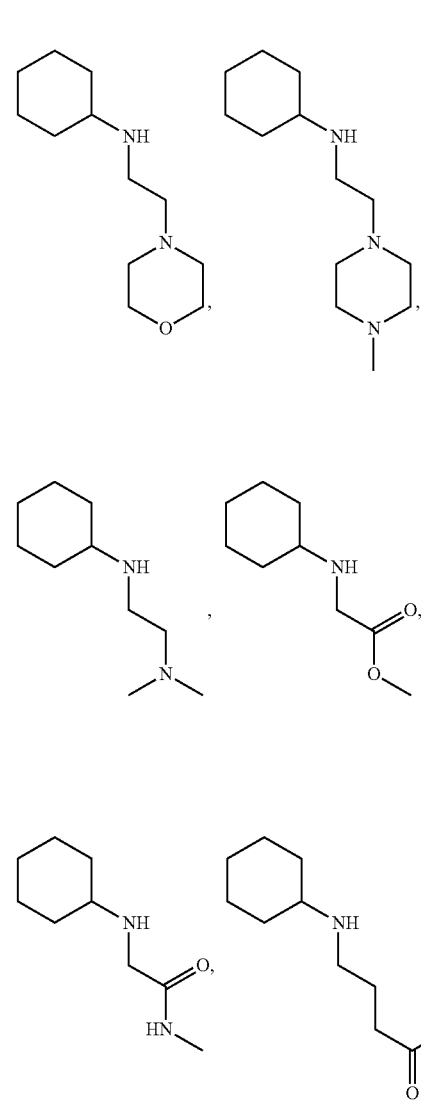

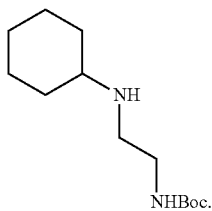

Method 2: Nucleophilic Substitution

Cyclohexylamine (5 mmol) and 2-chloromethylamide (5.5 mmol) were dissolved in 30 ml of DMF, and potassium carbonate (15 mmol) was added to the system and reacted overnight. The mixture was extracted with ethyl acetate three times with 200 ml each time, and then the ethyl acetate layer was washed three times with saturated sodium chloride solution. The organic layer was separated, and then subjected to flash column chromatography on silica gel to give the compound which was directly used in the next reaction.

Example 30 Synthesis of Compounds C-35 to C-39

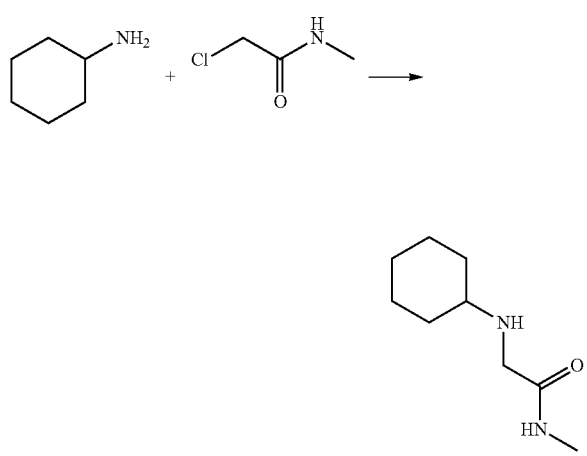

cyclohexane derivatives

Triphosgene (1 mmol) was dissolved in 60 ml DCM, 3α-amino sarsasapogenin (1 mmol) was dissolved in 30 ml DCM, then slowly added dropwise into the reaction system. Triethylamine (2.2 mmol) was dissolved in 30 ml DCM, then slowly added dropwise into the reaction system. The solvent was evaporated under reduced pressure and the residue was dissolved in 60 ml DCM and a solution of cyclohexane derivative (2 mmol) in 30 ml DCM was slowly added dropwise into the reaction system and reacted overnight. The mixture was washed with 1M hydrochloric acid, saturated sodium bicarbonate solution, and saturated sodium chloride solution, dried over anhydrous sodium sulfate and separated by silica gel column chromatography to give compound as shown in table 1.

TABLE 1

Chemical structure and data of compounds C-35 to C-39

| Ra | Target compound | Data |
|---|---|---|
| (cyclohexyl-NH-CH2CH2-OH) | (structure shown) | $^1$H NMR (400 MHz, Chloroform-d) δ 5.10 (s, 1H), 4.47-4.36 (m, 1H), 3.97 (dd, J = 11.0, 2.8 Hz, 1H), 3.72 (t, J = 4.8 Hz, 2H), 3.58 (ddt, J = 36.2, 11.5, 4.6 Hz, 2H), 3.40-3.28 (m, 3H), 1.09 (d, J = 7.0 Hz, 4H), 1.01 (d, J = 6.7 Hz, 3H), 0.77 (s, 3H), 0.08 (s, 1H). $^{13}$C NMR (100 MHz, Chloroform-d) δ 109.78, 81.03, 77.24, 65.16, 62.08, 56.34, 42.49, 42.11, 40.65, 40.62, 40.23, 36.03, 35.46, 34.78, 34.37, 31.76, 31.05, 28.55, 27.07, 27.01, 26.70, 25.93, 25.86, 25.75, 25.43, 23.60, 20.64, 16.48, 16.04, 14.36. LC-MS, theoretical value ($C_{36}H_{61}N_2O_4$, [M + H]$^+$) 585.4631, found: 585.4615. Yield 80%. |

TABLE 1-continued

Chemical structure and data of compounds C-35 to C-39

| Target compound | Data |
|---|---|
| | ¹H NMR (400 MHz, Chloroform-d) δ 7.14 (d, J = 7.9 Hz, 1H), 4.38 (q, J = 7.3 Hz, 1H), 4.09 (ddt, J = 11.9, 7.4, 3.8 Hz, 1H), 3.96 (dd, J = 11.0, 2.7 Hz, 1H), 3.63 (tdt, J = 12.0, 8.2, 4.2 Hz, 1H), 3.31 (d, J = 10.9 Hz, 1H), 3.15 (t, J = 4.5 Hz, 2H), 2.47 (t, J = 4.6 Hz, 2H), 2.33 (s, 3H), 1.09 (d, J = 6.7 Hz, 4H), 1.00 (d, J = 6.9 Hz, 3H), 0.97 (s, 3H), 0.77 (s, 3H). LC-MS, theoretical value (C₄₁H₇₁N₄O₃, [M + H]⁺) 667.5526, found: 667.5488. Yield 78%. |
| | ¹H NMR (400 MHz, Chloroform-d) δ 4.42 (q, J = 7.4 Hz, 1H), 4.04-3.92 (m, 2H), 3.55 (s, 1H), 3.31 (d, J = 11.0 Hz, 1H), 3.20 (t, J = 5.1 Hz, 2H), 2.49 (s, 2H), 2.33 (s, 6H), 1.09 (d, J = 7.1 Hz, 6H), 1.00 (d, J = 6.7 Hz, 3H), 0.95 (s, 3H), 0.77 (s, 3H). LC-MS, theoretical value (C₃₈H₆₆N₃O₃, [M + H]⁺) 612.5104, found: 612.5116. Yield 78%. |
| | ¹H NMR (400 MHz, Chloroform-d) δ 4.54 (dd, J = 22.3, 7.5 Hz, 1H), 4.39 (q, J = 7.3 Hz, 1H), 3.94 (d, J = 11.1 Hz, 1H), 3.88 (s, 1H), 3.72 (s, 2H), 3.68-3.40 (m, 2H), 3.29 (d, J = 11.0 Hz, 1H), 0.98 (d, J = 6.6 Hz, 2H), 0.93 (s, 3H), 0.74 (s, 3H). LC-MS, theoretical value (C₃₇H₆₁N₂O₅, [M + H]⁺) 613.4580, found: 613.4433. Yield 80%. |
| | ¹H NMR (400 MHz, Chloroform-d) δ 6.74 (d, J = 5.4 Hz, 1H), 4.41 (dd, J = 16.5, 7.3 Hz, 2H), 3.98 (dd, J = 11.0, 2.7 Hz, 1H), 3.79 (s, 2H), 3.74-3.58 (m, 3H), 3.33 (d, J = 11.1 Hz, 1H), 2.82 (d, J = 4.9 Hz, 3H), 1.60 (s, 7H), 1.10 (d, J = 7.0 Hz, 4H), 1.02 (d, J = 6.6 Hz, 3H), 0.97 (s, 3H), 0.78 (s, 3H). LC-MS, theoretical value (C₃₇H₆₂N₃O₄, [M + H]⁺) 612.4740, found: 612.4720. Yield 50%. |

Example 31 Synthesis of Compounds C-40 to C-41
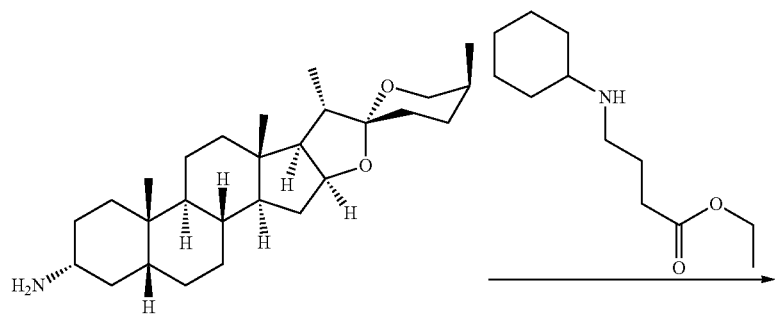
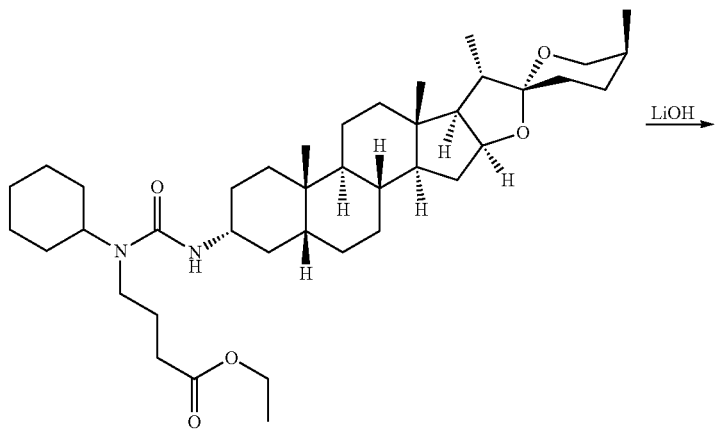
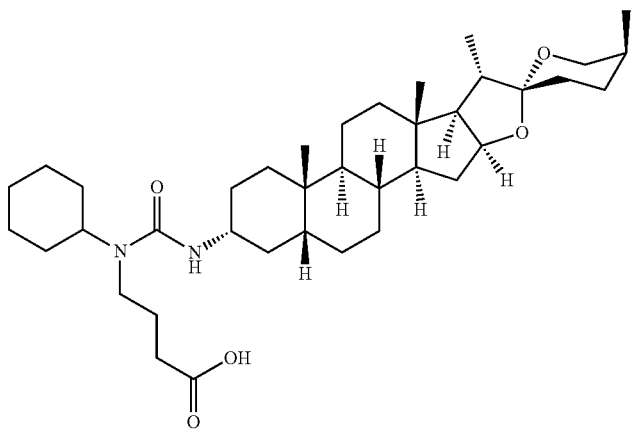

The synthesis of the urea-derivative was carried out by referring to the synthesis of compound C-34. The substrate (1 mmol) in 30 ml of THF and 30 ml of water was added with lithium hydroxide (8 mmol, and THF was removed by rotary evaporation. The remaining reaction mixture was added with 1 M hydrochloric acid to acidity, and a white solid was precipitated and filtered. After the residue was washed with water, the residue was dried under vacuum to give a compound (yield: 80%).

$^1$H NMR (400 MHz, Chloroform-d) 5.13 (d, J=23.8 Hz, 1H), 4.43 (q, J=7.2 Hz, 1H), 3.97 (dd, J=11.2, 2.7 Hz, 1H), 3.89 (s, 1H), 3.68 (s, 1H), 3.32 (d, J=10.9 Hz, 1H), 3.12 (t, J=7.8 Hz, 2H), 2.40 (t, J=6.1 Hz, 2H), 1.45 (s, 2H), 1.10 (d, J=6.9 Hz, 4H), 1.01 (d, J=6.5 Hz, 3H), 0.96 (s, 3H), 0.78 (s, 3H).

LC-MS, theoretical value ($C_{38}H_{63}N_2O_5$, [M+H]$^+$) 627.4737, found: 627.4675.

Example 32 Synthesis of Compounds C-42 to C-43

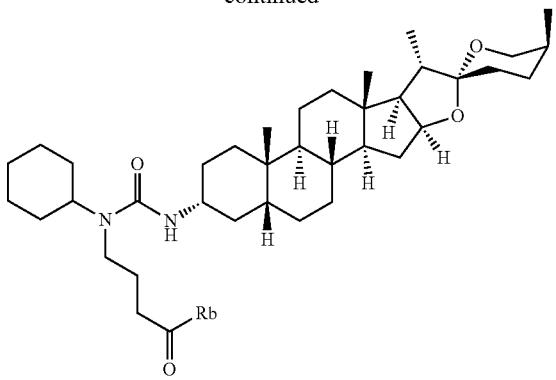

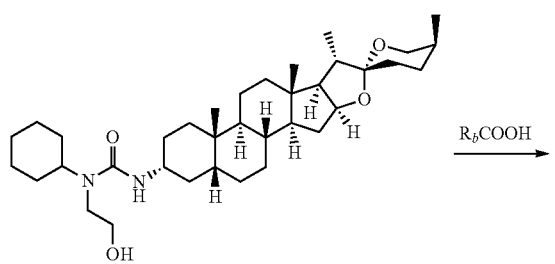

The substrate (1 mmol) was dissolved in 30 ml of DCM, EDCI.HCl (2 mmol) and DMAP (3 mmol) was added to the reaction system, and RbCOOH (2 mmol) was added to the reaction system, stirred at room temperature overnight. And the reaction mixture was diluted with DCM and washed with saturated sodium bicarbonate solution, washed with saturated sodium chloride solution, dried over anhydrous sodium sulfate and subjected to the silica gel column chromatography to give a compound as shown in Table 2.

TABLE 2

Chemical structure and data of compounds C-42 to C-43

| R$_b$COOH | structure of product | data |
|---|---|---|
| ![HO-CH2-N(CH3)2 structure] | ![product structure] | $^1$H NMR (400 MHz, Chloroform-d) δ 5.04 (d, J = 7.2 Hz, 1H), 4.50-4.32 (m, 1H), 4.16 (t, J = 7.2 Hz, 2H), 3.93 (ddd, J = 15.7, 9.8, 2.9 Hz, 2H), 3.64 (tq, J = 11.1, 4.9 Hz, 1H), 3.31 (t, J = 7.4 Hz, 3H), 3.24 (s, 2H), 2.40 (s, 6H), 1.08 (d, J = 7.1 Hz, 4H), 0.99 (d, J = 6.8 Hz, 3H), 0.95 (s, 3H), 0.76 (s, 3H).<br>$^{13}$C NMR (100 MHz, Chloroform-d) δ 170.76, 157.19, 109.72, 81.01, 77.25, 65.13, 63.70, 62.16, 60.09, 56.39, 54.13, 50.84, 45.24, 42.51, 42.10, 40.65, 40.33, 40.26, 36.12, 35.48, 34.78, 34.42, 31.76, 31.41, 28.53, 27.07, 27.04, 26.72, 25.93, 25.75, 25.54, 23.60, 20.64, 16.47, 16.03, 14.34. Yield 75%. |

TABLE 2-continued

Chemical structure and data of compounds C-42 to C-43

| R$_b$COOH | structure of product | data |
|---|---|---|
| 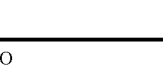 | 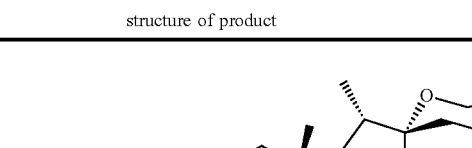 | $^1$H NMR (400 MHz, Chloroform-d) δ 9.33 (s, 1H), 8.80 (s, 1H), 8.73 (s, 1H), 4.93 (d, J = 7.1 Hz, 1H), 4.48 (t, J = 7.1 Hz, 2H), 4.40 (q, J = 7.6, 7.2 Hz, 1H), 3.87 (s, 1H), 3.69-3.59 (m, 1H), 3.50 (t, J = 7.0 Hz, 2H), 3.29 (d, J = 11.0 Hz, 1H), 1.07 (d, J = 7.4 Hz, 6H), 0.75 (s, 3H). LC-MS, theoretical value (C$_{41}$H$_{63}$N$_4$O$_5$, [M + H]$^+$) 691.4798, found: 691.4765. Yield 66%. |

Example 33 Synthesis of Compound C-44

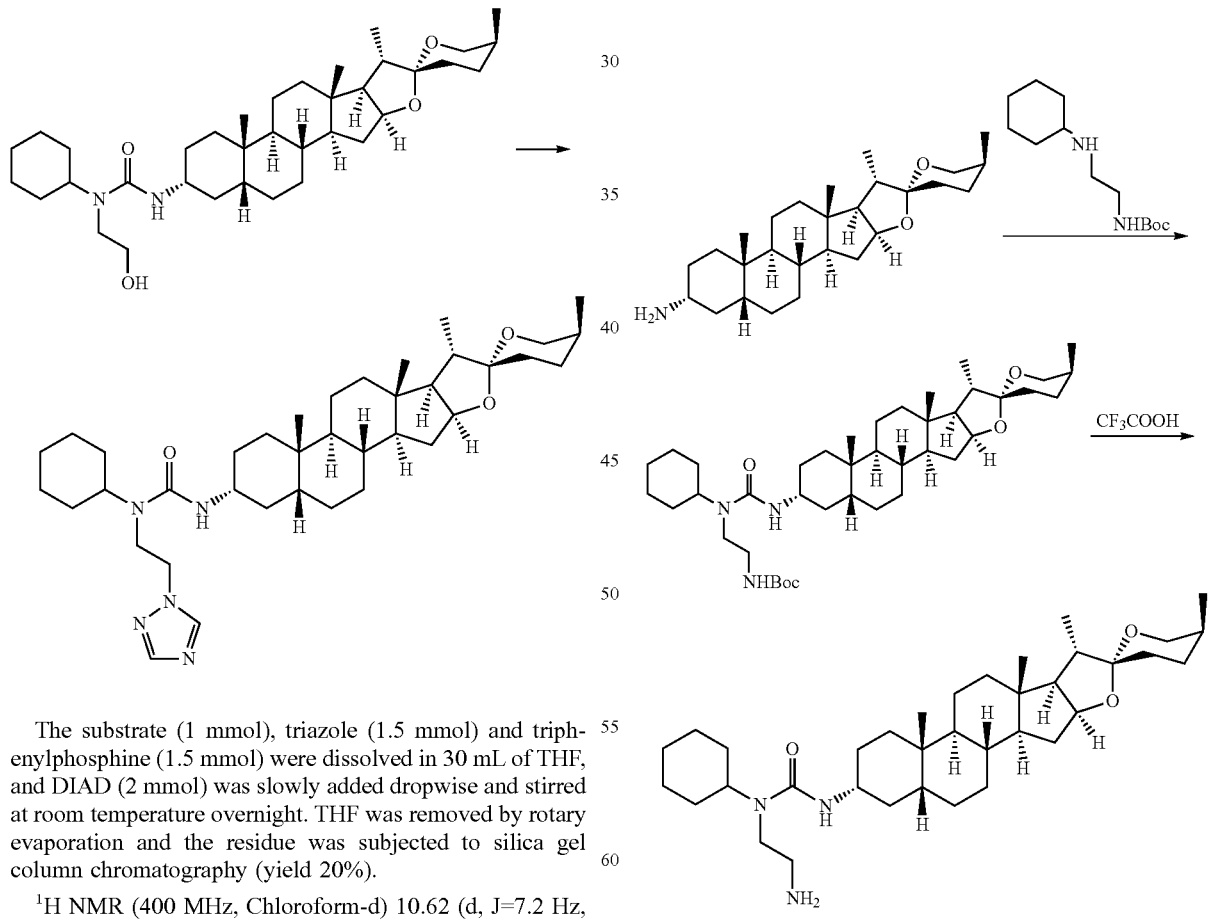

The substrate (1 mmol), triazole (1.5 mmol) and triphenylphosphine (1.5 mmol) were dissolved in 30 mL of THF, and DIAD (2 mmol) was slowly added dropwise and stirred at room temperature overnight. THF was removed by rotary evaporation and the residue was subjected to silica gel column chromatography (yield 20%).

$^1$H NMR (400 MHz, Chloroform-d) 10.62 (d, J=7.2 Hz, 1H), 8.23 (s, 2H), 4.89 (s, 1H), 4.72 (t, J=8.4 Hz, 2H), 4.41 (d, J=7.0 Hz, 1H), 3.96 (dd, J=11.2, 2.8 Hz, 1H), 3.83 (t, J=8.4 Hz, 2H), 3.55 (d, J=32.4 Hz, 2H), 3.33 (d, J=11.0 Hz, 1H), 2.30 (q, J=12.6 Hz, 1H), 1.04 (dd, J=38.5, 6.8 Hz, 6H), 0.94 (s, 3H), 0.73 (s, 3H).

LC-MS, theoretical value (C$_{38}$H$_{62}$N$_5$O$_3$, [M+H]$^+$) 636.4853, found: 636.4813.

Example 34 Synthesis of Compounds C-45 to C-46

An intermediate obtained in the first step of the urea-forming reaction was synthesized by referring to synthesis of compound C-34. The substrate (1 mmol) was dissolved in DCM, a solution of HCl (8 mmol) in ethyl acetate was added and stirred at room temperature overnight. The solvent was removed under reduced pressure and the residue was dried to obtain the target compound (yield 65%).

¹H NMR (400 MHz, Chlorofom-d) δ 4.40 (q, J=7.4, 6.8 Hz, 1H), 4.00-3.89. (m, 1H), 3.62 (d, J=10.6 Hz, 4H), 3.47 (s, 2H), 3.29 (d, J=10.8 Hz, 1H), 3.24-3.08 (m, 3H), 1.08 (d, J=7.0 Hz, 3H), 0.99 d, J=6.7 Hz, 3H), 0.95 (s, 4H), 0.75 (s, 3H).

¹³C NMR (100 MHz, Chloroform-d) 157.60, 109.72, 81.01, 77.26, 65.12, 57.27, 56.21, 51.91, 42.51, 42.10, 40.63, 40.52, 40.18, 35.97, 35.49, 34.75, 34.02, 31.76, 30.80, 28.25, 27.06, 26.69, 25.95, 25.72, 25.10, 23.52, 20.64, 16.44, 16.04, 14.35.

LC-MS, theoretical value ($C_{36}H_{62}N_3O_3$, [M+H]⁺) 584.4791, found: 584.4751.

Example 35 Synthesis of Compounds C-47 to C-52

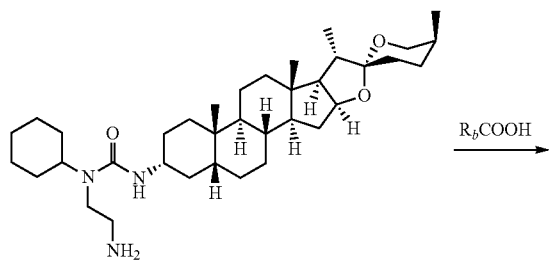

R$_b$COOH →

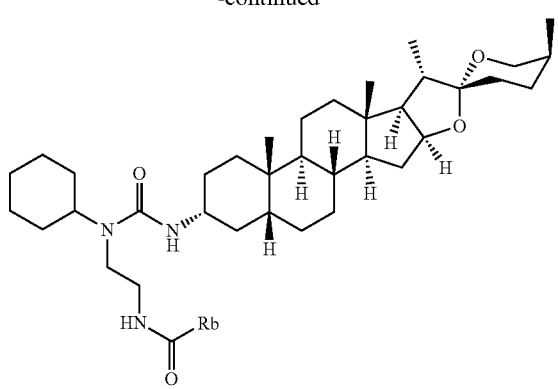

The substrate (1 mmol) was dissolved in 30 ml DCM, EDCI.HCl (2 mmol) and DMAP (3 mmol) were added to the reaction system and then RbCOOH (2 mmol) was added to the reaction system and stirred at room temperature overnight. The reaction mixture was diluted with DCM, washed with saturated sodium bicarbonate solution, washed with saturated sodium chloride solution, dried over anhydrous sodium sulfate and subjected to silica gel column chromatography to give a compound as shown in Table 3.

TABLE 3

Chemical structure and data of compounds C-47 to C-52

| R$_b$COOH | structure of product | data |
|---|---|---|
| (pyrazine-2-carboxylic acid) | (product structure) | ¹H NMR (400 MHz, Chloroform-d) δ 9.33 (d, J = 1.5 Hz, 1H), 8.71 (d, J = 2.5 Hz, 1H), 8.53-8.39 (m, 2H), 5.54-5.47 (m, 1H), 4.40-4.30 (m, 1H), 3.89 (dd, J = 11.0, 2.7 Hz, 1H), 3.82 (s, 1H), 3.63 (dq, J = 15.3, 6.4, 5.9 Hz, 1H), 3.52-3.43 (m, 2H), 3.35-3.19 (m, 3H), 2.75 (s, 6H), 2.47 (s, 1H), 1.06-0.91 (m, 7H), 0.90 (s, 3H), 0.71 (s, 3H). LC-MS, theoretical value ($C_{41}H_{64}N_5O_4$, [M + H]⁺) 690.4958, found: 690.4902. Yield 75%. |
| (tetrazole acetic acid) | (product structure) | ¹H NMR (400 MHz, Chloroform-d) δ 8.29 (s, 1H), 4.93 (d, J = 9.3 Hz, 1H), 4.41 (q, J = 7.2 Hz, 1H), 3.98 (d, J = 29.6 Hz, 3H), 3.72-3.59 (m, 1H), 3.48 (d, J = 12.3 Hz, 1H), 3.36 (s, 4H), 3.31 (d, J = 10.8 Hz, 1H), 1.26 (s, 6H), 1.08 (d, J = 7.1 Hz, 4H), 1.00 (d, J = 6.7 Hz, 2H), 0.95 (s, 3H), 0.76 (s, 3H). LC-MS, theoretical value ($C_{39}H_{64}N_7O_4$, [M + H]⁺) 694.5020, found: 694.4825. Yield 80%. |

TABLE 3-continued

Chemical structure and data of compounds C-47 to C-52

| $R_bCOOH$ | structure of product | data |
|---|---|---|
| | | ¹H NMR (400 MHz, Chloroform-d) δ 7.60 (d, J = 6.0 Hz, 1H), 5.63 (d, J = 6.9 Hz, 1H), 4.40 (td, J = 8.1, 7.7, 4.3 Hz, 1H), 4.02-3.89 (m, 2H), 3.62 (qd, J = 10.4, 9.5, 5.2 Hz, 1H), 3.34-3.23 (m, 3H), 3.19 (dd, J = 8.7, 5.4 Hz, 2H), 3.01 (s, 2H), 2.33 (s, 6H), 1.43 (s, 2H), 0.95 (s, 3H), 0.76 (s, 3H). ¹³C NMR (100 MHz, Chloroform-d) δ 171.61, 157.36, 109.72, 81.05, 77.25, 65.13, 62.67, 62.12, 56.28, 53.83, 51.20, 45.93, 42.64, 42.10, 40.64, 40.54, 40.50, 40.24, 40.03, 36.28, 35.53, 34.85, 34.32, 31.77, 31.60, 31.54, 28.28, 27.11, 27.07, 26.73, 25.96, 25.75, 25.60, 23.66, 20.66, 16.47, 16.04, 14.33. LC-MS, theoretical value ($C_{40}H_{69}N_4O_4$, [M + H]⁺) 669.5319, found: 669.5251. Yield 60%. |
| | | ¹H NMR (400 MHz, Chloroform-d) δ 8.23 (s, 1H), 4.66 (s, 1H), 4.42 (q, J = 7.9, 7.2 Hz, 1H), 3.96 (dd, J = 11.0, 2.7 Hz, 1H), 3.63 (s, 1H), 3.57-3.19 (m, 7H), 3.00 (s, 14H), 2.84 (s, 2H), 1.09 (d, J = 7.0 Hz, 3H), 1.01 (d, J = 6.6 Hz, 3H), 0.97 (s, 3H), 0.77 (s, 3H). ¹³C NMR (100 MHz, Chloroform-d) δ 161.67, 109.72, 81.00, 77.23, 65.14, 62.12, 56.21, 51.26, 42.61, 42.13, 40.65, 40.55, 40.15, 39.89, 36.06, 35.50, 34.77, 34.38, 31.77, 30.92, 28.54, 27.08, 26.66, 25.97, 25.77, 25.11, 23.57, 20.65, 16.44, 16.04, 14.34. Yield 65%. |
| | | ¹H NMR (400 MHz, Chloroform-d) δ 7.65 (t, J = 5.4 Hz, 1H), 5.41 (s, 1H), 4.45-4.35 (m, 1H), 3.96 (dd, J = 11.0, 2.7 Hz, 1H), 3.81 (s, 1H), 3.74 (t, J = 4.6 Hz, 4H), 3.64 (dtd, J = 11.7, 7.2, 3.4 Hz, 1H), 3.36-3.18 (m, 5H), 3.03 (s, 2H), 2.54 (t, J = 4.6 Hz, 4H), 1.13-1.04 (m, 5H), 1.00 (d, J = 6.7 Hz, 3H), 0.95 (s, 3H), 0.91-0.82 (m, 2H), 0.76 (s, 3H). LC-MS, theoretical value ($C_{42}H_{71}N_4O_5$, [M + H]⁺) 711.5424, found: 711.4964. Yield 68%. |

TABLE 3-continued

Chemical structure and data of compounds C-47 to C-52

| R$_b$COOH | structure of product | data |
|---|---|---|
| (structure with N-methylpiperazine-CH$_2$-COOH) | (steroid product structure) | $^1$H NMR (400 MHz, Chloroform-d) δ 7.59 (t, J = 5.5 Hz, 1H), 5.58 (s, 1H), 4.33 (td, J = 7.8, 4.2 Hz, 1H), 3.88 (dd, J = 11.0, 2.7 Hz, 1H), 3.82 (s, 1H), 3.57 (tdt, J = 11.3, 7.9, 3.9 Hz, 1H), 3.18 (ddd, J = 33.0, 10.7, 6.2 Hz, 5H), 2.97 (s, 2H), 2.51 (t, J = 4.8 Hz, 4H), 2.45-2.38 (m, 4H), 2.25 (s, 3H), 1.01 (d, J = 7.1 Hz, 4H), 0.92 (d, J = 6.8 Hz, 3H), 0.88 (s, 3H), 0.69 (s, 3H).<br>LC-MS, theoretical value (C$_{43}$H$_{74}$N$_5$O$_4$, [M + H]$^+$) 724.5741, found: 724.5706.<br>Yield 74%. |

Example 36 Synthesis of Compound C-55

The amidation reaction was carried out by referring to the synthesis of compounds C-47 to C-52. The Boc removing reaction was carried out by referring to the synthesis of compound C-46 to obtain a product in a yield of 50%.

$^1$H NMR (400 MHz, Chloroform-d) 7.84 (d, J=5.9 Hz, 1H), 4.46-4.35 (m, 1H), 3.96 (dd, J=11.0, 2.7 Hz, 1H), 3.81 (d, J=11.2 Hz, 1H), 3.70-3.58 (m, 1H), 3.42 (s, 2H), 3.35-3.27 (m, 3H), 3.23 (dd, J=7.9, 5.3 Hz, 2H), 2.28-2.23 (m, 3H), 1.44 (s, 3H), 1.09 (d, J=7.1 Hz, 4H), 1.00 (d, J=6.8 Hz, 3H), 0.95 (s, 3H), 0.76 (s, 3H).

$^{13}$C NMR (100 MHz, Chloroform-d) δ 173.30, 157.57, 109.74, 81.05, 77.23, 65.14, 62.14, 56.32, 54.32, 51.14, 44.42, 42.61, 40.65, 40.59, 40.27, 36.24, 35.53, 34.84, 34.35, 31.77, 31.53, 28.37, 27.09, 26.91, 26.74, 25.97, 25.76, 25.54, 23.64, 20.67, 16.46, 16.03, 14.32.

LC-MS, theoretical value (C$_{38}$H$_{65}$N$_4$O$_4$, [M+H]$^+$) 641.5006, found: 641.4984.

Example 37 Synthesis of Compound C-55 and Compound C-56

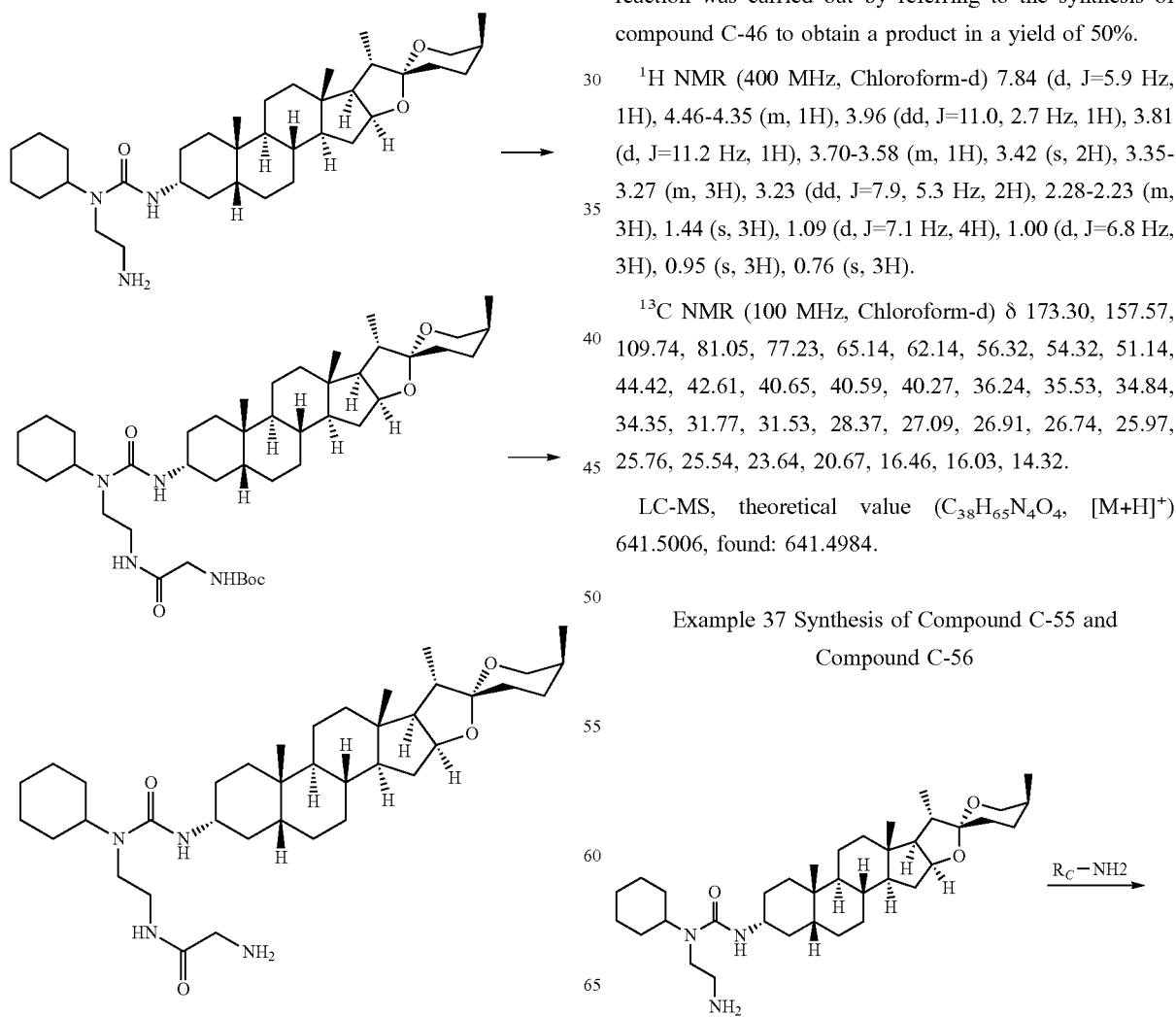

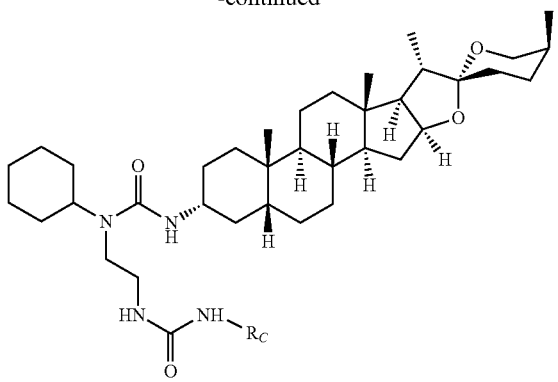

Triphosgene (1 mmol) was dissolved in 60 ml DCM, F3 (1 mmol) was dissolved in 30 ml DCM, and then slowly added dropwise into the reaction system. Triethylamine (2.2 mmol) was dissolved in 30 ml DCM, and then slowly added dropwise into the reaction system. The solvent was evaporated under reduced pressure and the residue was dissolved in 60 ml DCM. A solution of $R_cNH$ (2 mmol) in 30 ml DCM was slowly added dropwise into the reaction system and reacted overnight. The mixture was washed with 1M hydrochloric acid, saturated sodium bicarbonate solution and saturated sodium chloride solution, dried over anhydrous sodium sulfate and separated by silica gel column chromatography to give a compound as shown in Table 4.

TABLE 4

Chemical structure and data of compounds C-55 and C-56

| $R_cNH_2$ | structure of product | Data |
|---|---|---|
| H₂N-CH₃ · HCl | [structure] | $^1$H NMR (400 MHz, Chloroform-d) δ 4.68 (s, 1H), 4.59 (s, 1H), 4.41 (q, J = 7.4 Hz, 1H), 4.00-3.92 (m, 1H), 3.53 (q, J = 10.9, 10.3 Hz, 1H), 3.31 (d, J = 10.9 Hz, 1H), 2.76 (s, 3H), 1.09 (d, J = 7.1 Hz, 4H), 1.00 (d, J = 6.8 Hz, 3H), 0.95 (s, 3H), 0.76 (s, 3H). LC-MS, theoretical value ($C_{38}H_{65}N_4O_4$, [M + H]$^+$) 641.5006, found: 641.4980. Yield: 40%. |
| H₂N-CH₂CH₂-N(CH₃)₂ | [structure] | $^1$H NMR (400 MHz, Chloroform-d) δ 5.70 (t, J = 5.5 Hz, 1H), 5.23 (d, J = 13.9 Hz, 1H), 4.41 (q, J = 7.1 Hz, 1H), 4.06 (s, 7H), 3.95 (d, J = 10.5 Hz, 1H), 3.57-3.44 (m, 1H), 3.39-3.25 (m, 3H), 2.68 (t, J = 5.5 Hz, 2H), 2.44 (s, 5H), 1.26 (s, 4H), 1.08 (d, J = 7.1 Hz, 3H), 0.99 (d, J = 6.5 Hz, 3H), 0.94 (d, J = 4.8 Hz, 3H), 0.75 (s, 3H). Yield: 35%. |

Pharmacology Example

*Anemarrhena asphodeloides* Bge. contains a large amount of saponins, wherein spirostanol sarsasapogenins and sarsasapogenins, such as timosaponin A1, and timosaponin A3 etc., are related to the structure of compound of the present invention. The structural feature of these saponins is that the 3-position substituent is aglycosyl, for example, timosaponin A1 is a 3-position monosaccharide-substituted sapogenin; and timosaponin A3 is a 3-position disaccharide-substituted sapogenin. The compound of the present invention is characterized in that other substituent is linked at the 3-position by a chemical synthesis means.

Animal forced swimming test (FST) and tail suspension test (TST) are two classic antidepressant screening models. Both models are used for screening the compounds of the present invention for antidepressant activity.

The explanations for some of the codes appearing in the table below or in the figure are as follows:

FLX represents fluoxetine,

Fluoxetine represents fluoxetine,

The chemical structures of timosaponin A1, timosaponin A3, sarsasapogenin are as follows:

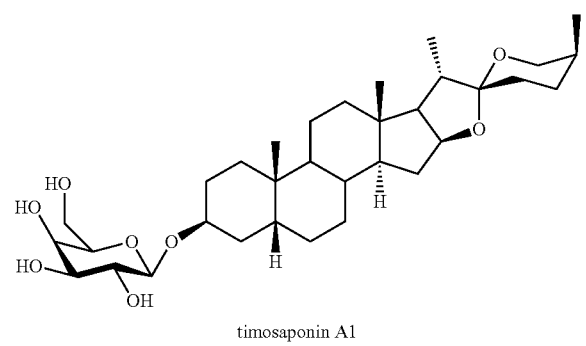

timosaponin A1

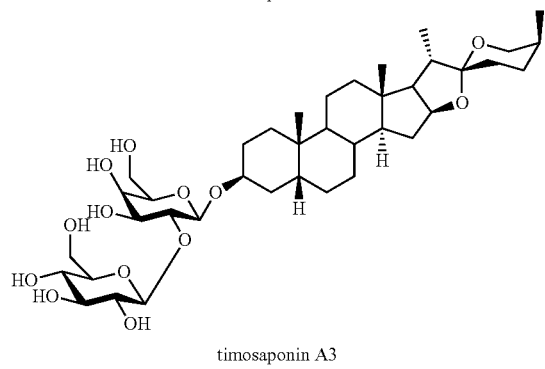

timosaponin A3

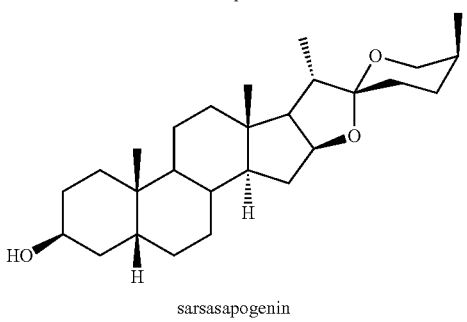

sarsasapogenin

Example 38

Forced swimming test (FST) to investigate the antidepressant activity of some compounds and some natural products of the present invention The specific experimental steps are as follows.

Male ICR mice (body weight, 20±2 g) used in the experiment were purchased from the Experimental Animal Center of Shanghai Institute of Materia Medica, Chinese Academy of Sciences. They were free access to water and kept at room temperature (23 2) ° C. in natural light. All mice were randomly divided into a blank control group and a test group, with 10 mice in each group and 5 mice/cage. The experiment was started after 3 days of adaptation in the breeding environment. The mice were fasted for 12 hours before the experiment but free access to water. The specific administration method was gavage administration, and the administration dose of the administration group was 10 mg/Kg, and the blank control group was given an equal volume of 0.5% CMC-Na.

Specific procedures: The mice were continuously administered for 6 days, and tested 1 hour after the last administration. Firstly, the spontaneous activity of the mice was measured by the open field method, that is, the mice were individually placed in a cylindrical glass jar for 4 minutes, and the number of lifting arms within the last two minutes was recorded. The mice were then individually placed in a cylindrical glass jar (20 cm high and 14 cm in diameter) with a water depth of 10 cm and a water temperature of 23° C. to 25° C. After mice entered into water, a 6-minute timing was conducted, the cumulative immobility time (the criteria for determining immobility: the mice stopped struggling in the water, or floated with only small limb movements to keep the head float on the water) within the last four minutes was recorded. Each group of mice was operated in parallel.

Experimental data processing: The experimental results were expressed as mean standard error (x SD). Statistical analysis was performed using t-test to determine whether it was significant. Firstly, the t-test was performed on the index of autonomous movement, and $P>0.05$ indicated that the autonomous movements of the mice were not affected, so as to avoid the interference of the central stimulant. Then, the t-test was performed on the experimental index of forced swimming to determine whether it had antidepressant effect.

The experimental results were shown in Table 5, Table 6, Table 7, and Table 8.

TABLE 5

Effect of some compounds of the present invention and some natural products on the forced swimming immobility time of ICR mice

| Group | TST cumulative immobility time (mean ± SD, s) |
| --- | --- |
| blank control group | 118.1 ± 41.9 |
| timosaponin A1 | 86.3 ± 47.1 |
| timosaponin A3 | 100.8 ± 43.7 |
| sarsasapogenin | 91.5 ± 45.8 |
| 3-cyclohexyl ureidosarsasapogenin (Example 20) | 62.7 ± 35.6* |
| compound C-11 | 58.9 ± 22.4** |
| compound C-12 | 57.0 ± 31.5* |

*indicates $P < 0.05$;
**indicates $P < 0.01$.

The experimental results of 3-cyclohexyl ureidosarsasapogenin (i.e. the product of Example 2), compound C-11, and compound C-12 were shown in Table 5 and compared with those of the natural products, timosaponin A1, timosaponin A3, sarsasapogenin. The results showed that, compared with the blank group, the naturally occurring compounds astimosaponin A1, timosaponin A3 and sarsasapogenin could not significantly reduce the immobility time of mice in forced swimming test, and the statistical differences were not significant. 3-cyclohexyl ureidosarsasapogenin (Example 20), compound C-11, and compound C-12 all significantly reduced the immobility time of mice in forced swimming test, wherein 3-cyclohexyl ureidosarsasapogenin (Example 20) and compound C-12 had significant antidepressant activity (P<0.05); and compound C-11 had extremely significant antidepressant activity (P<0.01)

TABLE 6

Effect of compound C-13 on immobility time of ICR mice in forced swimming test

| Group | TST cumulative immobility time (mean ± SD, s) |
|---|---|
| blank control group | 154.7 ± 18.8 |
| compound C-13 | 131.1 ± 28.1* |

The experimental results of compound C-13 were shown in Table 6. Compared with the blank group, compound C-13 can significantly reduce the immobility time of mice in the forced swimming test and has significant antidepressant activity (P<0.05).

TABLE 7

Effect of compound C-23 on immobility time of ICR mice in forced swimming test

| Group | TST cumulative immobility time (mean ± SD, s) |
|---|---|
| blank control group | 118.4 ± 37.3 |
| compound C-23 | 94.7 ± 29.8 $^{(P=0.062)}$ |

The experimental results of compound C-23 were shown in Table 7. Compared with the blank group, compound C-23 can reduce the immobility time of mice in the forced swimming test and has certain antidepressant activity.

TABLE 8

Effect of compound C-49 on immobility time of ICR mice in forced swimming test

| Group | TST cumulative immobility time (mean ± SD, s) |
|---|---|
| blank control group | 134.3 ± 25.3 |
| fluoxetine positive control | 100.7 ± 24.1* |
| sarsasapogenin | 127.0 ± 44.4 |
| compound C-49 | 110.8 ± 20.5* |

*indicates P < 0.05;
**indicates P < 0.01.

The experimental results of compound C-49 were shown in Table 8. The results showed that compared with the blank group, sarsasapogenin, in the forced swimming model of mice, could not significantly reduce the immobility time of mice in the forced swimming test, and the statistical differences were not significant; while compound C-49 significantly reduced the time immobility of mice in forced swimming test (P<0.05), and the statistical differences were significant.

Example 39

Tail Suspension Test (TST) to Investigate the Antidepressant Activity of Some Compounds and Some Natural Products of the Present Invention The specific experimental steps were as follows.

Male ICR mice (body weight, 20±2 g) used in the experiment were purchased from the Experimental Animal Center of Shanghai Institute of Materia Medica, Chinese Academy of Sciences. They were free access to water and kept at room temperature (23 2) ° C. in natural light. All mice were randomly divided into a blank control group and a test group, with 10 mice in each group and 5 mice/cage. The experiment was started after 3 days of adaptation in the breeding environment. The mice were fasted for 12 hours before the experiment but free access to water. The specific administration method was gavage administration, and the administration dose was 10 mg/Kg, and the blank control group was given an equal volume of 0.5% CMC-Na.

Specific procedures: The mice were continuously administered for 6 days, and tested 1 hour after the last administration. Firstly, the spontaneous activity of the mice was measured by the open field method, that is, the mice were individually placed in a cylindrical glass jar for 4 minutes, and the number of lifting arms within the last 2 minutes was recorded. Then the tail of the mice was stick onto the horizontal bar by the tape at 2 cm from the tip of the tail, and the animal eyesight was separated by the surrounding plates. The horizontal bar was about 25 cm from the ground, so that the mouse was about 10 cm from the ground, and the timing was 6 min. The cumulative immobility time within the last 4 minutes was recorded. Each group of mice was operated in parallel.

Experimental data processing: The experimental results were expressed as mean standard error (x SD). Statistical analysis was performed using t-test to determine whether it was significant. Firstly, the t-test was performed on the index of autonomous movement, and P>0.05 indicated that the autonomous movements of the mice were not affected, so as to avoid the interference of the central stimulant. Then, the t-test was performed on the experimental index of tail suspension test to determine whether it had antidepressant effect.

The experimental results were shown in Table 9, Table 10, Table 11, Table 12, and Table 13.

The experimental results of 3-cyclohexyl ureidosarsasapogenin (Example 20), compound C-11, and compound C-12 were shown in table 9 and compared with those of the natural products, timosaponin A1, timosaponin A3, and sarsasapogenin.

TABLE 9

Effect of some compounds of the present invention and some natural products on the immobility time of ICR mice in TST

| Group | TST cumulative immobility time (mean ± SD, s) |
|---|---|
| blank control group | 92.0 ± 26.9 |
| timosaponin A1 | 71.9 ± 30.6 |
| timosaponin A3 | 60.6 ± 25.4* |
| sarsasapogenin | 85.4 ± 33.6 |
| 3-cyclohexyl ureidosarsasapogenin (Example 20) | 55.5 ± 42.7* |
| compound C-11 | 56.9 ± 16.6** |
| compound C-12 | 60.0 ± 32.2* |

*indicates P < 0.05;
**indicates P < 0.01.

The results showed that compared with the blank group, the naturally occurring compounds timosaponin A1 and sarsasapogenin could not significantly reduce the immobility time of mouse in tail suspension test, and there was no statistically significant difference. Timosaponin A3, 3-cyclohexyl ureidosarsasapogenin (Example 20), compound C-11, and compound C-12 all significantly reduced the immobility time of the mouse in tail suspension experiment. Wherein, timosaponin A3, 3-cyclohexyl ureidosarsasapogenin (Example 20) and compound C-12 hd significant antidepressant activity (P<0.05); and compound C-11 had extremely significant antidepressant activity (P<0.01).

TABLE 10

Effect of compound C-7 on the immobility time of ICR mice in TST

| Group | TST cumulative immobility time (mean ± SD, s) |
|---|---|
| blank control group | 91.2 ± 38.5 |
| compound C-7 | 54.7 ± 44.9 $^{(P=0.067)}$ |

The experimental results of compound C-7 were shown in Table 10. Compared with the blank group, compound C-7 could reduce the immobility time of the mouse in tail suspension experiment and had certain antidepressant activity.

TABLE 11

Effect of compound C-5 and compound C-20 on the immobility time of ICR mice in TST

| Group | TST cumulative immobility time (mean ± SD, s) |
|---|---|
| blank control group | 104.7 ± 24.3 |
| compound C-5 | 81.1 ± 26.2 $^{(P=0.051)}$ |
| compound C-20 | 79.6 ± 29.5 $^{(P=0.053)}$ |

The experimental results of compound C-5 and compound C-20 were shown in Table 11. Compared with the blank group, compound C-5 and compound C-20 could reduce the immobility time of the mouse in tail suspension experiment and had certain antidepressant activity.

TABLE 12

Effect of compound C-19 on the immobility time of ICR mice in TST

| Group | TST cumulative immobility time (mean ± SD, s) |
|---|---|
| blank control group | 105.3 ± 34.8 |
| compound C-19 | 74.1 ± 30.6 $^{(P=0.079)}$ |

The experimental results of compound C-19 were shown in Table 12. Compared with the blank group, compound C-19 could reduce the immobility time of the mouse in tail suspension experiment and had certain antidepressant activity.

TABLE 13

Effect of some compounds of the present invention on the immobility time of ICR mice in TST

| Group | TST cumulative immobility time (mean ± SD, s) |
|---|---|
| blank control group | 126.2 ± 21.8 |
| fluoxetine | 89.5 ± 28.9* |

TABLE 13-continued

Effect of some compounds of the present invention on the immobility time of ICR mice in TST

| Group | TST cumulative immobility time (mean ± SD, s) |
|---|---|
| sarsasapogenin | 116.6 ± 29.4 |
| compound C-35 | 81.3 ± 47.7* |
| compound C-42 | 116.9 ± 43.3 |
| compound C-46 | 118.0 ± 28.4 |
| compound C-49 | 82.4 ± 43.6* |

*indicates P < 0.05;
**indicates P < 0.01.

The experimental results of compound C-49 and the like were shown in Table 13. The results showed that, compared with the blank group, sarsasapogenin, in the mouse tail suspension model, could not significantly reduce the immobility time of forced swimming in mice, and there was no statistically significant difference; while compound C-35 and compound C-49 could significantly reduce the immobility time of mouse in tail suspension experiment (P<0.05) and there was statistically significant difference.

The anti-depressant comparison test results of some compounds of the present invention and some natural products showed that the naturally occurring spirostanol timosaponins, timosaponin A1 and sarsasapogenin had no antidepressant effect on both animal models; and timosaponin A3 was only effective in the tail-suspension model, but had no effect on the forced swimming model. It can be seen that the natural product, timosaponin A3, was not very effective for antidepression and had significant toxicity (Acta Pharmacologica Sinica 2014; 35 (9): 1188-1198).

In the same animal batch for efficacy screenings compared to the above natural products, the compounds of the invention showed significant antidepressant activity in both animal models. In the forced swimming model, both compound C-12 and 3-cyclohexylureidosarsasapogenin (Example 20) of the present invention showed significant antidepressant activity (P<0.05), and compound C-11 had extremely significant antidepressant activity (P<0.01). In the tail suspension model, both compound C-12 and 3-cyclohexylureidosarsasapogenin (Example 20) of the present invention showed significant antidepressant activity (P<0.05), and compound C-11 had extremely significant antidepressant activity (P<0.01). No significant toxicity was observed for the compounds C-11, 12 and 3-cyclohexylureidosarsasapogenin of the present invention (Example 20).

In other animal batches for antidepressant efficacy screening, compound C-13, compound C-23, compound C-5, compound C-7, compound C-19, and compound C-20 of the present invention also had significant or certain antidepressant activity.

In contrast to the blank group, compound C-49 of the present invention showed significant antidepressant activity (P<0.05) in the forced swimming model. In the tail suspension model, both compound C-35 and compound C-49 of the present invention showed significant antidepressant activity (P<0.05). Moreover, compound C-49 showed significant antidepressant activity in both animal models.

Example 40

Comparison of Antidepressant Activities of Compound C-11 and Fluoxetine in Mouse Model Specific Experimental Operation Forced Swimming Test The mice were placed in a cylindrical jar 24 hours before administration to accommodate the underwater environment for 15 min. On the day of the behavioral test, animals were administered twice and administered orally 4 h and 1 h before the behavioral test. The mice were individually placed in a cylindrical glass jar, timed for 6 minutes, and the number of arm lift was recorded within the last 2 minutes. The mice were then placed in a cylindrical glass jar having 30 cm high and 20 cm in diameter. The water depth in the glass jar was 15 cm (for the rat, water depth was 20 cm), so that the animal could not escape the glass jar, and the feet and tail did not contact with the bottom of the jar. Water temperature was 23° C.-25° C. After the mice entered into the water, a 6-minute video was taken. Since most animals were very active at the beginning of two minutes, the immobility time within the last 4 minutes was calculated (determination standard for immobility: the mice stopped struggling in the water, did not move or had small limb movement for maintaining balance or floating state). Each group of mice was operated in parallel.

Tail Suspension Test

On the day of the behavioral test, animals were dosed twice and administered orally 4 h and 1 h before the behavioral test. During the experiment, the tail of the mouse was hung on a tail suspension test stand about 15 cm away from the ground with a tape or a clip at about 1 cm away from the tail end. The mice struggled to overcome the abnormal posture, but appeared intermittent immobility after a period of activity showing disappointment state. The experimental time for each group was 6 minutes. Since most of the mice struggled actively for the first two minutes, the immobility time within the last four minutes was recorded.

The experimental results showed that compound C-11 significantly reduced the cumulative immobility time of mice in the forced swimming test (p<0.05) and significantly reduced the immobility time of mice in tail suspension test (p<0.05), showing antidepressant activity. Moreover, the effective dose of compound C-11 was significantly lower than that of the positive drug fluoxetine, and the effective dose of compound C-11 was only half of that of fluoxetine.

The results of the mouse swimming test were shown in FIG. 1. Compared with the blank group, compound C-11 significantly reduced the cumulative immobility time of mice (p<0.05) in the forced swimming test, showing antidepressant activity. Moreover, the effective dose of compound C-11 was significantly lower than that of the positive drug fluoxetine, and the effective dose was only half of that of fluoxetine.

Figure 2:
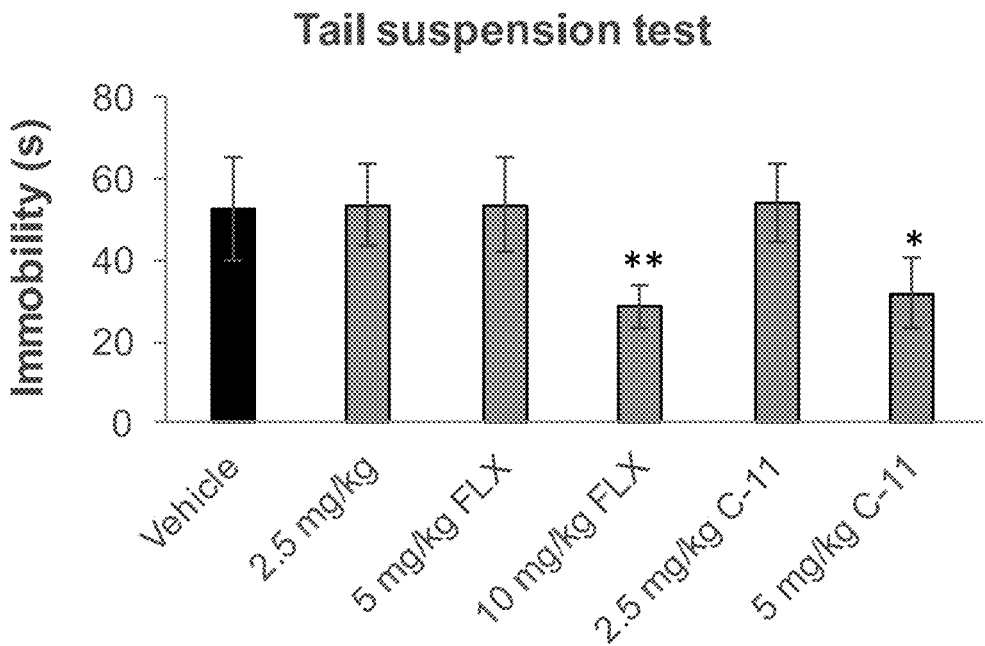
FIG. 2 is a graph showing the effect of gavage administration of example 29 on the immobility time of ICR mouse in tail suspension test ("*" indicates P<0.05; "**" indicates P<0.01).

The results of the mouse tail suspension test were shown in FIG. 2. Compared with the blank group, compound C-11 significantly reduced the cumulative immobility time of the mouse in tail suspension test (p<0.05), showing antidepressant activity. Moreover, the effective dose of compound C-11 was significantly lower than that of the positive drug fluoxetine, and the effective dose was only half of that of fluoxetine.

Example 41

Comparison of Antidepressant Activities of Compound C-11 and Fluoxetine in Rat Model Specific Experimental Operation Forced Swimming Test The rats were placed in a cylindrical jar 24 hours before administration to accommodate the underwater environment for 15 min. On the day of the behavioral test, animals were administered twice and administered orally 4 h and 1 h before the behavioral test. The rats were individually placed in a cylindrical glass jar, timed for 6 minutes, and the number of arm lift was recorded within the last 2 minutes. The rats were then placed in a cylindrical glass jar having 30 cm high and 20 cm in diameter. The water depth in the glass jar was 20 cm, so that the animal could not escape the glass jar, and the feet and tail did not contact with the bottom of the jar. Water temperature was 23° C.-25° C. After rat entered into the water, a 6-minute video was taken, since most animals were very active at the beginning of two minutes, the immobility time within the last 4 minutes was calculated (determination standard for immobility: the state of the rat in the water was classified as three states: immobility, swimming and climbing, the equal scores of these three states were counted every 5 seconds, a total of 5 minutes, a total of 60 times).

Tail Suspension Test

On the day of the behavioral test, animals were dosed twice and administered orally 4 h and 1 h before the behavioral test. During the experiment, the tail of the rat was hung on a tail suspension test stand about 15 cm away from the ground with a tape or a clip at about 1 cm away from the tail end. The rats struggled to overcome the abnormal posture, but appeared intermittent immobility after a period of activity showing disappointment state. The experimental time for each group was 6 minutes. Since most of the rats struggled actively for the first two minutes, the immobility time within the last four minutes was recorded.

The experimental results showed that compound C-11 significantly reduced the cumulative immobility time of rats in the forced swimming test (p<0.05) and significantly reduced the immobility time of rats in tail suspension test (p<0.05), showing antidepressant activity. Moreover, the effective dose of compound C-11 was significantly lower than that of the positive drug fluoxetine.

Figure 3:
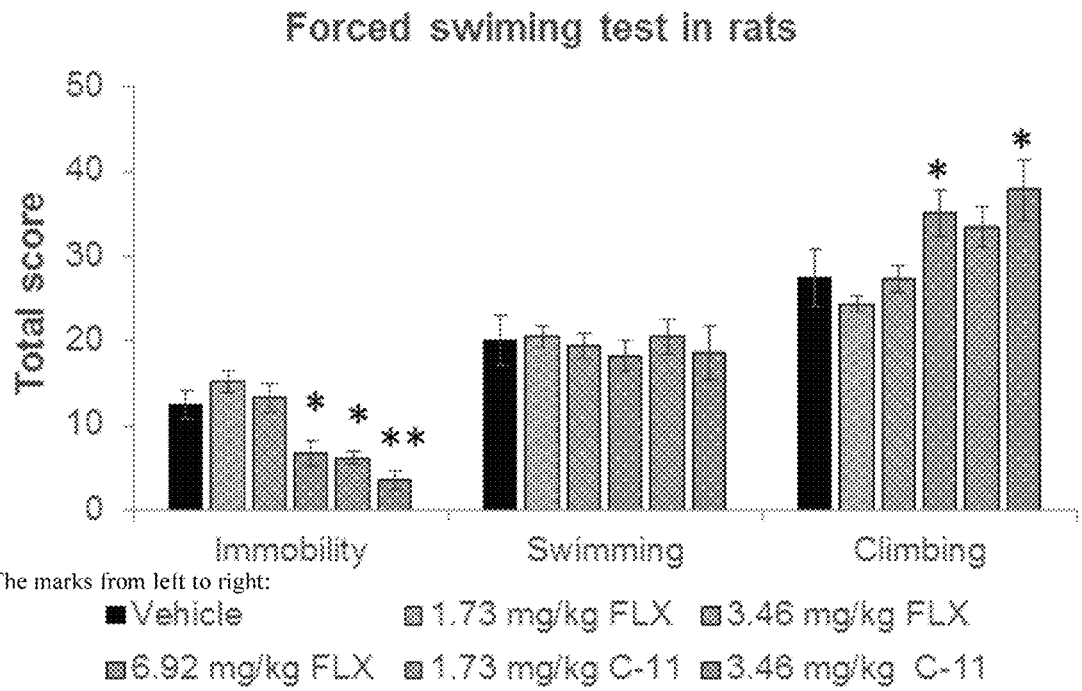
FIG. 3 is a graph showing the effect of gavage administration of example 30 on the immobility time of rat in forced swimming test ("*" means P<0.05; "**" means P<0.01).

The results of the rat swimming test were shown in FIG. 3. In the forced swimming test of rats, the antidepressant activity of compound C-11 was further verified, and the effective dose of compound C-11 was significantly lower than that of the positive drug fluoxetine. Fluoxetine could significantly affect the immobility time and wall climbing behavior of rats only when administered at a dose of 6.92 mg/kg, while the doses of 1.73 mg/kg and 3.46 mg/kg had no effect on these two depression-like behaviors. In contrast, the effective dose of C-11 was small, the doses of 1.73 mg/kg and 3.46 mg/kg could significantly reduce the immobility time of rats in forced swimming test, and the oral dose of 3.46 mg/kg could significantly increases the wall climbing time (*p<0.05, **p<0.01 vs. vehicle group).

Figure 4:
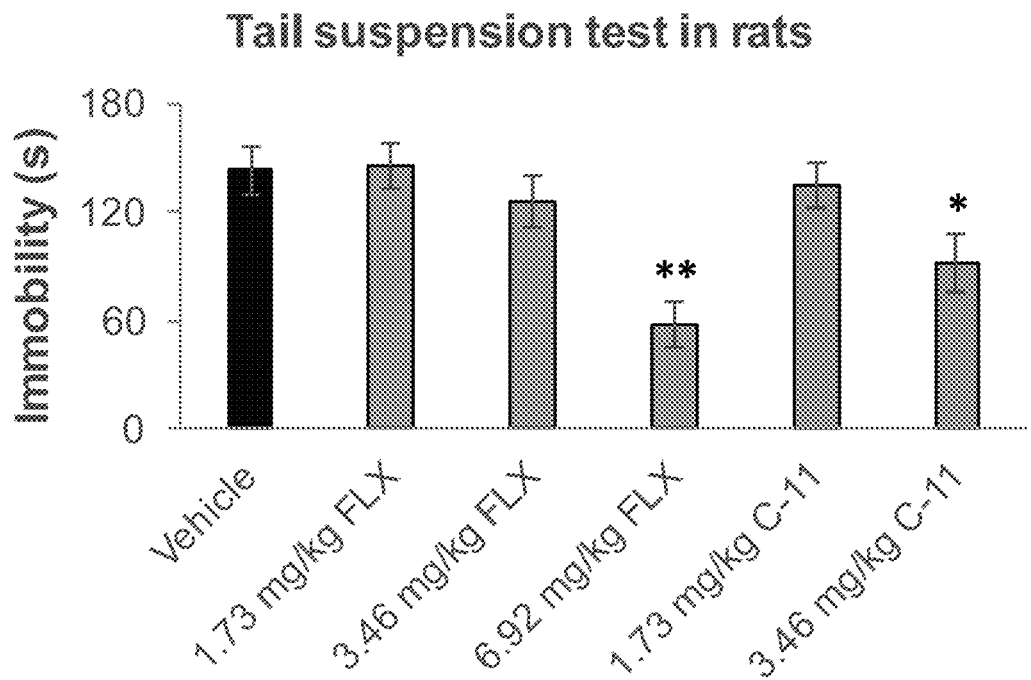
FIG. 4 is a graph showing the effect of gavage administration of example 30 on the immobility time of rat in tail suspension test ("*" means P<0.05; "**" means P<0.01).

The results of the rat tail suspension test were shown in FIG. 4. In the tail suspension test of rats, the antidepressant activity of compound C-11 was also further verified, and the effective dose of compound C-11 was significantly lower than that of the positive drug fluoxetine. Fluoxetine could significantly affect the cumulative immobility time of rats in the tail suspension test only when administered at a dose of 6.92 mg/kg, while the doses of 1.73 mg/kg and 3.46 mg/kg had no effect on these two depression-like behaviors. In contrast, the effective dose of C-11 was small, the doses of 3.46 mg/kg could significantly reduce the cumulative immobility time of rats in tail suspension test (*p<0.05, **p<0.01 vs. vehicle group).

Example 42

Investigate the Antidepressant Activity of the Compounds of the Present Invention in Social Defeated Stress (SDS) Model The test results showed that compound C-11 showed superior antidepressant activity to fluoxetine in this model.

The specific experimental operation was as follows.

Male CD-1 aged 4-6 months mice which had passed childbearing age were raised separately, allowed to eat freely and adapt to the environment for about one week. Male C57 mice (aged 8-20 weeks differently) were used to screen for aggressive CD-1 mice. The mice screened by C57 were placed directly in the cage of CD-1 for 3 minutes, and the latency period for CD-1 to start showing offensive was recorded, and then the mice screened by C57 were moved out. For each CD-1 mouse, the same C57 was used to screen it three times a day, and different C57-selected mice were selected every day for a total of three days of screening. The mice having offensive were selected based on the aggressive latency period of each CD-1 mouse, wherein CD-1 mouse must exhibit attacking in at least two consecutive sessions within three 3-minute contact sessions of each day and it must exhibit less than 1 minute of aggressive latency period during each 3-minute contact session. After screening for CD-1 aggressive mice for modeling, each C57 test mouse was exposed to different CD-1 aggressive mice for 10 consecutive days, 10 minutes each day. During transient exposure, all test mice exhibited stress and compliance characteristics including vocalization, escape response, and compliance posture. After 10 minutes of contact, the test mice were isolated from the invaders. Test mice and aggressive mice were placed in adjacent sections of the same squirrel cage, separated by a porous transparent plastic baffle, allowing test mice to be exposed under a threatening chronic stress stimulation for the next 24 hours. The control mice were placed in cages having the same structure, but the other side of the baffle was placed with other mice of the same line that were replaced daily. After 24 hours after the end of the last day of the experiment, we evaluated CSDS-induced social behavioral changes and selected all susceptible mice based on previous reports. The social interaction ratio (SI ratio) was calculated according to the following formula: SI ratio=time for the mouse in the interaction area when the aggressor exists/time for the mouse in the interaction area when the aggressor is absent. If the SI ratio was less than 1, it indicated that the test mice had less time in the interactive area in the presence of the invader than in the absence of the aggressor, and it was used as criteria and threshold for identifying susceptible mice. All selected test mice and control mice were then housed individually for 3 weeks. During this period, susceptible mice were randomly divided into three groups: DEFEAT depression model group was administered by gavage with 0.5% CMC-Na every day, C-11 administration group was administered by gavage with 10 mg/kg C-11 every day, and the FLX administration group was administered with 10 mg/kg fluoxetine intraperitoneally every day. The mice in the vehicle group were administered by gavage with 0.5% CMC-Na every day. The SI ratio was assessed once a week.

All data were analyzed using spss 22 (for mac) data processing software. Two-way ANOVA was used to analyze and LSD method was used for the multiple comparisons of calibration results. The data were expressed in Mean sem. One asterisk was marked when p<0.05; and two asterisks were marked when p<0.01.

Figure 5:
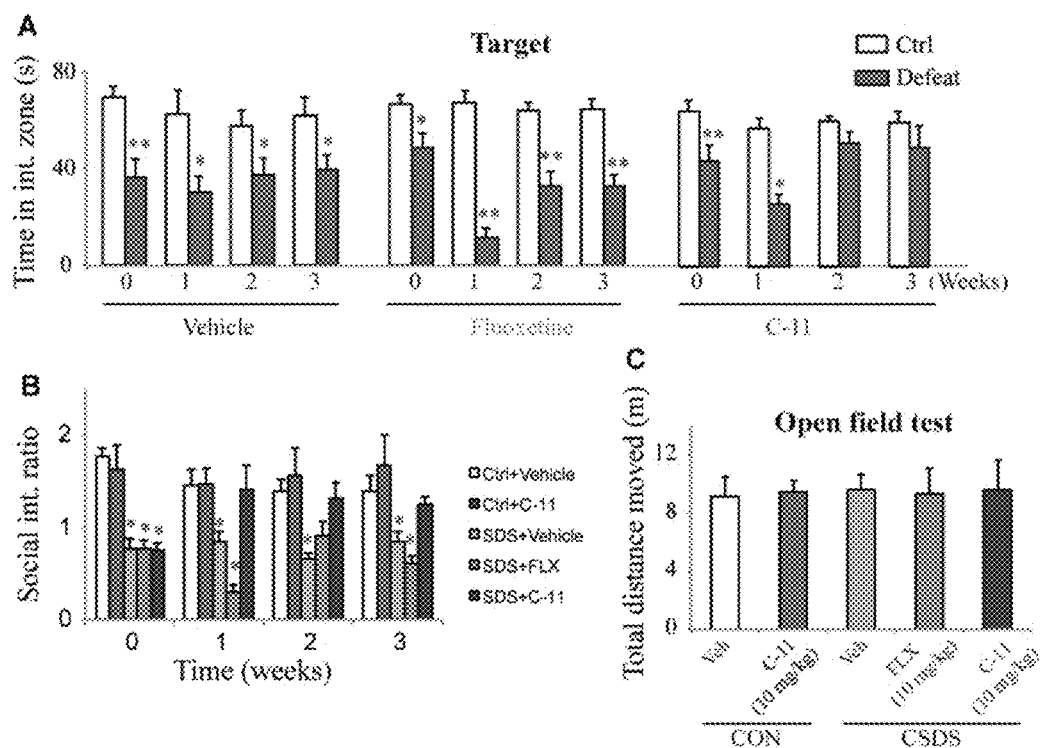
FIG. 5 is a graph showing the effect of the compound C-11 administered by the gavage on the social failure depression animal model in example 31 ("*" indicates P<0.05; "**" indicates P<0.01).

The test results were shown in FIG. 5. FIG. 5A illustrated the pharmacodynamic evaluation of mouse model of social defeated stress, and the mouse social time was calculated. The results showed that C-11 significantly increased the social time of the mice during the second week of administration, while fluoxetine did not work during the third week of administration. FIG. 5B showed the social proportion of mice, the larger the value, the better the social behavior of the animals. The results further suggested that C-11 could effectively increase the social activity of mice in the first week of administration, while fluoxetine was not effective after three weeks of administration. FIG. 5C showed the results of the open field experiment, and there was no significant change in the moving distance between the animals in each group, suggesting that there was no difference in the exercise ability of each group of animals, and it would not affect social behavior. These results suggested that oral administration of C-11 for 1-2 weeks could effectively alleviate depressive symptoms, and the onset time thereof was significantly faster than that of fluoxetine.

Example 43

Investigation on Bioavailability of Compound C-49

The specific experimental procedures were as follows. The healthy male SD rats (about 270 g) were fasted for 10 h before administration, and were free to drink water. Compound C-49 (CMC-Na solvent suspension) was administered by gavage at a dose of 100 mg/kg rat body weight. The time points of blood collection from the eye socket were 30 min, 1 h, 2 h, 4 h, 6 h, 8 h, 10 h, 24 h, 48 h after the administration (n=5). The tail vein was injected with C-49 (a solution was prepared with 10% ethanol/15% Tween 80/75% normal saline) at a dose of 1 mg/kg rat body weight. The time points of blood collection from the eye socket were 5 min, 10 min, 30 min, 1 h, 2 h, 4 h, 8 h (n=4). The plasma was placed in a heparin-coated centrifuge tube, centrifuged for 10 min (8000 r), and the supernatant was taken and stored in a −80° C. refrigerator. After acetonitrile precipitation treatment, it was detected by HPLC-QQQ. The pharmacokinetic parameters, PK parameters of each mouse were calculated by a non-compartmental model of WinNonlin (Pharsight 6.2, NC, USA). All parameters were represented with Mean S.D.

$$\text{Bioavailability } (F) = (AUC_{Oral}/Dose_{Oral})/(AUC_{tail\ vein}/Dose_{tail\ vein})$$

Figure 6:
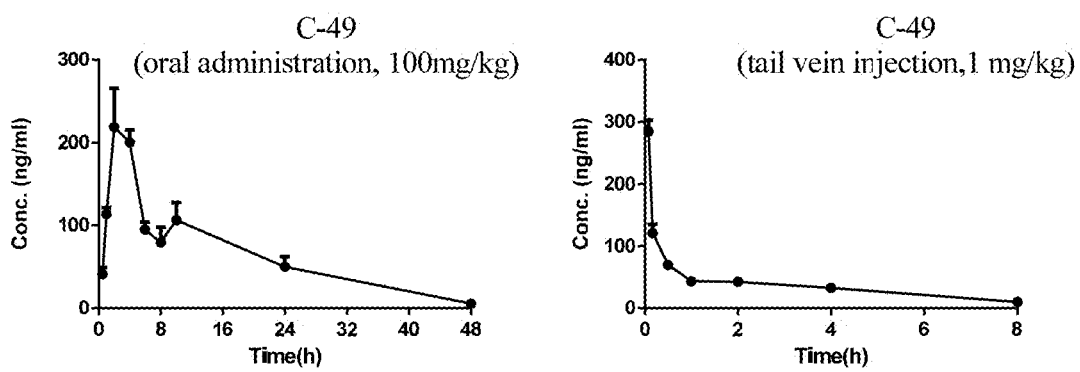
FIG. 6 is a drug-time curve after the compound C-49 was administered orally to the rat or injected into the tail vein of the rat, respectively.

The drug-time curve was shown in FIG. 6, and the pharmacokinetic parameters were shown in the following Table 14.

TABLE 14

| | Pharmacokinetic parameters of oral and tail vein injection of C-49 in rats | |
|---|---|---|
| Dose (mg/kg) | intravenous administration (1 mg/kg) | oral administration (100 mg/kg) |
| $C_{max}$ (ng/ml) | 284.7 ± 41.4 | 250.8 ± 86.9 |
| $T_{max}$ (h) | 0.1 ± 0.0 | 2.8 ± 1.1 |
| MRT (h) | 2.5 ± 0.3 | 13.6 ± 2.5 |

TABLE 14-continued

Pharmacokinetic parameters of oral and tail vein injection of C-49 in rats

| Dose (mg/kg) | intravenous administration (1 mg/kg) | oral administration (100 mg/kg) |
|---|---|---|
| $T_{1/2}$ (h) | 3.0 ± 1.1 | 9.7 ± 2.7 |
| AUC (h*ng/ml) | 293.0 ± 17.1 | 3115.3 ± 525.9 |
| F (%) |  | 11.1 |

The experiment results showed that the plasma concentration was high after the rats were orally administered with C-49 (100 mg/kg), $C_{max}$ and AUC were 250.8 ng/mL and 3115.3 h*ng/mL, respectively, and $T_{1/2}$ and MRT were 9.7 and 13.6 h, respectively. After C-49 (1 mg/kg) was injected into the tail vein of rats, the plasma concentration was low, $C_{max}$ and AUC were 284.7 ng/mL and 293.0 h*ng/mL, respectively, and $T_{1/2}$ and MRT were 9.7 and 13.6 h, respectively. The bioavailability of C-49 was calculated to be 11.1% by comparing the AUC/Does of C-49 administered orally and injected tail vein in rats.

In nature, the anti-depressant activities of spirostanol sarsasapogenin and sarsasapogenin thereof were weak, and the bioavailability was relatively low. Compounds C-11, C-49 and the like obtained by structural modification of sarsasapogenins in the present application had better anti-depressant activity than the lead compound sarsasapogenins. Moreover, the bioavailability of compound C-49 was 11.1%, which was also greatly improved.

Example 44

Pharmacodynamic Screening Study on the Improvement Effect of Compound C-49 on Learning and Memory in Mice Learning memory is an advanced function of the human and animal brains. In this screening test, it was possible to initially evaluate whether the candidate drugs could improve learning and memory by comparing the passive avoidance behavior of the administered mice and memory-impaired mice. In this experiment, ethanol was used to induce the memory reproduction disorder in mice and the role of candidate drug C-49 in promoting learning and memory was preliminarily explored. The experimental principle was that ethanol has a central inhibitory effect and inhibited the neurological activity of the cerebral cortex and significantly interfered with the reproduction of memory.

Before the retesting after training, the ethanol solution was administered to the mouse to block the memory reproduction process of the animal, resulting in memory reproduction disorder.

The specific experimental steps were as follows.

Male ICR mice, 16-18 g, were purchased from Shanghai Sippr-BK laboratory animal Co. Ltd.

Animal feeding: Animals were fed with standard sterilized rat feed, animal drinking water was supplied by drinking water bottle, and animals were free to drink water. Animal raising: Each cage contained 10 animals. The animals were kept at room temperature of 20° C. to 22° C., humidity of 40% to 70%, and illuminated for 12 hours and then kept in darkness. The padding was replaced at least twice a week, and the feeding box was replaced at the same time. When there was an abnormal situation, the feeding box could be replaced at any time. Sterile water bottles and bottle plugs were changed every day and the cage was disinfected once every two weeks. All the cages were autoclaved after being washed.

40 male mice were randomly divided into 4 groups by Excel, and each group contained 10 animals. The mice in group 1 (blank group) and mice in group 2 (model group) were orally administered (i.g.) with drinking water daily. The mice in group 3 (positive drug group) were administered (i.g.) with 1.6 mg/kg of donepezil, and the mice in group 4 were administered intragastrically with the corresponding C-49 solution at a dose of 15 mg/kg, once a day, 0.2 mL/10 g body weight/time, and continuously administered for 3 weeks.

After 3 weeks of administration, 1 hour after the last administration, the exercise was performed once in the dark avoidance method. The mice were placed in a dark avoidance box, and placed in the bright room with the back facing the hole. At the same time, the video analysis device was activated, and the animal passed through the hole into the dark room and received an electric shock, and the timing was automatically stopped. The mice were removed and the screen analysis would record the time required for each mouse to experience an electric shock from the bright room to the dark room, which was the latency period. After 24 h, the test was carried out, and 45% ethanol solution (0.1 ml/10 g) was orally administered 30 min before the test. The video analysis system would automatically record all relevant data of the animal. Data were expressed as mean standard deviation ($\bar{x}$±s), and data difference statistics were analyzed by one-way variance (ANOVA) or $X^2$ test. The difference between groups was judged by P<0.05.

Figure 7:
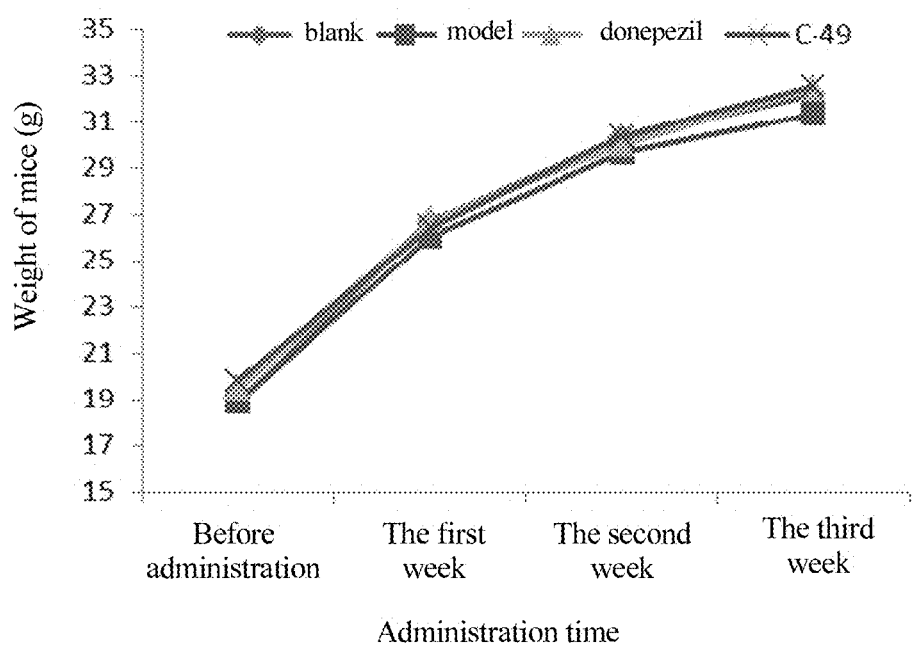
FIG. 7 is a graph of weight gain.

The experimental results showed that no abnormal state of the mice was observed after 15 mg/kg of C-49 was administered by oral gavage. The mice were weighed and recorded weekly during the period. All animals showed no abnormal weight gain within 21 days of the administration period. The growth of animal weight was shown in FIG. 7. The experimental results of the candidate drug C-49 administered to mice for memory reproduction disorder caused by ethanol for three consecutive weeks were shown in Table 15.

TABLE 15

Effect of administration (i.g.) for three consecutive weeks on memory reproduction disorder caused by ethanol ($\bar{x}$ ± s, n = 10)

| Group | Administration | Latency period from an open room to a dark room (s) | Total number of errors (within 5 min) | Number of shocked animals |
|---|---|---|---|---|
| Blank | potable water | 232.7 ± 117.0* | 4* | 3* |
| model | potable ate | 81.7 ± 112.4 | 24 | 8 |
| donepezil | 1.6 mg/kg | 220.1 ± 130.5* | 6 | 2* |
| C-49 | 15 mg/kg | 215.8 ± 135.8* | 3** | 3* |

**P < 0.01;
*P < 0.05, compared with the model group

The experimental results in Table 15 showed that 45% of ethanol, which was administered to mice 24 hours after training, caused significant memory reproduction disorder (compared with the blank group, all showed statistically significant difference), which proved successful modeling. Compared with the model group mice, continuous administration of 1.6 mg/kg of donepezil and 15 mg/kg of C-49 for three weeks significantly prolonged the latency period of the mice into the darkroom and reduced the total number of electric shocks of the mice within 5 minutes, and significantly reduced number of animals subjected to electric shock (P<0.01 or 0.05). The experiments showed that C-49 (15 mg/kg) had a significant improvement effect on learning and memory of the mice having memory reproduction disorder induced by ethanol. At the same time, administration for three consecutive weeks at this dose did not show any significant toxic effects in the mice. For the ethanol-induced animal memory impairment model, C-49 showed good safety and significant pharmacodynamic effects in the experiment.

All documents mentioned in the present application are hereby incorporated by reference in their entirety, just as each document is cited separately as a reference. In addition, it should be understood that various modifications and changes may be made by those skilled in the art after reading the above teachings of the present invention. These equivalent forms also fall within the scope defined by the claims appended hereto.

The invention claimed is:

1. A compound of formula (I), or a pharmaceutically acceptable salt, a solvate, an optically pure isomer or a stereoisomer thereof, or a mixture thereof,

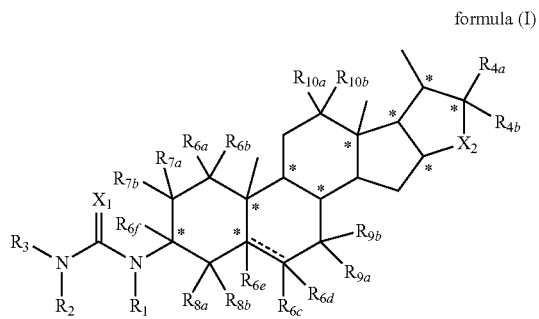

formula (I)

wherein the compound of formula (I) is formed by linking the following fragment A and fragment B,

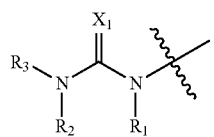

fragment A

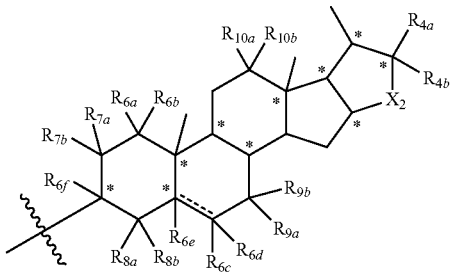

fragment B wherein, $R_1$, $R_2$ and $R_3$ are each independently selected from the group consisting of H, alkyl, substituted alkyl, arylalkyl, substituted arylalkyl, cycloalkyl, substituted cycloalkyl, alkenyl, substituted alkenyl, alkynyl, substituted alkynyl, aryl, substituted aryl, heteroaryl, substituted heteroaryl, heterocyclyl, and substituted heterocyclyl, provided that $R_2$ or $R_3$ is other than an adamantyl; or $R_2$, $R_3$ and attached N together form 3-7 membered saturated or unsaturated heterocycle containing 1-3 N, 0-2 O and/or 0-2 S atoms, wherein the "heterocycle" is unsubstituted, monosubstituted or polysubstituted by the following group(s): H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclyl, substituted heterocyclyl, alkanoyl, substituted alkanoyl, alkoxycarbonyl, arylalkoxycarbonyl, alkylsulfonyl, alkylsulfinyl, arylsulfonyl, arylalkylsulfonyl, carbamoyl, substituted carbamoyl, carboxyl, amido, substituted amido, sulfonamido, and substituted sulfonamide;

$R_{4a}$ and $R_{4b}$ are each independently selected from the group consisting of hydrogen, hydroxy, alkyl, substituted alkyl, alkenyl, substituted alkenyl, alkynyl, and substituted alkynyl; or $R_{4a}$, $R_{4b}$ and attached C together form 3-7 membered saturated or unsaturated heterocycle containing 0-3 N, 0-2 O and/or 0-2 S atoms, wherein the "heterocycle" is unsubstituted, monosubstituted or polysubstituted by the following group(s): hydrogen, hydroxy, alkyl, substituted alkyl, alkenyl, substituted alkenyl, alkynyl, and substituted alkynyl;

$X_1$ is O, S or $NR_5$, $R_5$ is selected from the group consisting of hydrogen, alkyl, cyano, hydroxy, and alkoxy;

$X_2$ is O or NH;

$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$, and $R_{10b}$ are each independently selected from the group consisting of absent, hydrogen, halogen, alkyl, substituted alkyl, hydroxy, mercapto, alkylmercapto, alkoxy, substituted alkoxy, amino, substituted amino, alkylamino, substituted alkylamino, disubstituted amino, alkylacyloxy, arylacyloxy, heteroarylacyloxy and glycosyl; or $R_{6a}$ and $R_{6b}$, $R_{7a}$ and $R_{7b}$, $R_{8a}$ and $R_{8b}$, $R_{9a}$ and $R_{9b}$, and/or $R_{10a}$ and $R_{10b}$ are combined with each other to form carbonyl;

"═" represents a single bond or double bond; and each * independently represents a racemic, S or R configuration.

2. The compound of claim 1, wherein $R_2$ and $R_3$ are each independently selected from the group consisting of H, cycloalkyl, substituted cycloalkyl, heterocyclyl, substituted heterocyclyl, aryl, substituted aryl, and -$MX_3PX_5Q$, wherein, M is alkylenyl, substituted alkylenyl, cycloalkylenyl, or substituted cycloalkylenyl;

$X_3$ is O, S, $(CH_2)_r$, NRa or absent, Ra is selected from the group consisting of H, alkyl, substituted alkyl, alkenyl, substituted alkenyl, alkynyl, substituted alkynyl, aryl, substituted aryl, heteroaryl, substituted heteroaryl, heterocycle, and substituted heterocycle, r=1, 2, 3, 4 or 5;

P is C=O, C=S, C=$NR_b$, C=C $(R_c)$ $(R_d)$ or absent, $R_b$ is selected from the group consisting of H, hydroxy, alkoxy, cyano, and nitro, $R_c$ and $R_d$ are each independently selected from the group consisting of H, alkyl, hydroxy, alkoxy, cyano, and nitro;

$X_5$ is O, S, $(CH_2)_m$, NRe or absent, Re is selected from the group consisting of H, alkyl, and substituted alkyl, m=1, 2, 3, 4 or 5;

Q is H, hydroxy, alkoxy, aryloxy, $NR_fR_g$, alkyl, substituted alkyl, aryl, substituted aryl, heteroaryl, substituted heteroaryl, heterocyclyl, or substituted heterocyclyl, $R_f$ and $R_g$ are each independently H, hydroxy, alkyl, alkoxy, substituted alkyl, alkenyl, substituted alkenyl, alkynyl, substituted alkynyl, alkoxycarbonyl; or $R_f$ and $R_g$ and attached N together form 3-7 membered saturated or unsaturated heterocycle containing 1-3 N, 0-2 O and/or 0-2 S atoms, wherein the "heterocycle" is unsubstituted, monosubstituted or polysubstituted by the following group(s): H, hydroxy, amino, alkyl, substituted alkyl, alkenyl, substituted alkenyl, alkynyl, or substituted alkynyl.

3. The compound of claim 1, wherein $R_2$ is H, $R_3$ is alkyl, substituted alkyl, cycloalkyl, substituted cycloalkyl, aryl, substituted aryl, heteroaryl, substituted heteroaryl, heterocycle, or substituted heterocycle; or $R_2$, $R_3$ and attached N together form the following structure:

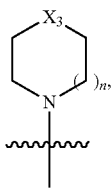

wherein, $X_3$ is C=O, $CH_2$, O or $NR_{11}$, $R_{11}$ is selected from the group consisting of alkyl, substituted alkyl, arylalkyl, substituted arylalkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, alkanoyl, substituted alkanoyl, alkoxycarbonyl, aryl alkoxycarbonyl, carbamoyl, substituted carbamoyl, carboxyl, alkylsulfonyl, alkylsulfinyl, arylsulfonyl, arylalkylsulfonyl, amido, substituted amido, sulfonamido, and substituted sulfonamide;

n=0, 1 or 2.

4. The compound of claim 1, wherein the fragment B is selected from the group consisting of:

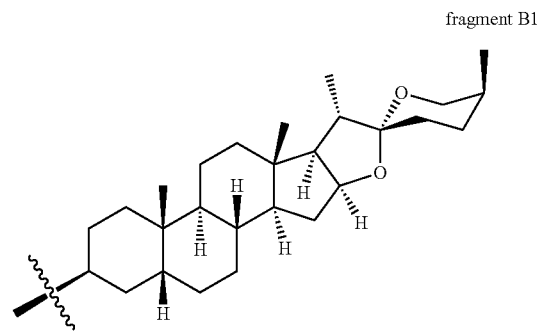

fragment B1

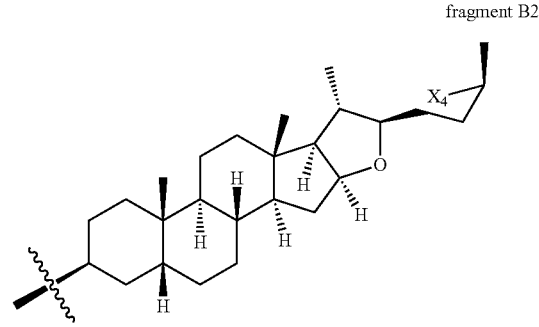

fragment B2

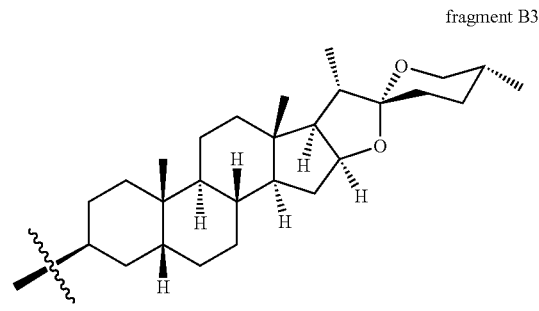

fragment B3

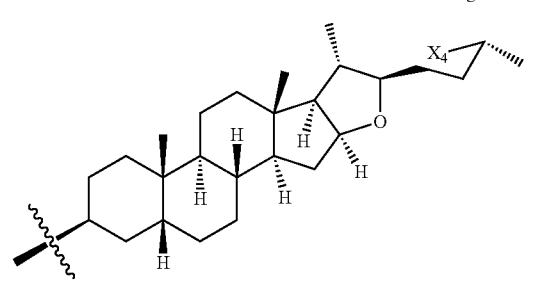

fragment B4

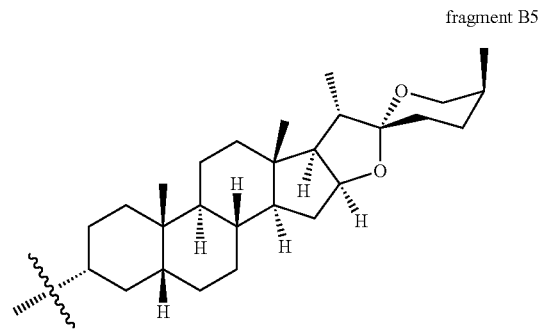

fragment B5

-continued
fragment B6
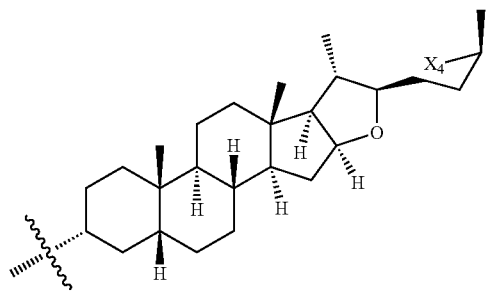
fragment B7
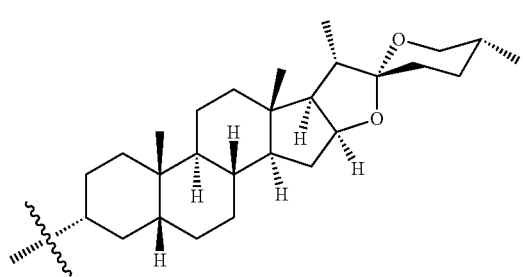
fragment B8
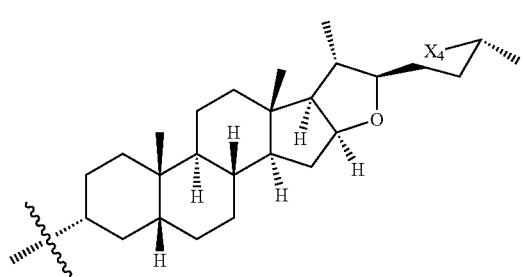
fragment B9
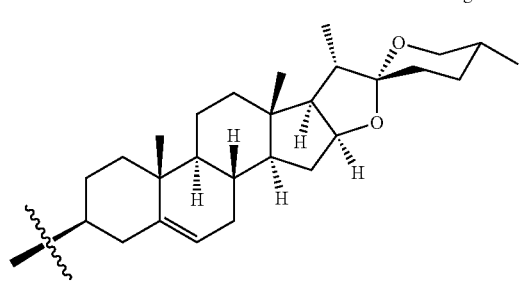
fragment B10
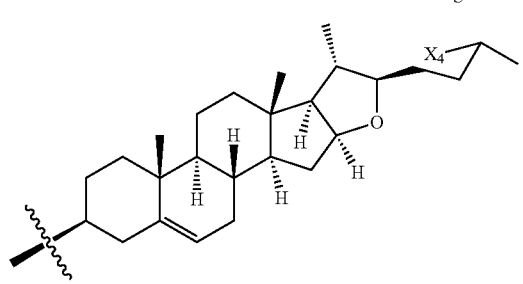
-continued
fragment B11
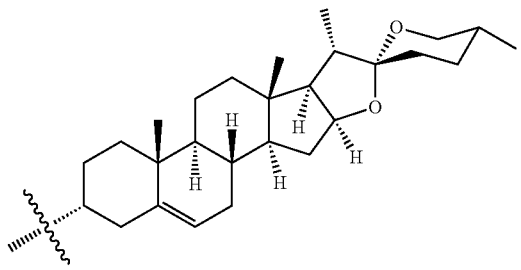
fragment B12
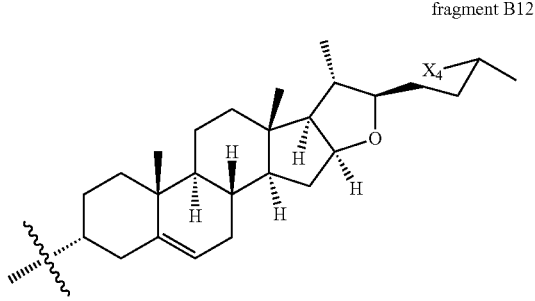
fragment B13
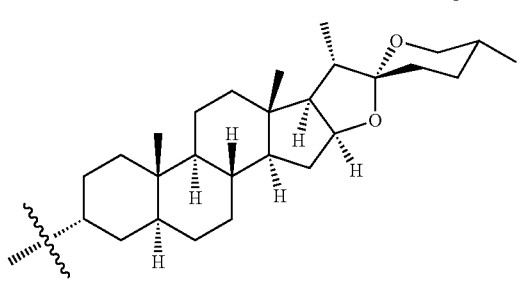
fragment B14
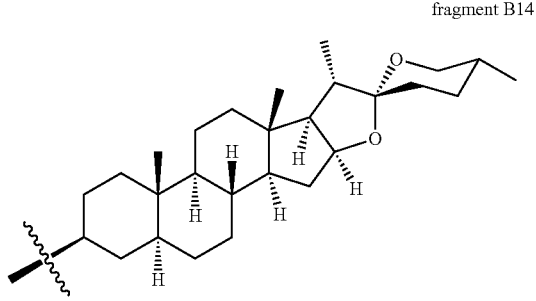
fragment B15
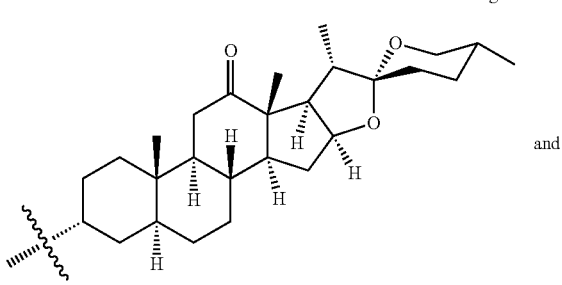
and fragment B16

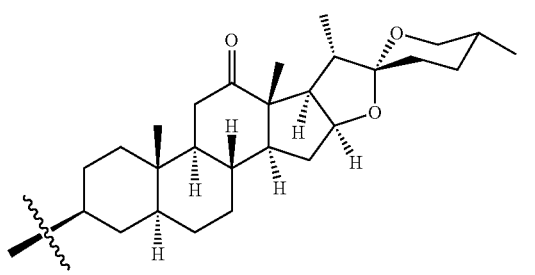

wherein, $X_4$ is $CH_2OR_{12}$, $CH_2N(R_{13})(R_{14})$, aldehyde group, $COOR_{12}$, or $CON(R_{13})(R_{14})$; $R_{12}$, $R_{13}$ and $R_{14}$ are each independently selected from the group consisting of H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocycle, substituted heterocycle, alkanoyl, substituted alkanoyl, alkoxycarbonyl, arylalkoxycarbonyl, alkyl sulfonyl, alkylsulfinyl, aryl sulfonyl, arylalkylsulfonyl, carbamoyl, and substituted carbamoyl.

5. The compound of claim 1, wherein $R_1$, $R_2$, $R_3$ are each independently selected from the group consisting of H, C3-C8 cycloalkyl, C6-C10 aryl, C3-C8 saturated heterocyclyl, and C1-C4 alkyl, wherein cycloalkyl, aryl, saturated heterocyclyl, and alkyl are optionally monosubstituted, disubstituted or trisubstituted with a substituent selected from the group consisting of halogen, hydroxy, C1-C4 alkyl, C6-C10 aryl, and —C(=O)—O—C1-C4 alkyl; or $R_2$, $R_3$ and attached N together form a 3-7-membered saturated or unsaturated heterocycle containing 1-3 N, 0-2 O and/or 0-2 S atoms, wherein the "heterocycle" is unsubstituted, monosubstituted or polysubstituted by the following group(s): H, C1-C4 alkyl, C1-C4 alkoxy, C2-C4 alkenyl, C2-C4 alkynyl, hydroxyl;

$R_{4a}$, and $R_{4b}$ are each independently selected from the group consisting of H, hydroxy, substituted and unsubstituted C1-C6 alkyl, and the term "substituted" means that the group is substituted by one, two or three substituents selected from the group consisting of halogen, hydroxy, C1-C4 alkyl, and C1-C4 alkoxy; or $R_{4a}$, $R_{4b}$ and attached C together form a 3-7 membered saturated or unsaturated heterocycle containing 1-2 O and/or 1-2 S atoms, wherein the "heterocycle" is unsubstituted, monosubstituted or polysubstituted by the following group (s): hydrogen: C1-C4 alkyl, C1-C4 alkoxy, C2-C4 alkenyl, C2-C4 alkynyl, hydroxyl;

$X_1$ is O, S, or $NR_5$, $R_5$ is selected from the group consisting of H, alkyl, and hydroxyl;

$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$, and $R_{10b}$ are absent, H, alkyl, substituted alkyl, hydroxyl or mercapto; or $R6_a$ and $R_{6b}$, $R_{7a}$ and $R_{7b}$, $R_{8a}$ and $R_{8b}$, $R_{9a}$ and $R_{9b}$, and/or $R_{10a}$ and $R_{10b}$ are combined with each other to form carbonyl;

"═" represents a single bond or double bond.

6. The compound of claim 1, wherein $X_1$ is O; $R_1$ is H;
$R_{6a}$, $R_{6b}$, $R_{6c}$, $R_{6d}$, $R_{6e}$, $R_{6f}$, $R_{7a}$, $R_{7b}$, $R_{8a}$, $R_{8b}$, $R_{9a}$, $R_{9b}$, $R_{10a}$, $R_{10b}$ are all hydrogen;
$R_2$, and $R_3$ are each independently selected from the group consisting of H, C3-C8 cycloalkyl, C6-C10 aryl, C3-C8 saturated heterocyclyl, C1-C4 alkyl, wherein cycloalkyl, aryl, saturated heterocyclyl, alkyl are optionally monosubstituted, disubstituted or trisubstituted with a substituent selected from the group consisting of halogen, hydroxy, C1-C4 alkyl, C6-C10 aryl, —C(=O)—OC1-C4 alkyl; or $R_2$, $R_3$ and attached N together form a 3-7 membered saturated or unsaturated heterocycle containing 1-3 N, 0-2 O and/or 0-2 S atoms, wherein the "heterocycle" is unsubstituted, monosubstituted or polysubstituted by the following group (s): H, C1-C4 alkyl, C1-C4 alkoxy, hydroxyl.

7. The compound of claim 1, wherein compound is:

compound C-1

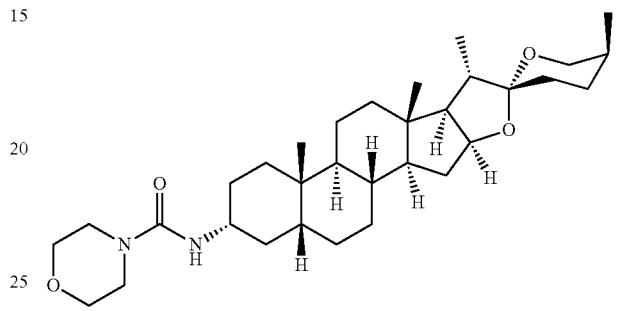

compound C-2

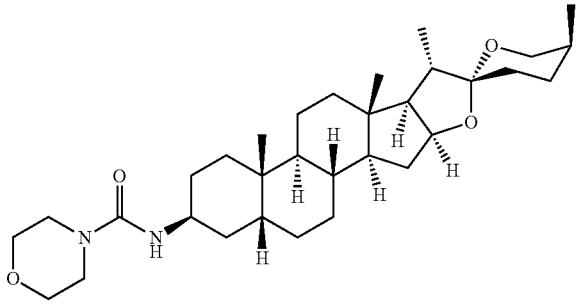

compound C-3

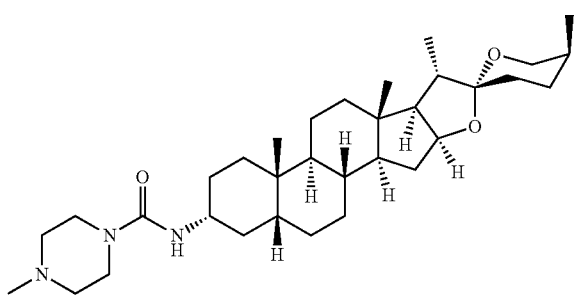

compound C-4

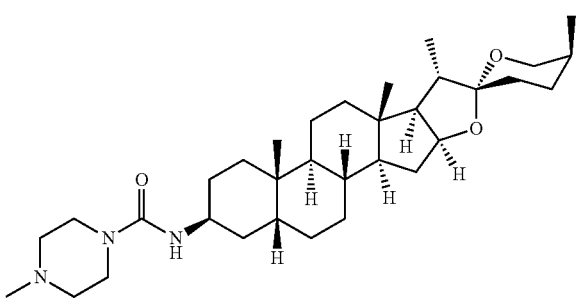

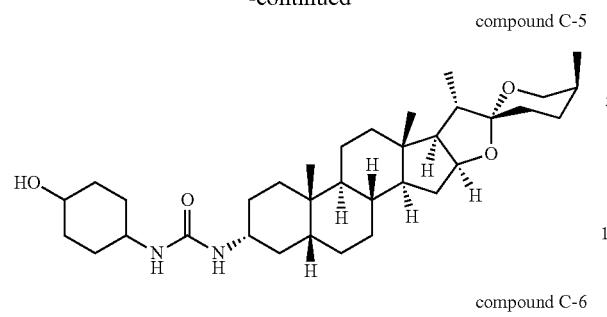
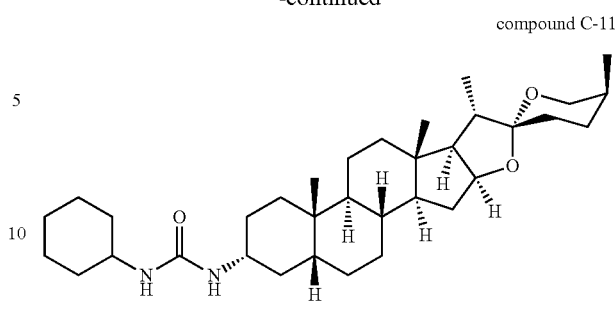

compound C-16
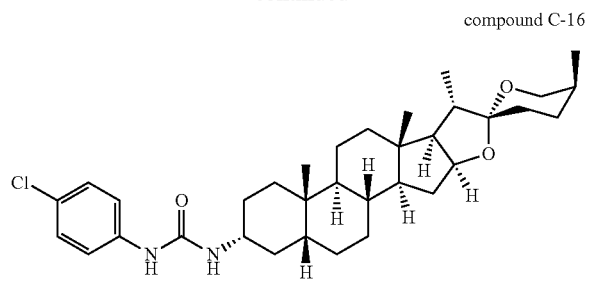
compound C-21
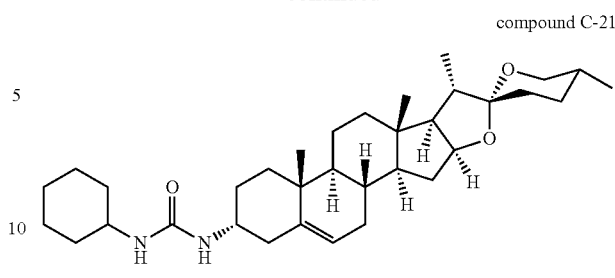
compound C-17
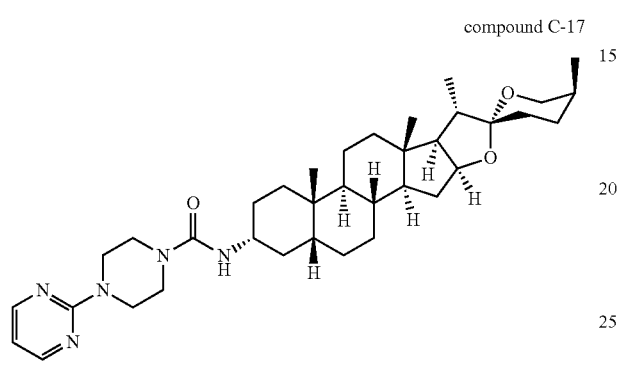
compound C-22
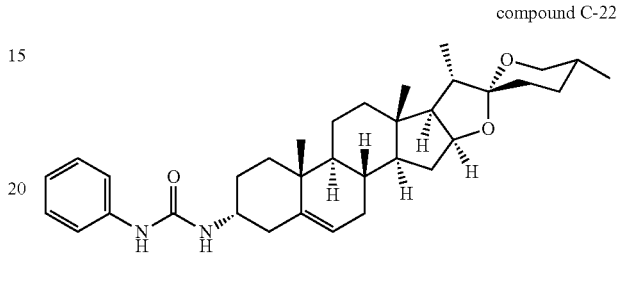
compound C-18
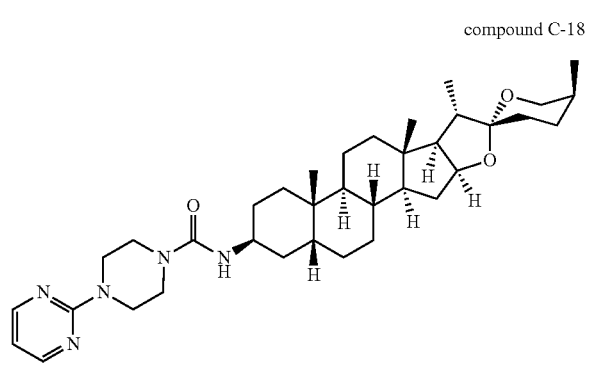
compound C-23
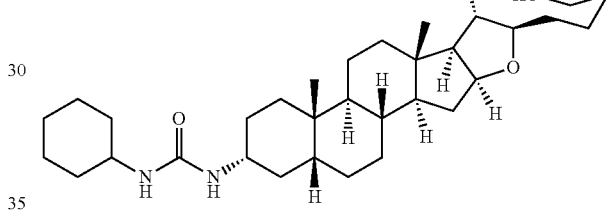
compound C-19
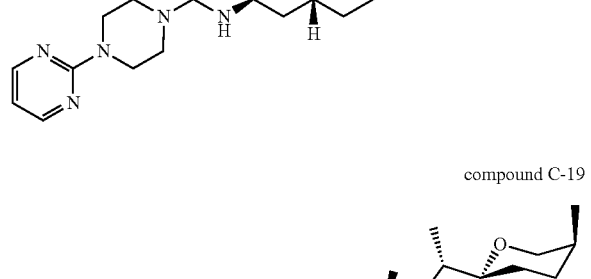
compound C-24
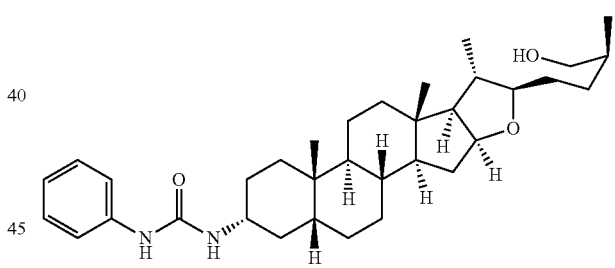
compound C-20
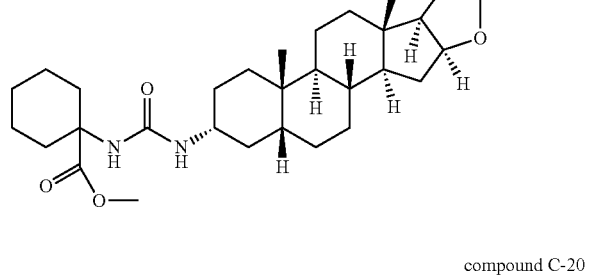
compound C-25
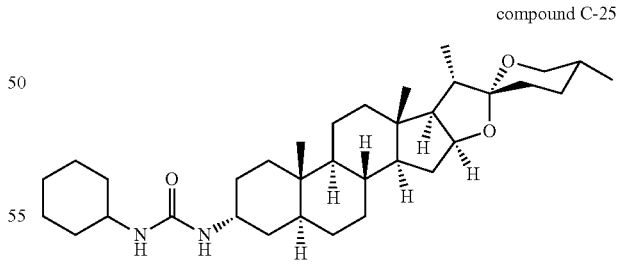
compound C-26
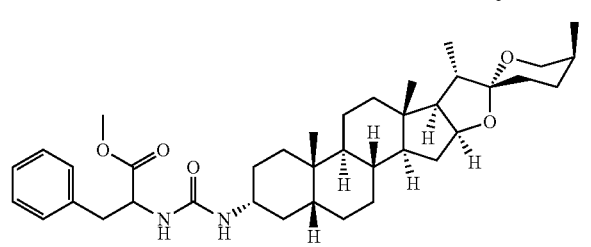

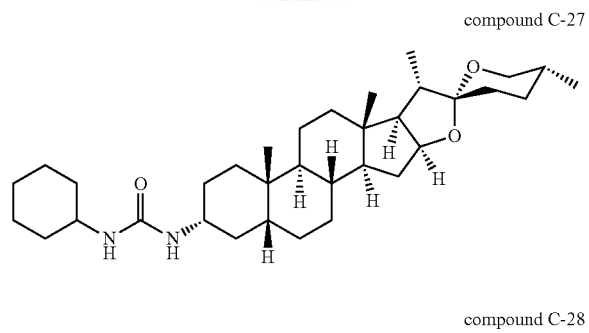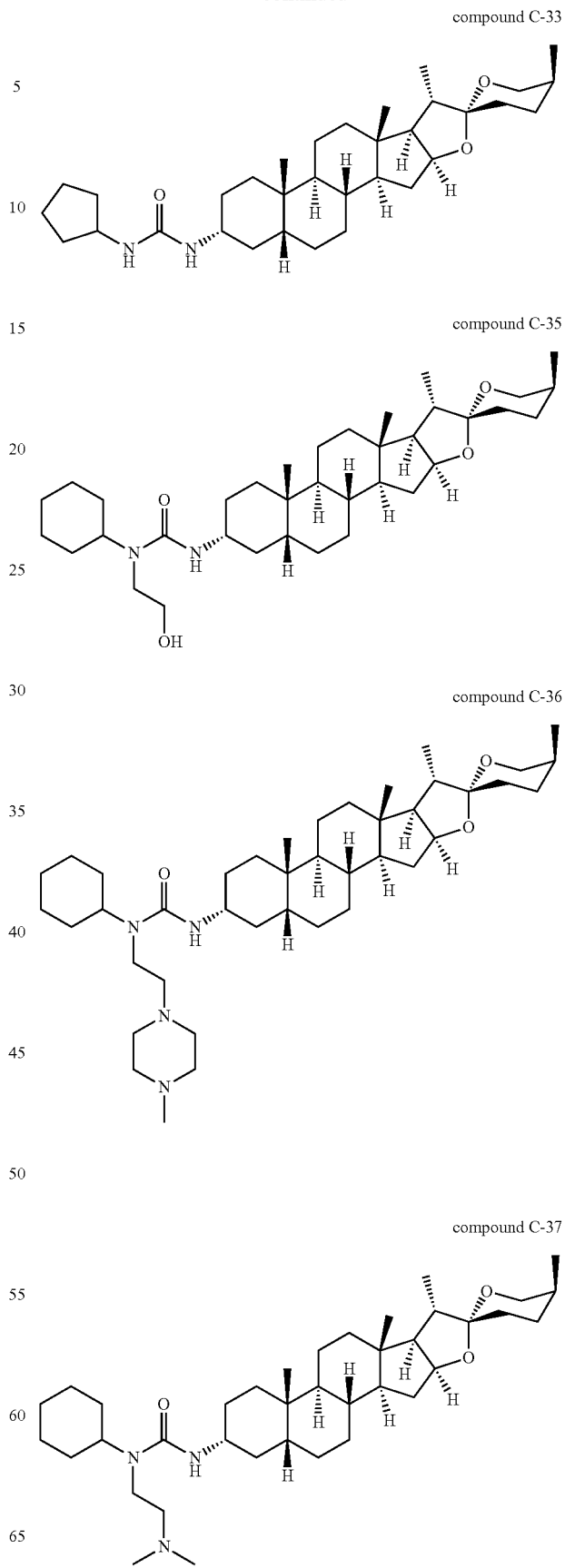

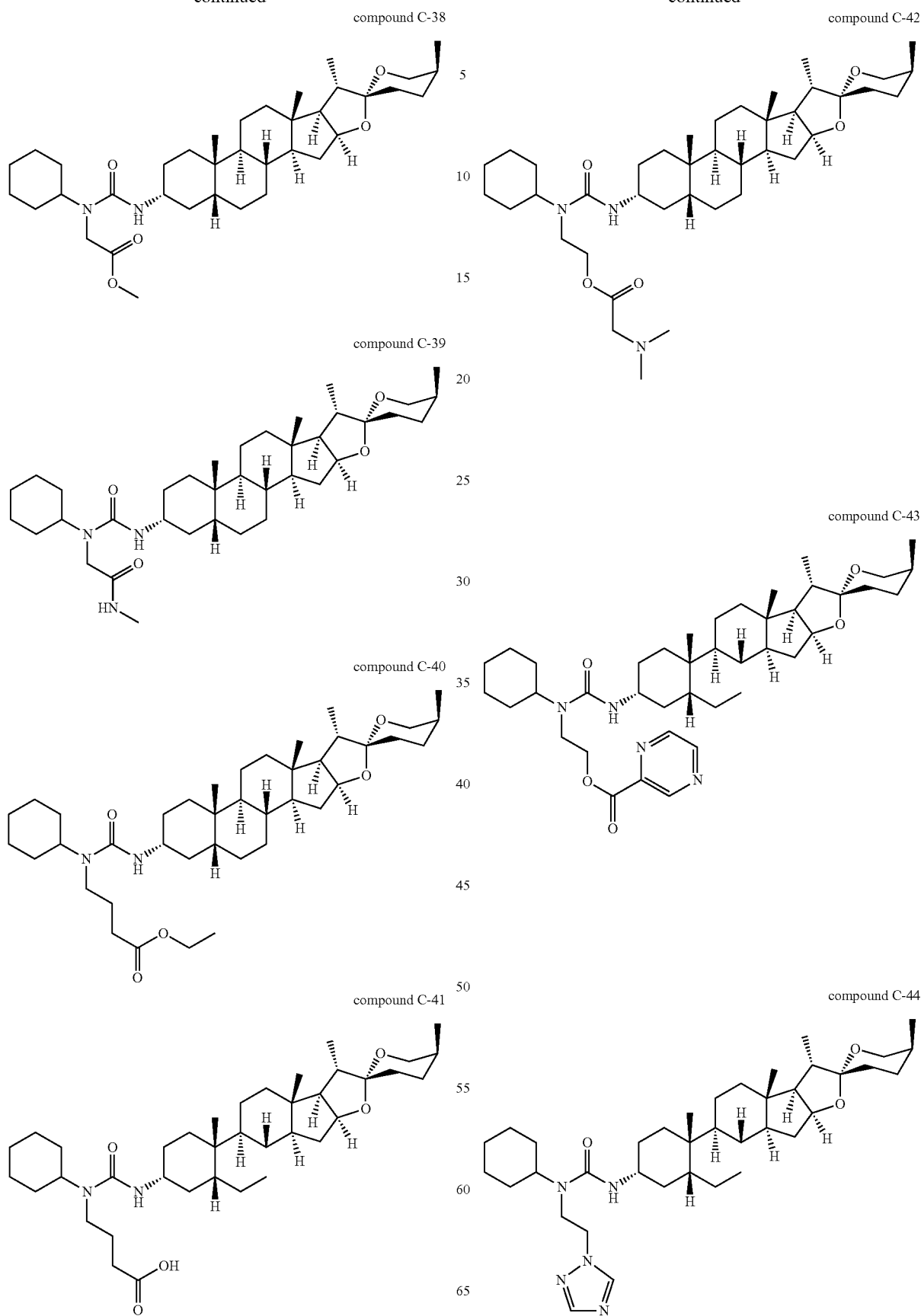

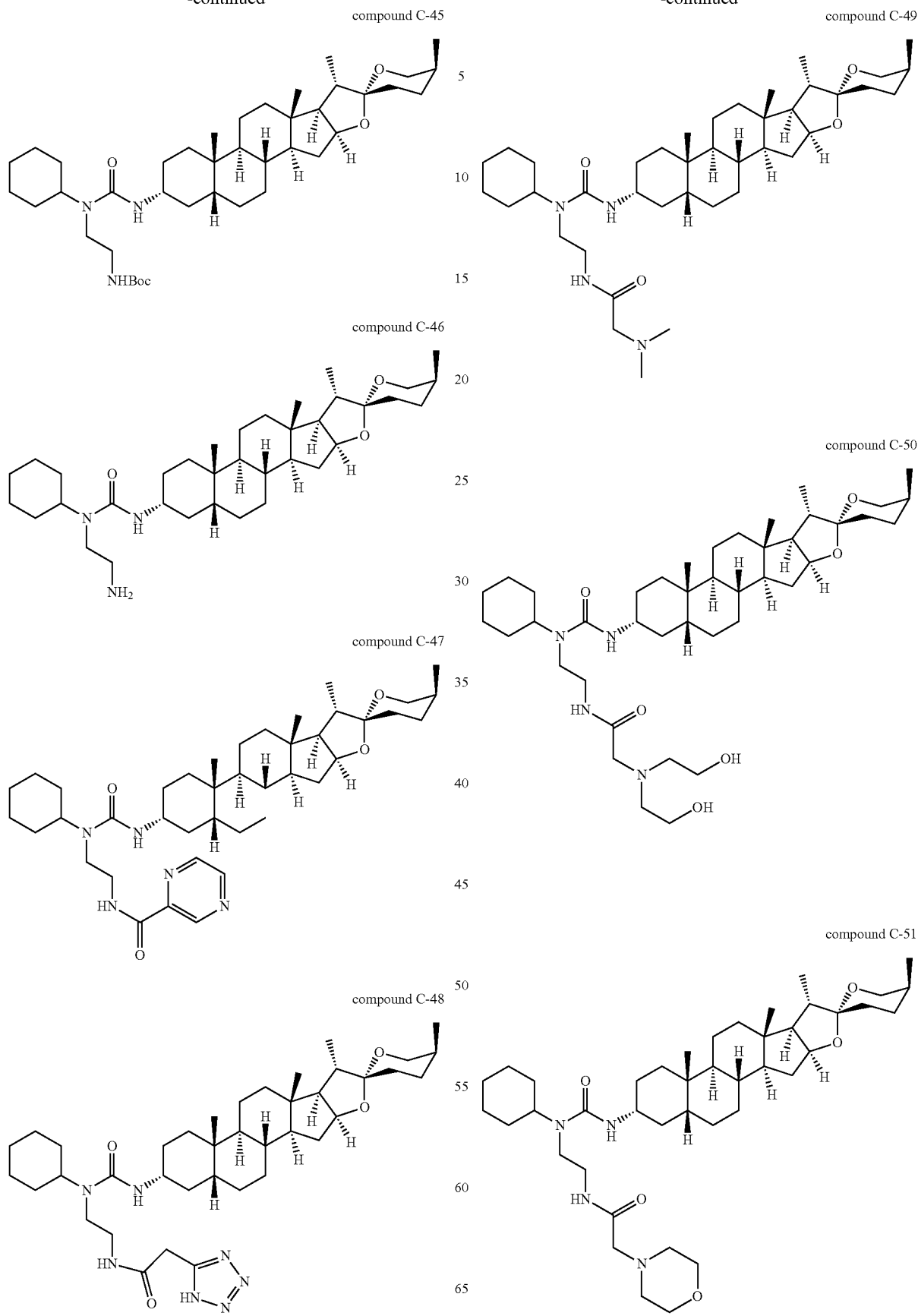

-continued compound C-52 compound C-53 compound C-54

-continued compound C-55 compound C-56

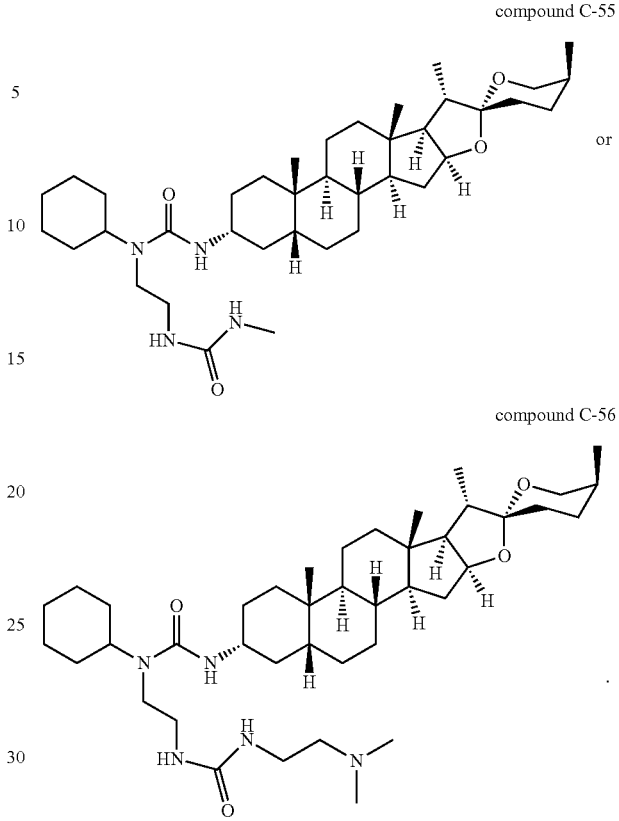

8. A preparation method of a compound, or the pharmaceutically acceptable salt, solvate, optically pure isomer or stereoisomer thereof according to claim 1, which comprises the step of:

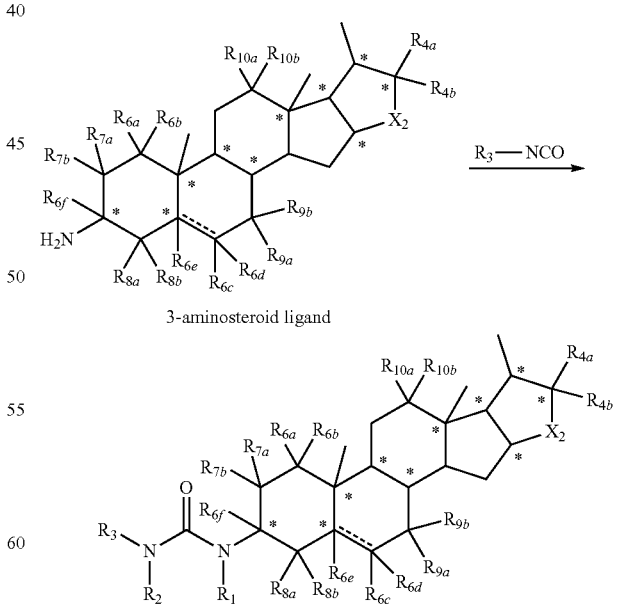

(a) reacting 3-aminosteroid ligand with an isocyanate to give compound of claim 1, wherein $R_1$ and $R_2$ are H, and the other substituents are as defined in claim 1;

or comprises the steps of:

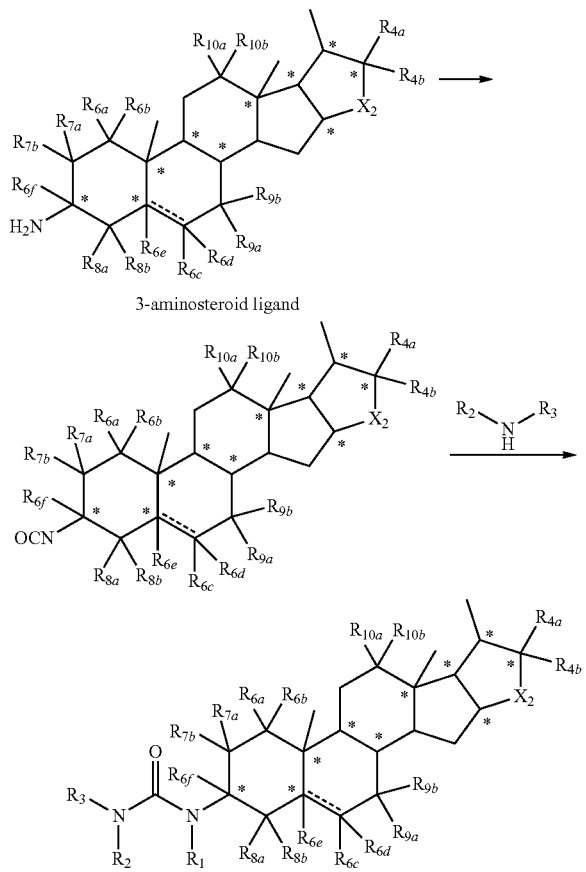

(i) preparing 3-isocyanate steroid compound from 3-aminosteroid ligand; and (ii) reacting 3-isocyanate steroid compound with $NHR_2R_3$ to give the compound of claim 1, wherein $R_1$ is H, and the other substituents are as defined in claim 1.

9. A pharmaceutical mixture comprising two or more compounds selected from the group consisting of the compound, or the pharmaceutically acceptable salt, solvate, optically pure isomer, stereoisomer thereof of claim 1.

10. A pharmaceutical composition comprising:

the compound, or the pharmaceutically acceptable salt, solvate, optically pure isomer, stereoisomer thereof of claim 1; and a pharmaceutically acceptable carrier.

11. A method for treating a disease, disorder or condition, which comprises: administering a compound or the pharmaceutically acceptable salt, solvate, optically pure isomer or stereoisomer thereof according to claim 1 to a subject in need of, wherein the disease, disorder or condition is selected from the group consisting of depression, anxiety, Parkinson's disease, Alzheimer's disease, Huntington's disease, schizophrenia, mania, cancer, tumor metastasis, hyperglycemia, hyperlipidemia, viral disorder, bacterial infection, angiogenic disorder, autoimmune disease, inflammatory disorder, and a condition associated with organ transplantation.

12. The method of claim 11, wherein the disease is depression.

13. The method of claim 11, wherein the subject is human.

* * * * *